(12) United States Patent
Jensen et al.

(10) Patent No.: US 12,312,416 B2
(45) Date of Patent: *May 27, 2025

(54) FLUORESCEIN-SPECIFIC CARS EXHIBITING OPTIMAL T CELL FUNCTION AGAINST FL-PLE LABELLED TUMORS

(71) Applicant: Seattle Children's Hospital, Seattle, WA (US)

(72) Inventors: Michael C. Jensen, Bainbridge Island, WA (US); James F. Matthaei, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 1188 days.

This patent is subject to a terminal disclaimer.

(21) Appl. No.: 16/965,859

(22) PCT Filed: Jan. 17, 2019

(86) PCT No.: PCT/US2019/014054
§ 371 (c)(1),
(2) Date: Jul. 29, 2020

(87) PCT Pub. No.: WO2019/156795
PCT Pub. Date: Aug. 15, 2019

(65) Prior Publication Data
US 2020/0354477 A1    Nov. 12, 2020

Related U.S. Application Data

(60) Provisional application No. 62/627,147, filed on Feb. 6, 2018.

(51) Int. Cl.
| | | |
|---|---|---|
| *C07K 14/725* | (2006.01) | |
| *A61P 35/00* | (2006.01) | |
| *C07K 16/30* | (2006.01) | |
| *C07K 16/44* | (2006.01) | |
| *G01N 33/574* | (2006.01) | |

(52) U.S. Cl.
CPC .......... *C07K 16/44* (2013.01); *C07K 14/7051* (2013.01); *C07K 16/30* (2013.01); *C07K 2317/53* (2013.01); *C07K 2319/33* (2013.01)

(58) Field of Classification Search
None
See application file for complete search history.

(56) References Cited

U.S. PATENT DOCUMENTS

| | | |
|---|---|---|
| 5,116,964 A | 5/1992 | Capon et al. |
| 5,202,238 A | 4/1993 | Fell, Jr. et al. |
| 5,216,132 A | 6/1993 | Basi |
| 5,359,046 A | 10/1994 | Capon et al. |
| 5,482,856 A | 1/1996 | Fell, Jr. et al. |
| 5,514,582 A | 5/1996 | Capon et al. |
| 5,525,503 A | 6/1996 | Rudd et al. |
| 5,538,866 A | 7/1996 | Israeli et al. |
| 5,670,148 A | 9/1997 | Sherwin et al. |
| 5,686,281 A | 11/1997 | Roberts |
| 5,712,149 A | 1/1998 | Roberts |
| 5,714,147 A | 2/1998 | Capon et al. |
| 5,741,899 A | 4/1998 | Capon et al. |
| 5,747,292 A | 5/1998 | Greenberg et al. |
| 5,830,755 A | 11/1998 | Nishimura et al. |
| 5,834,256 A | 11/1998 | Finer et al. |
| 5,837,544 A | 11/1998 | Capon et al. |
| 5,843,728 A | 12/1998 | Seed et al. |
| 5,851,828 A | 12/1998 | Seed et al. |
| 5,858,740 A | 1/1999 | Finer et al. |
| 5,906,936 A | 5/1999 | Eshhar et al. |
| 5,912,170 A | 6/1999 | Seed et al. |
| 5,912,172 A | 6/1999 | Eshhar et al. |
| 5,914,109 A | 6/1999 | Zolla-Pazner et al. |
| 5,935,818 A | 8/1999 | Israeli et al. |
| 5,969,102 A | 10/1999 | Bram et al. |
| 6,004,781 A | 12/1999 | Seed |
| 6,004,811 A | 12/1999 | Seed et al. |
| 6,005,004 A | 12/1999 | Katz et al. |
| 6,077,947 A | 6/2000 | Capon et al. |
| 6,083,751 A | 7/2000 | Feldhaus et al. |
| 6,103,521 A | 8/2000 | Capon et al. |
| 6,117,656 A | 9/2000 | Seed |
| 6,132,718 A | 10/2000 | Hansen et al. |
| 6,218,187 B1 | 4/2001 | Finer et al. |
| 6,261,787 B1 | 7/2001 | Davis et al. |

(Continued)

FOREIGN PATENT DOCUMENTS

| | | |
|---|---|---|
| CN | 102775500 | 11/2012 |
| EP | 2 177 230 | 4/2010 |

(Continued)

OTHER PUBLICATIONS

U.S. Appl. No. 18/459,302, filed Aug. 31, 2023, Low; Philip Stewart.*
Swanson et al. Fluorescent Cancer-Selective Alkylphosphocholine Analogs for Intraoperative Glioma Detection. Neurosurgery 2015; 76: 115-124.*
Hyman et al. Probing oxidative stress: Small molecule fluorescent sensors of metal ions, reactive oxygen species, and thiols. Coordination Chemistry Reviews (2012) 256: 2333-2356.*
Baiu et al. (Published online Jul. 26, 2017) Targeted Molecular Radiotherapy of Pediatric Solid Tumors Using a Radioiodinated Alkyl-Phospholipid Ether Analog. J Nucl Med 2018; 59: 244-250.*
Elsaid et al. Enhanced Radiosensitivity in Solid Tumors using a Tumor-selective Alkyl Phospholipid Ether Analog. Mol Cancer Ther. Nov. 2018; 17(11): 2320-2328.*

(Continued)

*Primary Examiner* — Ilia I Ouspenski
(74) *Attorney, Agent, or Firm* — Knobbe, Martens, Olson & Bear LLP

(57) ABSTRACT

Aspects described herein pertain to engineered chimeric antigen receptors (CARs) and compositions thereof having specificity and affinity for fluorescein containing ligands presented on the surface of tumor cells. Also provided herein are compositions including CARs further comprising a spacer arm and methods of making and using these compositions.

18 Claims, 41 Drawing Sheets

Specification includes a Sequence Listing.

(56) References Cited

U.S. PATENT DOCUMENTS

| | | |
|---|---|---|
| 6,319,494 B1 | 11/2001 | Capon et al. |
| 6,392,013 B1 | 5/2002 | Seed et al. |
| 6,395,152 B1 | 5/2002 | Wang |
| 6,406,697 B1 | 6/2002 | Capon et al. |
| 6,407,221 B1 | 6/2002 | Capon et al. |
| 6,410,014 B1 | 6/2002 | Seed et al. |
| 6,410,319 B1 | 6/2002 | Raubitschek et al. |
| 6,432,403 B1 | 8/2002 | Philips |
| 6,521,602 B1 | 2/2003 | Patel et al. |
| 6,524,572 B1 | 2/2003 | Li |
| 6,699,972 B1 | 3/2004 | Roffler et al. |
| 6,753,162 B1 | 6/2004 | Seed et al. |
| 6,759,243 B2 | 7/2004 | Kranz et al. |
| 6,770,749 B2 | 8/2004 | Ellenhorn et al. |
| 6,953,668 B1 | 10/2005 | Israeli et al. |
| 7,037,647 B1 | 5/2006 | Israeli et al. |
| 7,049,136 B2 | 5/2006 | Seed et al. |
| 7,052,906 B1 | 5/2006 | Lawson et al. |
| 7,070,995 B2 | 7/2006 | Jensen |
| 7,105,159 B1 | 9/2006 | Israeli et al. |
| 7,217,421 B1 | 5/2007 | McArthur et al. |
| 7,265,209 B2 | 9/2007 | Jensen |
| 7,320,787 B2 | 1/2008 | Seed et al. |
| 7,348,004 B2 | 3/2008 | Peters et al. |
| 7,354,587 B1 | 4/2008 | Hansen |
| 7,354,762 B2 | 4/2008 | Jensen |
| 7,381,408 B2 | 6/2008 | Mezo et al. |
| 7,404,956 B2 | 7/2008 | Peters et al. |
| 7,435,596 B2 | 10/2008 | Campana et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,482,005 B2 | 1/2009 | Kim |
| 7,514,537 B2 | 4/2009 | Jensen |
| 7,569,663 B2 | 8/2009 | Tykocinski et al. |
| 7,572,891 B2 | 8/2009 | Belldegrun et al. |
| 7,618,817 B2 | 11/2009 | Campbell |
| 7,632,497 B2 | 12/2009 | Stavenhagen |
| 7,655,461 B2 | 2/2010 | Finn et al. |
| 7,666,424 B2 | 2/2010 | Cheung et al. |
| 7,723,111 B2 | 5/2010 | Hwu et al. |
| 7,741,465 B1 | 6/2010 | Eshhar et al. |
| 7,871,817 B2 | 1/2011 | Voss et al. |
| 7,906,620 B2 | 3/2011 | Eisenbach et al. |
| 7,919,079 B2 | 4/2011 | Simmons et al. |
| 7,939,059 B2 | 5/2011 | Yang et al. |
| 7,994,298 B2 | 8/2011 | Zhang et al. |
| 7,998,736 B2 | 8/2011 | Morgan et al. |
| 8,105,830 B2 | 1/2012 | Weldanz et al. |
| 8,148,154 B2 | 4/2012 | Cheung et al. |
| 8,163,887 B2 | 4/2012 | Hansen |
| 8,211,422 B2 | 7/2012 | Eshhar et al. |
| RE43,586 E | 8/2012 | Israeli et al. |
| 8,252,914 B2 | 8/2012 | Zhang et al. |
| 8,324,353 B2 | 12/2012 | Jensen |
| 8,389,282 B2 | 3/2013 | Sadelain et al. |
| 8,399,645 B2 | 3/2013 | Campana et al. |
| 8,409,577 B2 | 4/2013 | Thompson et al. |
| 8,450,112 B2 | 5/2013 | Li et al. |
| 8,465,743 B2 | 6/2013 | Rosenberg et al. |
| 8,486,911 B2 | 7/2013 | Okada et al. |
| 8,497,118 B2 | 7/2013 | Jensen |
| 8,741,306 B2 | 6/2014 | Belldegrun et al. |
| 8,802,374 B2 | 8/2014 | Jensen |
| 8,809,050 B2 | 8/2014 | Vera et al. |
| 8,822,196 B2 | 9/2014 | Rosenberg et al. |
| 8,822,647 B2 | 9/2014 | Jensen |
| 8,859,229 B2 | 10/2014 | Rabinovich et al. |
| 8,877,199 B2 | 11/2014 | Rader et al. |
| 8,906,682 B2 | 12/2014 | June et al. |
| 8,932,830 B2 | 1/2015 | Peters et al. |
| 8,946,385 B2 | 2/2015 | Kawal |
| 8,956,860 B2 | 2/2015 | Vera et al. |
| 9,023,621 B2 | 5/2015 | Gurney et al. |
| 9,040,669 B2 | 5/2015 | Cheung et al. |
| 9,062,127 B2 | 6/2015 | Voss et al. |
| 9,074,000 B2 | 7/2015 | Scheinberg et al. |
| 9,089,520 B2 | 7/2015 | Brenner |
| 9,101,609 B2 | 8/2015 | Tan et al. |
| 9,133,436 B2 | 9/2015 | Riley et al. |
| 9,156,915 B2 | 10/2015 | Waldman et al. |
| 9,163,258 B2 | 10/2015 | Riddell et al. |
| 9,175,308 B2 | 11/2015 | Shiku et al. |
| 9,211,321 B2 | 12/2015 | Karlsson-Parra et al. |
| 9,212,229 B2 | 12/2015 | Schönfeld et al. |
| 9,220,728 B2 | 12/2015 | Sadelain et al. |
| 9,226,936 B2 | 1/2016 | Hu et al. |
| 9,242,014 B2 | 1/2016 | Kipps et al. |
| 9,266,960 B2 | 2/2016 | Morgan et al. |
| 9,272,002 B2 | 3/2016 | Powell, Jr. et al. |
| 9,273,283 B2 | 3/2016 | Sentman |
| 9,279,008 B2 | 3/2016 | Scholler et al. |
| 9,334,330 B2 | 5/2016 | Birkle et al. |
| 9,345,748 B2 | 5/2016 | Morgan et al. |
| 9,352,036 B2 | 5/2016 | McBride et al. |
| 9,359,447 B2 | 6/2016 | Feldman et al. |
| 9,365,641 B2 | 6/2016 | June et al. |
| 9,393,268 B2 | 7/2016 | Waldman et al. |
| 9,393,292 B2 | 7/2016 | Brenner |
| 9,394,364 B2 | 7/2016 | Ho et al. |
| 9,394,368 B2 | 7/2016 | Brogdon et al. |
| 9,402,888 B2 | 8/2016 | Hildegund et al. |
| 9,408,904 B2 | 8/2016 | Wright et al. |
| 9,409,992 B2 | 8/2016 | Ho et al. |
| 9,409,994 B2 | 8/2016 | Ho et al. |
| 9,416,190 B2 | 8/2016 | Ho et al. |
| 9,422,351 B2 | 8/2016 | Scholler et al. |
| 9,434,935 B2 | 9/2016 | Spencer et al. |
| 9,446,105 B2 | 9/2016 | Powell et al. |
| 9,447,194 B2 | 9/2016 | Jensen |
| 9,453,075 B2 | 9/2016 | Cheung et al. |
| 9,464,140 B2 | 10/2016 | June et al. |
| 9,469,684 B2 | 10/2016 | Finn et al. |
| 9,476,028 B2 | 10/2016 | Karlsson-Parra et al. |
| 9,481,728 B2 | 11/2016 | June et al. |
| 9,487,800 B2 | 11/2016 | Schonfeld et al. |
| 9,492,499 B2 | 11/2016 | Jaynes et al. |
| 9,492,529 B2 | 11/2016 | Karlsson-Parra et al. |
| 9,493,740 B2 | 11/2016 | Brenner et al. |
| 9,499,629 B2 | 11/2016 | June et al. |
| 9,499,855 B2 | 11/2016 | Hyde et al. |
| 9,511,092 B2 | 12/2016 | Campana et al. |
| 9,518,123 B2 | 12/2016 | June et al. |
| 9,522,955 B2 | 12/2016 | Rosenberg et al. |
| 9,540,445 B2 | 1/2017 | June et al. |
| 9,540,448 B2 | 1/2017 | Scheinberg et al. |
| 9,561,291 B2 | 2/2017 | Kovesdi et al. |
| 9,562,087 B2 | 2/2017 | Ring et al. |
| 9,567,399 B1 | 2/2017 | Campbell et al. |
| 9,572,836 B2 | 2/2017 | June et al. |
| 9,572,837 B2 | 2/2017 | Wu |
| 9,573,988 B2 | 2/2017 | Brogdon et al. |
| 9,574,014 B2 | 2/2017 | Williams et al. |
| 9,587,020 B2 | 3/2017 | Wu et al. |
| 9,587,237 B2 | 3/2017 | Hyde et al. |
| 9,597,357 B2 | 3/2017 | Gregory et al. |
| 9,605,049 B2 | 3/2017 | Campana et al. |
| 9,624,292 B2 | 4/2017 | Voss et al. |
| 9,624,306 B2 | 4/2017 | Morgan et al. |
| 9,629,877 B2 | 4/2017 | Cooper et al. |
| 9,636,388 B2 | 5/2017 | Lawman et al. |
| 9,636,416 B2 | 5/2017 | Peters et al. |
| 9,642,906 B2 | 5/2017 | Ramos et al. |
| 9,650,428 B2 | 5/2017 | Sampath et al. |
| 9,657,105 B2 | 5/2017 | Forman et al. |
| 9,662,405 B2 | 5/2017 | Waldman et al. |
| 9,663,756 B1 | 5/2017 | Lipkens et al. |
| 9,663,763 B2 | 5/2017 | Sentman |
| 9,669,058 B2 | 6/2017 | Li et al. |
| 9,670,281 B2 | 6/2017 | Lim et al. |
| 9,676,867 B2 | 6/2017 | Marasco et al. |
| 9,688,740 B2 | 6/2017 | Choi et al. |
| 9,688,760 B2 | 6/2017 | Kufer et al. |
| 9,694,033 B2 | 7/2017 | Yi et al. |

(56) References Cited

U.S. PATENT DOCUMENTS

| | | | |
|---|---|---|---|
| 9,701,758 B2 | 7/2017 | Cooper et al. | |
| 9,708,384 B2 | 7/2017 | Scholler et al. | |
| 9,714,278 B2 | 7/2017 | June et al. | |
| 9,717,745 B2 | 8/2017 | He | |
| 9,725,519 B2 | 8/2017 | Masuko et al. | |
| 9,733,245 B2 | 8/2017 | Kawai | |
| 9,738,726 B2 | 8/2017 | Dimitrov et al. | |
| 9,745,368 B2 | 8/2017 | Milone et al. | |
| 9,765,142 B2 | 9/2017 | Dimitrov et al. | |
| 9,765,156 B2 | 9/2017 | June et al. | |
| 9,765,330 B1 | 9/2017 | Niazi et al. | |
| 9,765,342 B2 | 9/2017 | Kochenderfer | |
| 9,777,061 B2 | 10/2017 | Ebersbach et al. | |
| 9,777,064 B2 | 10/2017 | Wang et al. | |
| 9,783,591 B2 | 10/2017 | June et al. | |
| 9,789,174 B2 | 10/2017 | Karlsson-Parra et al. | |
| 9,790,267 B2 | 10/2017 | Kaplan | |
| 9,790,278 B2 | 10/2017 | Sentman et al. | |
| 9,790,282 B2 | 10/2017 | Orentas et al. | |
| 9,790,467 B2 | 10/2017 | Kevlahan et al. | |
| 9,796,783 B2 | 10/2017 | Agerstam et al. | |
| 9,802,997 B2 | 10/2017 | Mahr et al. | |
| 9,803,022 B2 | 10/2017 | Ho et al. | |
| 9,808,486 B2 | 11/2017 | Georgiou et al. | |
| 9,809,581 B2 | 11/2017 | Chen et al. | |
| 9,815,901 B2 | 11/2017 | Brogdon et al. | |
| 9,821,011 B1 | 11/2017 | Sentman | |
| 9,821,012 B2 | 11/2017 | Wu et al. | |
| 9,822,340 B1 | 11/2017 | Sentman | |
| 9,828,399 B2 | 11/2017 | Tremblay et al. | |
| 9,828,435 B2 | 11/2017 | Evans et al. | |
| 9,833,476 B2 | 12/2017 | Zhang et al. | |
| 9,833,480 B2 | 12/2017 | Junghans et al. | |
| 9,834,545 B2 | 12/2017 | Chen et al. | |
| 9,834,590 B2 | 12/2017 | Campana et al. | |
| 9,840,548 B2 | 12/2017 | Mahr et al. | |
| 9,845,362 B2 | 12/2017 | Mukherjee | |
| 9,849,092 B2 | 12/2017 | Peyman | |
| 9,855,297 B2 | 1/2018 | Duchateau et al. | |
| 9,855,298 B2 | 1/2018 | Bot et al. | |
| 9,856,322 B2 | 1/2018 | Campana et al. | |
| 9,856,497 B2 | 1/2018 | Qi et al. | |
| 9,856,501 B2 | 1/2018 | O'Keefe et al. | |
| 9,862,756 B2 | 1/2018 | Mahr et al. | |
| 9,862,775 B2 | 1/2018 | Kwon et al. | |
| 9,868,774 B2 | 1/2018 | Orentas et al. | |
| 9,868,951 B2 | 1/2018 | Hu et al. | |
| 9,873,894 B2 | 1/2018 | Conway et al. | |
| 9,879,087 B2 | 1/2018 | DeSander et al. | |
| 9,885,021 B2 | 2/2018 | Bollard et al. | |
| 9,889,160 B2 | 2/2018 | Jantz et al. | |
| 9,889,161 B2 | 2/2018 | Jantz et al. | |
| 9,890,393 B2 | 2/2018 | Duchateau et al. | |
| 10,279,047 B2 | 5/2019 | Won et al. | |
| 11,311,576 B2* | 4/2022 | Jensen | A61K 31/519 |
| 11,649,288 B2* | 5/2023 | Jensen | C07K 16/32 |
| | | | 424/179.1 |
| 11,779,602 B2* | 10/2023 | Low | A61K 39/464404 |
| | | | 424/93.21 |
| 2001/0031252 A1 | 10/2001 | Low et al. | |
| 2002/0004052 A1 | 1/2002 | Berd et al. | |
| 2002/0111474 A1 | 8/2002 | Capon et al. | |
| 2003/0175288 A1 | 9/2003 | Itoh | |
| 2004/0171096 A1* | 9/2004 | Ferguson | C07F 9/65522 |
| | | | 435/18 |
| 2005/0113564 A1 | 5/2005 | Campana | |
| 2006/0155115 A1 | 7/2006 | Jakobsen et al. | |
| 2008/0051380 A1 | 2/2008 | Auerbach et al. | |
| 2009/0011984 A1 | 1/2009 | Yla-Herttuala et al. | |
| 2009/0202501 A1 | 8/2009 | Zhang et al. | |
| 2010/0135974 A1 | 6/2010 | Eshhar et al. | |
| 2010/0278830 A1 | 11/2010 | Shoemaker et al. | |
| 2011/0172254 A1 | 7/2011 | Leamon | |
| 2011/0178279 A1 | 7/2011 | Williams et al. | |
| 2012/0093842 A1 | 4/2012 | Eshhar et al. | |
| 2012/0302466 A1 | 11/2012 | Sentman | |
| 2013/0143895 A1 | 6/2013 | McAllister et al. | |
| 2013/0156794 A1 | 6/2013 | Eshhar et al. | |
| 2013/0287752 A1* | 10/2013 | Davila | A61K 47/6859 |
| | | | 424/93.71 |
| 2013/0309267 A1 | 11/2013 | Simmons et al. | |
| 2013/0309258 A1 | 12/2013 | June et al. | |
| 2013/0323834 A1 | 12/2013 | Brenner | |
| 2013/0344066 A1 | 12/2013 | Faham et al. | |
| 2014/0004132 A1 | 1/2014 | Brenner et al. | |
| 2014/0004137 A1 | 1/2014 | Ovaa et al. | |
| 2014/0017170 A1 | 1/2014 | Irvine et al. | |
| 2014/0120136 A1 | 5/2014 | Katsikis et al. | |
| 2014/0134142 A1 | 5/2014 | Smith et al. | |
| 2014/0134720 A1 | 5/2014 | Stauss et al. | |
| 2014/0227237 A1 | 8/2014 | June et al. | |
| 2014/0255363 A1 | 9/2014 | Metelitsa et al. | |
| 2014/0271582 A1 | 9/2014 | Forman et al. | |
| 2014/0271635 A1 | 9/2014 | Brogdon et al. | |
| 2014/0274909 A1 | 9/2014 | Orentas et al. | |
| 2014/0286973 A1 | 9/2014 | Powell | |
| 2014/0286987 A1 | 9/2014 | Spencer et al. | |
| 2014/0308259 A1 | 10/2014 | Scholler et al. | |
| 2014/0322183 A1 | 10/2014 | Milone et al. | |
| 2014/0322212 A1 | 10/2014 | Brogdon et al. | |
| 2014/0322275 A1 | 10/2014 | Brogdon et al. | |
| 2014/0378389 A1 | 12/2014 | Robbins et al. | |
| 2015/0110760 A1 | 4/2015 | Zhang et al. | |
| 2015/0139943 A1 | 5/2015 | Campana et al. | |
| 2015/0152181 A1 | 6/2015 | Sentman et al. | |
| 2015/0225470 A1 | 8/2015 | Zhang et al. | |
| 2015/0238631 A1 | 8/2015 | Kim et al. | |
| 2015/0283178 A1 | 10/2015 | June et al. | |
| 2015/0306141 A1* | 10/2015 | Jensen | C07K 14/70521 |
| | | | 435/325 |
| 2015/0307564 A1 | 10/2015 | Young et al. | |
| 2015/0307842 A1 | 10/2015 | Sentman | |
| 2015/0314014 A1 | 11/2015 | Lauremann | |
| 2015/0320799 A1 | 11/2015 | Low et al. | |
| 2015/0328292 A1 | 11/2015 | Spencer et al. | |
| 2015/0368342 A1 | 12/2015 | Wu et al. | |
| 2016/0046700 A1 | 2/2016 | Foster et al. | |
| 2016/0046724 A1 | 2/2016 | Brogdon et al. | |
| 2016/0051651 A1 | 2/2016 | Brogdon et al. | |
| 2016/0058857 A1 | 3/2016 | Spencer et al. | |
| 2016/0068601 A1 | 3/2016 | Brogdon et al. | |
| 2016/0096892 A1 | 4/2016 | Brogdon et al. | |
| 2016/0120907 A1 | 5/2016 | Sentman | |
| 2016/0136190 A1 | 5/2016 | Weichert et al. | |
| 2016/0151465 A1 | 6/2016 | Slawin et al. | |
| 2016/0166613 A1 | 6/2016 | Spencer et al. | |
| 2016/0175359 A1 | 6/2016 | Spencer et al. | |
| 2016/0340649 A1 | 11/2016 | Brown et al. | |
| 2016/0361360 A1 | 12/2016 | Chang et al. | |
| 2017/0166877 A1 | 6/2017 | Bayle et al. | |
| 2017/0290900 A1 | 10/2017 | Low et al. | |
| 2017/0306303 A1 | 10/2017 | Taunton et al. | |
| 2017/0340672 A1 | 11/2017 | Wu et al. | |
| 2017/0356010 A1 | 12/2017 | Frost et al. | |
| 2019/0161531 A1 | 5/2019 | Pule et al. | |
| 2019/0209611 A1 | 7/2019 | Eckardt et al. | |
| 2019/0224237 A1 | 7/2019 | Jensen et al. | |
| 2019/0255109 A1* | 8/2019 | Low | C07K 16/44 |
| 2019/0292517 A1 | 9/2019 | Cheung et al. | |
| 2019/0388468 A1 | 12/2019 | Lock et al. | |
| 2020/0087399 A1 | 3/2020 | Jensen et al. | |
| 2021/0317407 A1* | 10/2021 | Jensen | A61K 35/17 |
| 2022/0125841 A1* | 4/2022 | Jensen | A61P 35/00 |
| 2022/0257652 A1* | 8/2022 | Jensen | C12N 5/0636 |
| 2022/0280648 A1* | 9/2022 | Low | A61K 47/545 |

(56) References Cited

U.S. PATENT DOCUMENTS

| | | | | |
|---|---|---|---|---|
| 2023/0172981 | A1* | 6/2023 | Jensen | C07K 16/2803 424/93.71 |
| 2023/0322925 | A1* | 10/2023 | Jensen | A61P 35/00 424/179.1 |

FOREIGN PATENT DOCUMENTS

| | | |
|---|---|---|
| EP | 2 614 077 | 8/2016 |
| JP | 2004-113062 | 4/2004 |
| WO | WO 86/04356 | 7/1986 |
| WO | WO 92/10591 | 6/1992 |
| WO | WO 92/15671 | 9/1992 |
| WO | WO 01/091625 | 12/2001 |
| WO | WO 02/088334 | 11/2002 |
| WO | WO 05/084716 | 9/2005 |
| WO | WO 06/029879 | 3/2006 |
| WO | WO 08/057437 | 5/2008 |
| WO | WO 09/091826 | 7/2009 |
| WO | WO 09/117117 | 9/2009 |
| WO | WO 10/025177 | 3/2010 |
| WO | WO 12/054825 | 4/2012 |
| WO | WO 12/082841 | 6/2012 |
| WO | WO 12/138475 | 10/2012 |
| WO | WO 13/039889 | 3/2013 |
| WO | WO 13/177247 | 11/2013 |
| WO | WO 14/011984 | 1/2014 |
| WO | WO 14/031687 | 2/2014 |
| WO | WO 14/043441 | 3/2014 |
| WO | WO 14/055771 | 4/2014 |
| WO | WO 14/068388 | 5/2014 |
| WO | WO 14/100615 | 6/2014 |
| WO | WO 14/127261 | 8/2014 |
| WO | WO 15/057834 | 4/2015 |
| WO | WO 15/057852 | 4/2015 |
| WO | WO 15/164594 | 10/2015 |
| WO | WO 16/025322 | 2/2016 |
| WO | WO 16/098078 | 6/2016 |
| WO | WO 16/102965 | 6/2016 |
| WO | WO 16/054520 | 7/2016 |
| WO | WO 16/149665 | 9/2016 |
| WO | WO 16/168766 | 10/2016 |
| WO | WO 2016/168769 A1 | 10/2016 |
| WO | WO 16/201300 | 12/2016 |
| WO | WO 16/210447 | 12/2016 |
| WO | WO 17/029511 | 2/2017 |
| WO | WO 17/029512 | 2/2017 |
| WO | WO 17/068360 | 4/2017 |
| WO | WO 17/068361 | 4/2017 |
| WO | WO 17/137758 | 8/2017 |
| WO | WO 17/137759 | 8/2017 |
| WO | WO 2017/143094 A1 | 8/2017 |
| WO | WO 17/165245 | 9/2017 |
| WO | WO 17/165571 | 9/2017 |
| WO | WO 17/177149 | 10/2017 |
| WO | WO 17/180587 | 10/2017 |
| WO | WO 17/216561 | 12/2017 |
| WO | WO 17/216562 | 12/2017 |
| WO | WO 18/013797 | 1/2018 |
| WO | WO 18/111834 | 6/2018 |
| WO | WO 18/115146 | 6/2018 |
| WO | WO 2018/111763 A1 | 6/2018 |
| WO | WO 18/152451 | 8/2018 |
| WO | WO 2018/148224 A1 | 8/2018 |
| WO | WO 18/160622 | 9/2018 |
| WO | WO 19/060425 | 3/2019 |
| WO | WO 19/156795 | 8/2019 |

OTHER PUBLICATIONS

Yamamoto et al. Interaction of poly(ethylene glycol)-conjugated phospholipids with supported lipid membranes and their influence on protein adsorption. Science and Technology of Advanced Materials 2016; 17(1): 677-684.*

Tapeinos et al. Physical, Chemical, and Biological Structures based on ROS-Sensitive Moieties that are Able to Respond to Oxidative Microenvironments. Adv. Mater. 2016, 28: 5553-5585.*

Sutherland et al. Modular Chimeric Antigen Receptor Systems for Universal Car T Cell Retargeting. Int. J. Mol. Sci. 2020, 21(19), 7222, p. 1-14.*

Liu et al. Phospholipid-Graphene Nanoassembly as a Fluorescence Biosensor for Sensitive Detection of Phospholipase D Activity. Anal. Chem. 2012, 84, 14, 5944-5950.*

Ohgaki et al. Ratiometric fluorescence imaging of cell surface pH by poly(ethylene glycol)-phospholipid conjugated with fluorescein isothiocyanate. Scientific Reports 2017; 7: 17484, p. 1-9.*

International Search Report for PCT/US2019/014054 dated May 31, 2019.

Abken, H. et al. Chimeric T-Cell Receptors: Highly Specific Tools to Target Cytotoxic T-Lymphocytes to Tumour Cells, Cancer Treatment Reviews (1997); 23:97-112.

Abken, H., et al., Tuning tumor-specific T-cell activation: a matter of costimulation? Trends in Immunology vol. 23 No. 5 May 2002: 240-45.

Abstracts for the 26th Annual Scientific Meeting of the Society for Immunotherapy of Cancer (SITC), J Immunother., vol. 34, No. 9, Nov.-Dec. 2011 (62 pp.).

Airenne et al., Recombinant avidin and avidin-fusion proteins, Biomolecular Engineering 16 (1999) 87-92.

Alcover et al., A soluble form of the human CD8 alpha chain expressed in the baculovirus system: Biochemical characterization and binding to MHC Class I , Molecular Immunology, vol. 30, No. 1, pp. 55-67, 1993.

Alexander et al., Indoleamine 2,3-Dioxygenase Expression in Transplanted NOD Islets Prolongs Graft Survival After Adoptive Transfer of Diabetogenic Splenocytes, Diabetes 2002, vol. 51 pp. 356-365.

Alonso-Camino et al. CARbodies: Human Antibodies Against Cell Surface Tumor Antigens Selected From Repertoires Displayed on T Cell Chimeric Antigen Receptors. (2013) Mol Ther Nucl Acids 2, e93 (11 pages).

Altenschmidt, U. et al. Adoptive transfer of in vitro-targeted, activated T lymphocytes results in total tumor regression, J. Immunol. (1997); 159:5509-15.

Altenschmidt, U., et al., Specific cytotoxic T lymphocytes in gene therapy, J. Mol. Med. (1997); 75, 259-266.

Altschul, S. et al., Basic local alignment search tool, J. Mol. Bio., 1990, 215, 403-410.

Altvater, B., et al., 284 (CD244) Signaling by Recombinant Antigen-specific Chimeric Receptors Costimulates Natural Killer Cell Activation to Leukemia and Neuroblastoma Cells , Clin Cancer Res 2009;15(15) Aug. 1, 2009: 4857-66.

Alvarez-Vallina, L. et al., Antigen-specific targeting of CD28-mediated T cell co-stimulation using chimeric single-chain antibody variable fragment-CD28 receptors, Eur. J. Immunol, 1996, 26, 2304-2309.

Amin et al., The Eighth Edition AJCC Cancer Staging Manual: Continuing to Build a Bridge From a Population-Based to a More Personalized Approach to Cancer Staging, CA Cancer J Clin (2017) vol. 67, No. 2, pp. 93-99.

An et al., IgG2m4, an engineered antibody isotype with reduced Fc function, mAbs 2009, Landes Bioscience, 1:6, 572-579.

Ang et al., Generating a Chimeric Antigen Receptor to Redirect T-Cell Specificity after Infusion , Molecular Therapy vol. 19, Supplement 1, May 2011, S137-S138.

Arch, R, et al., 4-1BB and Ox40 Are Members of a Tumor Necrosis Factor (TNF)-Nerve Growth Factor Receptor Subfamily That Bind TNF Receptor-Associated Factors and Activate Nuclear Factor kB, Molecular and Cellular Biology (1998); 558-565.

Aruffo, A, et al., Molecular cloning of a CD28 cDNA by a high-efficiency COS cell expression system, Proc. Nati. Acad. Sci. USA (1987); 84: 8573-8577.

Baba et al., N-Linked Carbohydrate on Human Leukocyte Antigen-C and Recognition by Natural Killer Cell Inhibitory Receptors , Human Immunology 61, 1202-1218 (2000).

Baniyash et al., The T Cell Antigen Receptor Zeta Chain is Tyrosine Phosphorylated open Activation the Journal of Biological Chemistry, vol. 263, No. 34, Issue of Dec. 5, pp. 18225-18230.

(56) References Cited

OTHER PUBLICATIONS

Barber, et al., Chimeric NKG2D Receptor-Expressing T Cells as an Immunotherapy for Multiple Myeloma, Exp Hematol. (Oct. 2008); 36(10):1318-28.
Barocas et al., A population-based study of renal cell carcinoma and prostate cancer in the same patients, BJU International, (2006) 97(1): 33-36.
Barrett et al., Chimeric Antigen Receptor Therapy for Cancer Annual Review of Medicine vol. 65: 333-347 (2014).
Bauer et al., Activation of NK Cells and T Cells by NKG2D, a Receptor for Stress-Inducible MICA, Science 1999, vol. 285 pp. 727-729.
Bauer, A, et al., Differential signal transduction via T-cell receptor CD3'2, CD3C-,v,and CD3'q2 isoforms, Proc. Nati. Acad. Sci. USA (1991); 88: 3842-3846.
Baum et al. Retrovirus vectors: toward the plentivirus? (2006) Molecular Therapy: The Journal of the American Society of Gene Therapy. 13:1050-1063.
Becker, M. L. B., et al., Expression of a hybrid immunoglobulin-T cell receptor protein in transgenic mice, Cell (1989); 58:911-921.
Bedzyk, WD et al., Active site structure and antigen binding properties of idiotypically cross-reactive anti-fluorescein monoclonal antibodies, J Biol Chem., 1990, 265, 133-138.
Bejcek, B, et al., Development and Characterization of Three Recombinant Single Chain Antibody Fragments (scFvs) Directed against the CD19 Antigen1, Cancer Research55, (1995); 2346-2351.
Berg et al., Section 3.2 Primary Structure: Amino Acids Are Linked by Peptide Bonds to Form Polypeptide Chains Biochemistry. 5th Ed. New York. W.H. Freeman; 2002, pp. 1-16.
Berger, C., et al., Analysis of trans gene-specific immune responses that limit the in vivopersistence of adoptively transferred HSV-TK-modified donor T cells after allogeneic hematopoietic cell transplantation. Blood, 2006, 107(6): p. 2294-302.
Bluemel, C., et al., Epitope distance to the target cell membrane and antigen size determine the potency of T cell-mediated lysis by BiTE antibodies specific for a large melanoma surface antigen. Cancer Immunol Immunother (2010); 59(8): 1197-209.
Boder et al., Directed evolution of antibody fragments with monovalent femtomolar antigen-binding affinity, PNAS (Sep. 26, 2000) vol. 97, No. 20, pp. 10701-10705.
Bolhuis, R. L. et al. Preparation for a phase I/II study using autologous gene modified T lymphocytes for treatment of metastatic renal cancer patients., Adv. Exp. Med. Biol. (1998); 451:547-55.
Boomer et al., Cutting Edge: A Double-Mutant Knockin of the CD28 YMNM and PYAP Motifs Reveals a Critical Role for the YMNM Motif in Regulation of T Cell Proliferation andBcl-x L Expression The Journal of Immunology. 2014; 192, pp. 3465-3469.
Boomer, J, et al.,, An Enigmatic Tail of CD28 Signaling, Washington University School of Medicine (2010); 1-20.
Boursier et al., Evidence for an Extended Structure of the T-cell Co-receptor CD8α as Deduced from the Hydrodynamic Properties of Soluble Forms of the Extracellular Region*, The Journal of Biological Chemistry 1993, vol. 268, No. 3, Issue of Jan. 25, pp. 2013-2020.
Brennan et al., Carbohydrate Recognition by a Natural Killer Cell Receptor, Ly-49C*, The Journal of Biological Chemistry 1995, vol. 270, No. 17, Issue of Apr. 28, pp. 9691-9694.
Brentjens et al., CD19-targeted T cells rapidly induce molecular remissions in adults with chemotherapy-refractory acute lymphoblastic leukemia. Sci Transl Med. 2013 5(177)ra38 (11 pages).
Brentjens, et al., Eradication of systemic B-cell tumors by genetically targeted human T lymphocytes co-stimulated by CD80 and interleukin-15, Nat. Med. (2003); 9: 279-286.
Bruhns et al., Differential Roles of N- and C-Terminal Immunoreceptor Tyrosine-Based Inhibition Motifs During Inhibition of Cell Activation by Killer Cell Inhibitory Receptors, The Journal of Immunology 1999; 162:3168-3175.

Bukczynski et al., Costimulatory ligand 4-1 BBL (CD137L) as an efficient adjuvant of human antiviral cytotoxic T cell responses, Proc. Natl. Acad. Sci. USA, 2004, 101:1291-1296.
Cambier, et al., Antigen and Fc receptor signaling. The awesome power of the immunoreceptor tyrosine-based activation motif (ITAM), J Immunol. (Oct. 1, 1995); 155(7):3281-5.
Camerini, D, et al.,. The T cell activation antigen CD27 is a member of the nerve growth factor/tumor necrosis factor receptor gene family, The Journal of Immunology (1991);3165-3169.
Cameron, B.J., et al., Identification of a Titin-Derived HLA-A1-Presented Peptide as a Cross-Reactive Target for Engineered MAGE A3-Directed T Cells, Sci Transl Med (Aug. 7, 2013); 5(197): 197ra103 (11 pages).
Canfield et al., The Binding Affinity of Human IgG for its High Affinity Fc Receptor is Determined by Multiple Amino Acids in the CH2 Domain and Is Modulated by the Hinge Region, J. Exp. Med. 1991, vol. 173 pp. 1483-1491.
Cannons et al., 4-1BB ligand induces cell division, sustains survival, and enhances effector function of CD4 and CD8 T cells with similar efficacy, J Immunol. Aug. 2001, 167(3): 1313-1324.
Carlens et al. Ex vivo T lymphocyte expansion for retroviral transduction: influence of serum-free media on variations in cell expansion rates and lymphocyte subset distribution. (2000) Exp Hernatol 28(10): 1137-46.
Cartellieri, M. et al., Chimeric antigen receptor-engineered T cells for immunotherapy of cancer, J. Biomedicine and Biotechnology, 2010, Article ID 956304, 13 pages.
Cavalieri et al. Human T lymphocytes transduced by lentiviral vectors in the absence of TCR activation maintain an intact immune competence. (2003) Blood. 102(2): 497-505.
Chalupny et al., T-cell activation molecule 4-1BB binds to extracellular matrix proteins, Proc. Natl. Acad. Sci., USA, 89: 103360-10364 (Nov. 1992).
Chang et al., A Chimeric Receptor with NKG2D Specificity Enhances Natural Killer Cell Activation and Killing of Tumor Cells , Cancer Res 2013;73:1777-1786. Published online Jan. 9, 2013.
Cheadle et al., Chimeric antigen receptors for T-cell based therapy Methods Mol Biol. 2012; 907:645-66.
Chen et al. Fusion protein linkers: property, design and functionality, Adv Drug Deliv Rev.(2013); 65: 1357-1369 (Epub Sep. 29, 2012).
Cho C. Rapid identification of cytokine release syndrome after haploidentical PBSC transplantation and successful therapy with tocilizumab. Bone Marrow Transplant. Dec. 2016;51(12):1620-1621, Epub Sep. 26, 2016.
Cho et al., Macromolecular versus small-molecule therapeutics: drug discovery, development and clinical considerations TIBTECH, vol. 14, May 1996, pp. 153-158.
Cohen et al. Recognition of fresh human tumor by human peripheral blood lymphocytes transduced with a bicistronic retroviral vector encoding a murine anti-p53 TCR (2005) J Immunol. 175:5799-5808.
Colcher, D. et al. In vivo tumor targeting of a recombinant single-chain antigen-binding protein., J. Nat. Cancer Inst. (1990); 82:1191-1197.
Cole et al., The molecular determinants of CD8 co-receptor function , 2012, Immunology, 137, 139-148.
Common Terminology Criteria for Adverse Events (CTCAE), National Cancer Institute Common Toxicity Criteria version 4.03 (NCI-CTCAE v4.03 (2010) (196 pages).
Cooper et al. T-cell clones can be rendered specific for CD19: toward the selective augmentation of the graft-versus-B-lineage leukemia effect (2003) Blood. 101(4): 1637-1644.
Cooper et al., Enhanced antilymphoma efficacy of CD19-redirected influenza MP1—specific CTLs by cotransfer of T cells modified to present influenza MP1, Blood 2005, vol. 105 No. 4 pp. 1622-1631.
Cordaro, T. A et al. Tumor size at the time of adoptive transfer determines whether tumor rejection occurs, Eur. J. Immunol. (2000); 30: 1297-1307.
Croft, M., The role of TNF superfamily members in T-cell function and diseases Nature Reviews, Immunology, vol. 9, Apr. 2009, pp. 271-285.

(56) References Cited

OTHER PUBLICATIONS

Dall, Peter et al., In vivo cervical cancer growth inhibition by genetically engineered cytotoxic T cells. Cancer Immunol. Immunother. (Jan. 2005); 54(1):51-60.
Darcy, P. K. et al., Expression in cytotoxic T lymphocytes of a single-chain anti-carcinoembryonic antigen antibody, Redirected Fas ligand-mediated lysis of colon carcinoma, Eur. J. Immunol. (1998); 28:1663-72.
Davila M. L. et al: Efficacy and toxicity management of 19-28z CAR T cell therapy in B cell acute lymphoblastic leukemia Sci Transl Med. Feb. 19, 2014;6(224):224-25.
Davila Marco L. et al: CD19-Targeted T Cells for Hematologic Malignancies Clinical Experience to Date , Cancer Journal, vol. 21, No. 6, Jan. 1, 2015 (Jan. 1, 2015),pp. 470-474.
Debelouchina et al., A molecular engineering toolbox for the structural biologist Quarterly Reviews of Biophysics, 2017, 50, e7, pp. 1-41.
Diefenbach et al., The innate immune response to tumors and its role in the induction of T-cell immunity, Immunological Reviews 2002, vol. 188: 9-21.
Dotti, et al. Design and development of therapies using chimeric antigen receptor-expressing T cells. Immun Rev (Jan. 2014); 257(1): 107-126.
Dubrovska, A., et al., A chemically induced vaccine strategy for prostate cancer, ACS Chem Biol (2011); 6(11): 1223-31.
Duncan et al., Localization of the binding site for the human high-affinity Fc receptor onlg G, Nature 1998, vol. 332 pp. 563-564.
Ertl, H. C. et al., Considerations for the clinical application of chimeric antigen receptor T cells: observations from a recombinant DNA advisory committee symposium held Jun. 15, 2010, Cancer Res., 2011, 71, 3175-3181.
Eshhar, et al., Design of Cytotoxic T Lymphocytes with Antibody-Type Specificity against Tumor Cells Using Chimeric TcR, Journal of Cellular Biochemistry, Supplement 14B, UCLA Symposia on Molecular & Cellular Biology, Abstracts, 19th Annual Meeting, Jan. 27-Feb. 8, 1990, p. 70.
Eshhar, Z., et al., Functional expression of chimeric receptor genes in human T cells, J. Immunol. Meth. (2001); 248: 67-76.
Fedorov VD, et al., PD-1- and CTLA-4-based inhibitory chimeric antigen receptors (ICARs) divert off—target immunotherapy responses, Sci Transl Med. (Dec. 11, 2013);5(215):215ra172 (12 pages).
Feng et al., Convergence on a Distinctive Assembly Mechanism by Unrelated Families of Activating Immune Receptors , Immunity, vol. 22, 427-438, Apr. 2005.
Feng et al., The Assembly of Diverse Immune Receptors is Focused on a Polar Membrane-Embedded Interaction Site , 2006. PLoS Biol 4(5):e142.
Ferrone, S., et al., How much longer will tumor cells fool the immune system, Immunol. Today (2000); 21: 70-72.
Figini, M, et al., Conversion of murine antibodies to human antibodies and their optimization for ovarian cancer therapy targeted to the folate receptor, Cancer ImmunolImmunother (Apr. 2009); 58(4):531-46 (Epub Aug. 15, 2008).
Foell et al., CD137-mediated T cell co-stimulation terminates existing autoimmune disease in SLE-prone NZB/NZW F1 mice., Ann N Y Acad Sci. Apr. 2003; 987:230-5.
Frecha et al. Advances in the field of lentivector-based transduction of T and B lymphocytes for gene therapy (2010) Molecular Therapy: The Journal of the American Society of Gene Therapy. 18:1748-1757.
Frost et al., In Vitro Evaluation of Avidin Antibody Pretargeting Using 211At-Labeled andBiotinylated Poly-L-Lysine as Effector Molecule*, Cancer 2010, Cancer Therapy With Antibodies and Immunoconjugates, Supplement to Cancer, pp. 1101-1110.
Fujita, K. et al., Prolonged disease-free period in patients with advanced epithelial ovarian cancer after adoptive transfer of tumor-infiltrating lymphocytes. Clin. Cancer Res., 1995, 1, 501-507.
Gargalionis et al., The molecular rationale of Src inhibition in colorectal carcinomas, Int. J.Cancer, 134:2019-2029 (2013).
Gargett, T., et al., GD2-specific CART Cells Undergo Potent Activation and Deletion Following Antigen Encounter but can be Protected From Activation-induced Cell Death by PD-1 Blockade. Mol Ther, 2016. 24(6): p. 1135-49.
Gilboa, E., How tumors escape immune destruction and what we can do about it, Cancer Immunol. Immunother. (1999); 48: 382-385.
Gilham et al., CAR-T cells and solid tumors: tuning T cells to challenge an inveterate foe, Trends in Molecular Medicine (2012); 18(7): 377-384 (Epub May 19, 2012).
Gilham et al., Primary polyclonal human T lymphocytes targeted to carcino-embryonicantigens and neural cell adhesion molecule tumor antigens by CD3zeta-based chimeric immune receptors, J. Immunother, (Mar.-Apr. 2000); 25 (2): 139-151.
Gillies, S.D. et al., Targeting Human Cytotoxic T Lymphocytes to Kill Heterologous Epidermal Growth Factor Receptor-Bearing Tumor Cells, The Journal of Immunology (1991); 146(3): 1067-1071.
Gong, M. C., et al., Prostate-specific membrane antigen (PSMA)-specific monoclonal antibodies in the treatment of prostate and other cancers, Cancer Metastasis Rev. (1999); 18: 483-490.
Gonzalez et al., Genetic engineering of cytolytic T lymphocytes for adoptive T-cell therapy of neuroblastoma, The Journal of Gene Medicine (Jun. 2004) vol. 6, Issue 6, 704-711.
Goverman, J. et al., Chimeric immunoglobulin-T cell receptor proteins form functional receptors: implications for T cell receptor complex formation and activation, Cell (1990); 60:929-939.
Greenfield, E. A, Nguyen, K. A & Kuchroo, V. K. CD28/B7 co-stimulation: a review. Crit. Rev. Immunol. 18, 389-41 8 (1998).
Griffiths et al., The Nature of DNA Modern Genetic Analysis. New York: W.H. Freeman; 1999, pp. 1-11.
Grosenbach et al., A recombinant vector expressing transgenes for four T-cell costimulatory molecules (OX40L, B7-1, ICAM-1, LFA-3) induces sustained CD4+ and CD8+ T-cell activation, protection from apoptosis, and enhanced cytokine production, Cellular Immunology 222 (2003) 45-57.
Gross et al., Development and study of chimeric immunoglobulin/T cell receptor molecules as functional receptors that endow T cells with antibody-type specificity, Ph.D. Thesis presented to the Feinberg Graduate School, The Wiezmann Institute of Science, Rehovot, Israel (1990); 1-70.
Gross, G. et al., Endowing T cells with antibody specific using chimeric T cell receptors, Department of Chemical Immunology, FASEB J. (Dec. 1992); 6(15):3370-8.
Gross, G. et al., Expression of immunoglobuling-T-cell receptor chimeric molecules as functional receptors with antibody-type specificity, Proc. Natl. Acad. Sci., 1989, 86, 10024-10028.
Gross, G. et al., Generation of effector T cells expressing chimeric T cell receptor with antibody type-specificity, Transplant. Proc. (1989); 21 (1 Pt 1):127-130.
Grupp et al., Chimeric Antigen Receptor-Modified T Cells for Acute Lymphoid Leukemia, N. Engl. J. Med. (Apr. 18, 2013) 368(16):1509-1518.
Grupp Stephan A .: Advances in T-cell therapy for All, Best Practice & Research Clinical Haematology, vol. 27, No. 3-4, Sep. 1, 2014(Sep. 1, 2014), pp. 222-228.
Gruss et al., Tumor Necrosis Factor Ligand Superfamily: Involvement in the Pathology of Malignant Lymphomas Blood, vol. 85, No. 12, Jun. 15, 1995, pp. 3378-3404.
Guinn et al., 4-1BBL Cooperates with B7-1 and B7-2 in Converting a B Cell Lymphoma Cell Line into a Long-Lasting Antitumor Vaccine, The Journal of Immunology162:5003-5010 (1999).
Habib-Agahi,H., Phan, T.T. and Searle,P.F. Co-stimulation with 4-1BB ligand allows extended T-cell proliferation, synergizes with CD80/CD86 and can reactivate anergic T cells Int. Immunol. 19 (12), 1383-1394 (2007).
Hackett et al. A transposon and transposase system for human application (2010) Molecular Therapy: The Journal of the American Society of Gene Therapy. 18:674-683.
Hanson, H. L. et al. Eradication of established tumors by CD8+ T cell adoptive immunotherapy. Immunity 13, 265-276 (2000).
Harper et al., CTLA-4 and CD28 Activated Lymphocyte Molecules are Closely Related in Both Mouse and Human as to Sequence,

(56) References Cited

OTHER PUBLICATIONS

Message, Expression, Gene Structure, and Chromosomal Location, The Journal of Immunology, vol. 147, 1037-1044, No. 3, Aug. 1, 1991.
Hatakeyama et al., Transmembrane Signaling of Interleukin 2 Receptor, J. Exp. Med. 1987, vol. 166 pp. 362-375.
Haynes et al., Redirecting Mouse CTL Against Colon Carcinoma: Superior Signaling Efficacy of Single-Chain Variable Domain Chimeras Containing TOR-zeta vs Fcepsilon RI-gamma J Immunol 2001; 166:182-187 (Haynes 2001).
Hege et al., Safety, tumor trafficking and immunogenicity of chimeric antigen receptor (CAR)-T cells specific for TAG-72 in colorectal cancer, Journal for Immunotherapy of Cancer 2017, 5:22.
Hege et al., Systemic T Cell-independent Tumor Immunity after Transplantation of Universal Receptor—modified Bone Marrow into SCID Mice , J. Exp. Med. vol. 184 Dec. 1996 pp. 2261-2269.
Herron, J.N., et al., High resolution structures of the Apr. 4, 20 Fab-fluorescein complex in two solvent systems: effects of solvent on structure and antigen-binding affinity . Biophys J, 1994. 67(6): p. 2167-83.
Heuser, et al., T-cell activation by recombinant immunoreceptors: impact of the intracellular signalling domain on the stability of receptor expression and antigen-specific activation of grafted T-cells, Gene Therapy (2003); 10: 1408-1419.
Hombach et al., T cell activation by recombinant FcɛRl γ-chain immune receptors: an extracellular spacer domain impairs antigen-dependent T cell activation but not antigen recognition, Gene Therapy (2000) 7, 1067-1075.
Hombach, et al., Adoptive Immunotherapy with Genetically Engineered T Cells: Modification of the IgG1 Fc 'Spacer' Domain in the Extracellular Molety of Chimeric Antigen Receptors Avoids 'Off-Target' Activation and Unintended Initiation of an Innate Immune Response, Gene Ther. (Oct. 2010); 17(10):1206-13.
Honegger et al., A mutation designed to alter crystal packing permits structural analysis of a tight-binding fluorescein-scFv complex, Protein Science (2005) 14(10), 2537-2549.
Huang, J., et al., Modulation by IL-2 of CD70 and CD27 expression on CD8+ T cells: importance for the therapeutic effectiveness of cell transfer immunotherapy J. Immunol. 176 (12), 7726-7735 (2006).
Hughes M. S. et al., Transfer of a TCR gene derived from a patient with a marked antitumor response conveys highly active T-cell effector functions. Hum Gene Ther Apr. 2005; 16(4):457-72.
Hunter et al., Inhibition of Fcγ Receptor-Mediated Phagocytosis by a Nonphagocytic FcγReceptor, Blood, vol. 91, No. 5 Mar. 1, 1998: pp. 1762-1768.
Hutchins, B. et al., Site-specific coupling and sterically controlled formation of multimeric antibody fab fragments with unnatural amino acids, J. Mol. Biol., 2011, 406, 595-603.
Hutloff, A. et al., ICOS is an inducible T-cell costimulator structurally and functionally related to CD28. Nature, 1999, 397, 263-266.
Hwu, et al., The Genetic Modification of T Cells for Cancer Therapy: An Overview of Laboratory and Clinical Trials, Cancer Detection and Prevention (1994); 18(1):43-50.
Imai, C. et al., Chimeric receptors with 4-1BB signaling capacity provoke potent cytotoxicity against acute lymphoblastic leukemia, Leukemia, 2004, 18, 676-684.
Imai, K., et al., Comparing Antibody and Small-Molecule Therapies for Cancer ; https://www.medscape.com/viewarticle/550008 (26 pages).
Irving, B. A., et al., The cytoplasmic domain of the T cell receptor zeta chain is sufficient to couple to receptor-associated signal transduction pathways' Cell (1991); 64:891-901.
Isakov et al., PKC-theta-mediated signal delivery from the TCR/CD28 surface receptors , Frontiers in Immunology, T Cell Biology, Aug. 2012, vol. 3, Article 273, pp. 1-12.
Janeway et al., Appendix I. Immunologists' Toolbox Immunobiology: The Immune System in Health and Disease. 5th ed. New York: Garland Science; 2001 (101 pages).
Janeway et al., The structure of a typical antibody molecule Immunobiology: The Immune System in Health and Disease. 5th Ed. New York: Garland Science; 2001, pp. 1-11.
Jang, I, et al., Human 4-1BB (CD137) Signals Are Mediated by TRAF2 and Activate Nuclear Factor-kB, Biochemical and Biophysical Research Communications (1998);613-620.
Jena et al., Redirecting T-cell specificity by introducing a tumor-specific chimeric antigen Receptor, Blood 2010, vol. 116, No. 7, pp. 1035-1044.
Jensen, M. et al. CD20 is a Molecular Target For scFvFc[zeta] Receptor Redirected T Cells: Implications for Cellular Immunotherapy of CD20+ Malignancy, Biology of Blood and Marrow Transplantation (1998); 4:75-83.
Jensen, M. C., et al., Abstract #98: Targeting Pre-B Acute Lymphoblastic Leukemia With T Cell Clones Engineered To Express A CD19-Specific Chimeric Immunoreceptor, Blood (Nov. 16, 2000); 96(11):26A.
Jensen, M.C., et al., Antitransgene rejection responses contribute to attenuated persistence of adoptively transferred CD20/CD19-specific chimeric antigen receptor redirected T cells in humans. Biol Blood Marrow Transplant, 2010. 16(9): p. 1245-56.
Jonnalagadda et al., Chimeric Antigen Receptors With Mutated IgG4 Fc Spacer Avoid Fc Receptor Binding and Improve T Cell Persistence and Antitumor Efficacy, Molecular Therapy 2015, vol. 23, No. 4, pp. 757-768.
Jung et al., Improving in vivo folding and stability of a single-chain Fv antibody fragment by loop grafting, Protein Engineering (1997) vol. 10, No. 8, pp. 956-966.
Jung, S. et al., Selection for improved protein stability by phage display, J. Mol. Biol., 1999, 294, 163-180.
Kagoya, Y., et al., Transient stimulation expands superior antitumor T cells for adoptive therapy. JCI Insight, 2017. 2(2): p. e89580 (13 pages).
Kalos et al., T Cells with Chimeric Antigen Receptors Have Potent Antitumor Effects and Can Establish Memory in Patients with Advanced Leukemia, Sci. Transl. Med. (Aug. 10, 2011) 3(95):1-21.
Kandalaft, L. et al., A phase I clinical trial of adoptive transfer of folate receptor-alpha redirected autologous T cells for recurrent ovarian cancer, Journal of Translational Medicine, 2012, 10:157, 10 pages.
Kang, S. et al: Therapeutic uses of anti-interleukin-6 receptor antibody, International Immunology, vol. 27, No. 1, Aug. 20, 2014 (Aug. 20, 2014), pp. 21-29.
Karachaliou et al., Common Co-activation of AXL and CDCP1 in EGFR-mutation-positive Non-small cell Lung Cancer Associated with Poor Prognosis, EBioMedicine (2017) https://doi.org/10/1016/j.ebiom.2018.02.001.
Kariv et al., Analysis of the Site of Interaction of CD28 with Its Counterreceptors CD80 and CD86 and Correlation with Function, 157 J. Immunol.29-38 (1996).
Katz et al., Recognition of HLA-Cw4 but Not HLA-Cw6 by the NK Cell Receptor Killer Celllg-Like Receptor Two-Domain Short Tail No. 4 , J Immunol 2001; 166:7260-7267.
Kennedy, M. et al., Optical imaging of metastatic tumors using a folate-targeted fluorescent probe, J. Biomed. Opt., 2003, 8, 636-641.
Kim el al. Redirection of Genetically Engineered CAR•T Cells Using Bifunctional Small Molecules, Journal of the American Chemical Society (Feb. 18, 2015) vol. 137, No. 8, pp. 2832-2835, with 8 page supporting document.
Kim et al., NMR Structural Studies of Interactions of a Small, Nonpeptidyl Tpo Mimic with the Thrombopoietin Receptor Extracellular Juxtamembrane and Transmembrane Domains, J Biol Chem (2007) 282(19):14253-14261.
Kim et al., Protein conjugation with genetically encoded unnatural amino acids, Curr OpinChem Biol (2013); 17:412-419 (Epub May 9, 2013).
Kim et al., Therapeutic Potential of 4-1BB (CD137) As a Regulator for Effector CD8+ T Cells, Journal of Hematotherapy & Stem Cell Research (2001) 10:441-449.
Kintzing et al., Emerging Strategies for Developing Next-Generation Protein Therapeutics for Cancer Treatment Trends in Pharmacological Sciences, vol. 37, No. 12, Dec. 2016, pp. 993-1008.

(56) References Cited

OTHER PUBLICATIONS

Klotz et al., Macromolecule-Small Molecule Interactions. Strong Binding by Intramolecularly Cross-Linked Polylysine Biochemistry. vol. 10, No. 6, Mar. 16, 1971, pp. 923-926.
Kochenderfer et al., Construction and pre-clinical evaluation of an anti-CD19 chimeric antigen receptor, Journal of Immunotherapy (2009); 32(7): 689-702.
Kochenderfer et al., Treating B-cell cancer with T cells expressing anti-CD19chimeric antigen receptors 2013, Nature Reviews Clinical Oncology, 10, 267-276 (2013).
Kochenderfer, J. et al., Eradication of B-lineage cells and regression of lymphoma in a patient treated with autologous T cells genetically engineered to recognize CD19, Blood, 2010, 116, 4099-4102.
Kochenderfer, J. et al., B-cell depletion and remissions of malignancy along with cytokine-associated toxicity in a clinical trial of anti-CD19 chimeric-antigen-receptor-transduced T cells, Blood, 2012, 119, 2709-2720.
Kolmar, H. et al., Alternative binding proteins: biological activity and therapeutic potential of cystine-knot miniproteins, The FEBS Journal, 2008, 275, 26684-26690.
Kranz et al., Partial elucidation of an anti-hapten repertoire in BALB/c mice: comparative characterization of several monoclonal antiFLuorescyl antibodies, Mol Immunol (1981) 18(10), 889-898.
Krause, A., et al., Genetic approaches to sustain the function of tumor-specific T-lymphocytes, Mol. Ther. (2000); 1 (S260): 713.
Kularatne, S.A. et al., Prostate-specific membrane antigen targeted imaging and therapy of prostate cancer using a PSMA Inhibitor as a homing ligand, Mol. Pharm., 2009, 6,780-789.
Kuwana, Y. et al., Expression of chimeric receptor composed of immunoglobulin-derived V regions and T-cell receptor-derived C regions, Biochem. Biophys. Res. Comm. (1987); 149:960-968.
Kwon, B, et al., cDNA sequences of two inducible T-cell genes, cDNA sequences of two inducible T-cell genes (1989); 86: 1963-1967.
Kwon, B, et al., Expression Characteristics of Two Potential T Cell Mediator Genes, Cellular Immunology (1989): 414-422.
Lafage-Pochitaloff M, Costello R, Couez D, Simonetti J, Mannoni P, Mawas C, Olive D. Human CD28 and CTLA-4 lg superfamily genes are located at bands q33-q34 Immunogenetics 1190;31(3):198-201.
Lamers et al., Immune responses to transgene and retroviral vector in patients treated withex vivo-engineered T cells, Blood (2011) 117(1): 72-82.
Lamers, C. et al., Treatment of Metastatic Renal Cell Carcinoma With Autologous T-Lymphocytes Genetically Retargeted Against Carbonic Anhydrase IX: First Clinical Experience, J. Clin. Oncol., 2006, 24, e20-22.
Laroche et al., Characterization of a Recombinant Single-chain Molecule Comprising the Variable Domains of a Monoclonal Antibody Specific for Human Fibrin Fragment D-dimer*, The Journal of Biological Chemistry 1991, vol. 266, No. 25, Issue of Sep. 5, pp. 16343-16349.
Latza, U. et al., The human OX40 homolog: cDNA structure, expression and chromosomal assignment of the ACT35 antigen, Eur. J. Immunol., 1994, 24, 677-683.
Lee et al., Current concepts in the diagnosis and management of cytokine release syndrome Blood. Jul. 10, 2014;124(2):188-95. doi: 10.1182/blood-2014-05-552729. Epub May 29, 2014, with errata.
Lee, D, et al., 4-1BB Signaling Activates the T Cell Factor 1 Effector/b-Catenin Pathway with Delayed Kinetics via ERK Signaling and Delayed PI3K/AKT Activation to Promote the Proliferation of CD8+ T Cells, PLOS One (2013); 8: 1-11.
Liebowitz, D. N., Lee, K. P. & June, C. H. Co-stimulatory approaches to adoptive immunotherapy. Curr. Opin. Oncol. 10, 533-541 (1998).
Lin et al., Transglutaminase-catalyzed site-specific conjugation of small-molecule probes to proteins in vitro and on the surface of living cells, J. Am. Chem. Soc. (2006); 128:4542-4543.
Linenberger, CD33-directed therapy with gemtuzumab ozogamicin in acute myeloid leukemia: progress in understanding cytotoxicity and potential mechanisms of drug resistance , Leukemia (2005) 19, 176-182.
Liou et al., A chimeric mouse-human antibody that retains specificity for HIV gp 120 and mediates the lysis of HIV-infected cells, J Immunol 1989; 143: 3967-3975.
Lodish et al., Hierarchical Structure of Proteins Molecular Cell Biology. 4th Ed. New York: W.H. Freeman; 2000. pp. 1-25.
Long, A.H., et al., 4-IBB costimulation ameliorates T cell exhaustion induced by tonic signaling of chimeric antigen receptors. Nat Med, 2015. 21(6): p. 581-90.
Love et al., ITAM-mediated Signaling by the T-Cell Antigen Receptor , Cold Spring HarbPerspect Biol 2010;2:a002485.
Lowin-Kropf et al., Cytoskeletal Polarization of T Cells is Regulated by an Immunoreceptor Tyrosine-based Activation Motif—dependent Mechanism, The Journal of Cell Biology 1998, vol. 140, No. 4, pp. 861-871.
Lu, Y. et al., Folate-targeted dinitrophenyl hapten immunotherapy: effect of linkerchemistry on antitumor activity and allergic potential, Mol. Pharm., 2007, 695-706.
Lu, Y. et al., Preclinical pharmacokinetics, tissue distribution, and antitumor activity of afolate-hapten conjugate-targeted immunotheraphy in hapten-immunized mice, Molecular Cancer Therapeutics, 2006, 5, 3258-3267.
Lueders et al., The Long Terminal Repeat of an Endogenous Intracisternal A—ParticleGene Functions as a Promoter When Introduced into Eucaryotic Cells by Transfection Molecular and Cellular Biology, vol. 4, No. 10, Oct. 1984, pp. 2128-2135.
Lustgarten, J., et al., Specific Elimination of IgE Production Using T Cell Lines Expressing Chimeric T Cell Receptor Genes, European Journal of Immunology (1995); 25(10):2985-2991.
Ma et al., Versatile strategy for controlling the specificity and activity of engineered T cells, Proc. Nat. Acad. Sci. U.S.A (Jan. 12, 2016) vol. 113, No. 4, pp. 450-458.
Ma, Q. et al., Carcinoembryonic antigen-immunoglobulin Fc fusion protein (CEA-Fc) for identification and activation of anti-CEA immunoglobulin-T-cell receptor-modified T cells, representative of a new class of lg fusion proteins, Cancer Gene Therapy (2004); 11: 297-306.
Ma, Q., et al., Genetically engineered T cells as adoptive immunotherapy of cancer, Cancer Chemother Biol Response Modif (2002); 20: 315-41.
Maeda et al., Tumor vascular permeability and the EPR effect in macromolecular therapeutics: a review, Journal of Controlled Release 65 (2000), pp. 271-284 (14 pages).
Maher, et al., Human T-lymphocyte cytotoxicity and proliferation directed by a single chimeric TCRzeta/CD28 receptor, Nature Biotechnology (2002); 20: 70-75.
Marincola, F. M., et al., Escape of human solid tumors from T cell recognition: molecular mechanisms and functional significance, Adv. Immunol. (2000); 74: 181-273.
Maude Shannon L. et al. Chimeric Antigen Receptor T Cells for Sustained Remissions in Leukemia N Engl J Med. Oct. 16, 2014;371(16):1507-17.
Maude Shannon L. et al. Managing Cytokine Release Syndrome Associated With Novel T Cell-Engaging Therapies Cancer J. Mar.-Apr. 2014;20(2):119-22.
Maus et al., Ex vivo expansion of polyclonal and antigen-specific cytotoxic T lymphocytes by artificial APCs expressing ligands for the T-cell receptor, CD28 and 4-1BB, Nature Biotechnology, Nature Publishing Group, New York, NY, US, vol. 20, No. 2, Feb. 1, 2002, pp. 143-148.
Maus, M.V., et al., T cells expressing chimeric antigen receptors can cause anaphylaxis in humans. Cancer Immunol Res, 2013. 1(1): p. 26-31.
Mcguinness RP, et al., Anti-tumor activity of human T cells expressing the CC49-zeta chimeric immune receptor, Hum Gene Ther. (Jan. 20, 1999); 10(2):165-73.
Medstrand et al., Long Terminal Repeats Are Used as Alternative Promoters for the Endothelin B Receptor and Apolipoprotein C-I Genes in Humans , The Journal of Biological Chemistry, vol. 276, No. 3, Issue of Jan. 19, pp. 1896-1903, 2001.

(56) References Cited

OTHER PUBLICATIONS

Melero, I, et al., Amplification of tumor immunity by gene transfer of the co-stimulatory 4-1BB ligand: synergy with the CD28 co-stimulatory pathway, Bristol-Myers Squibb Pharmaceutical Research Institute (1998); 1116-1121.
Melief, C. J. et al., Strategies for immunotherapy of cancer, Adv. Immunol. (2000); 75:235-282.
Mooney et al., Concise Review: Neural Stem Cell-Mediated Targeted Cancer Therapies Stem Cells Translational Medicine, 2018, pp. 740-747.
Moore et al., Characterisation of salmon and trout CD8α and CD8β, Molecular Immunology 42 (2005) 1225-1234.
Moretta et al., Activating Receptors and Coreceptors Involved in Human Natural Killer Cell-Mediated Cytolysis, Annu. Rev. Immunol. 2001. 19:197-223.
Morgan RA, et al., Cancer regression in patients after transfer of genetically engineered lymphocytes, Science (Oct. 6, 2006); 314(5796): 126-9.
Morrison, C, CAR-T Field Booms as Next-Generation Platforms Attract Big Players, Nature Biotechnology (Jun. 2015); 33: 571-72.
Muller T, et al., Expression of a CD20-specific chimeric antigen receptor enhances cytotoxic activity of NK cells and overcomes NK-resistance of lymphoma and leukemia cells, Cancer Immunol. Immunother. (2008); 57: 411-423.
Mungra et al., Targeted human cytolytic fusion proteins at the cutting edge: harnessing the apoptosis-inducing properties of human enzymes for the selective elimination of tumor cells Oncotarget, vol. 10, No. 8, 2019, pp. 897-915.
Munn et al., Role of Low-Affinity Fc Receptors in Antibody-dependent Tumor Cell Phagocytosis by Human Monocyte-derived Macrophages, Cancer Research 51, 1117-1123, Feb. 15, 1991.
Nam, K, et al., Cross-Linking of 4-1BB Activates TCR-Signaling Pathways in CD8 T Lymphocytes1, The Journal of Immunology; 1898-1905.
National Cancer Institute. CAR T-Cell Therapy: Engineering Patients' Immune Cells to Treat Their Cancers, Cancer Research Updates, Updated: Oct. 16, 2014; 5 pages; retrieved Nov. 17, 2014 fromhttp://www.cancer.gov/cancertopics/research-updates/2013/CAR-T-Cells.
Nelson, Aaron L., Antibody fragments, mAbs 2010, Landes Bioscience, vol. 2, Issue 1, pp. 77-83.
Nieba, L. et al., Disrupting the hydrophobic patches at the antibody variable/constant domain interface: improved in vivo folding and physical characterization of an engineered scFv fragment, Protein Eng., 1997, 10, 435-444.
Oelke et al., Ex vivo induction and expansion of antigen-specific cytotoxic T cells by HLA-Ig-coated artificial antigen-presenting cells, Nature Medicine (2003); 9(5):619-624.
Oelsner, S., et al., Continuously expanding CAR NK-92 cells display selective cytotoxicity against B-cell leukemia and lymphoma , Cytotherapy, 2017; 19: 235-249.
Okazaki et al., PD-1 immunoreceptor inhibits B cell receptor mediated signaling by recruiting src homology2-domain-containing tyrosine phosphatase 2 to phosphotyrosine , PNAS Nov. 20, 2001, vol. 98, No. 24, 13866-13871.
Orr, B. et al., Rapid method for measuring ScFv thermal stability by yeast surface display, Biotechnol Prog., 2003. 19, 631-638.
Pages et al., Two Distinct Intracytoplasmic Regions of the T-cell Adhesion Molecule CD28 Participate in Phosphatidylinositol 3-Kinase Association The Journal of Biological Chemistry, vol. 271, No. 16, Apr. 19, 1996, pp. 9403-9409.
Paillard, F. Immunotherapy with T cells bearing chimeric antitumor receptors, Hum. Gene Ther. (1999); 10: 151-153.
Paillasse, M, et al., Insights into the Cholecystokinin 2 Receptor Binding Site and Processes of Activation, The American Society for Pharmacology and Experimental Therapeutics (2006); 70:1935-1945.
Pameijer, C.R., et al., Conversion of a tumor-binding peptide identified by phage display to a functional chimeric T cell antigen receptor, Cancer Gene Ther., 2007, 14, 91-07.
Park et al., Treating cancer with genetically engineered T cells Trends Biotechnol. Nov. 29, 2011(11): 550-557.
Parkhurst et al. Characterization of genetically modified T-cell receptors that recognize the CEA:691-699 peptide in the context of HLA-A2.1 on human colorectal cancer cells (2009) Clin Cancer Res. Jan. 1, 2009;15(1):169-80.
Patel Jaina M et al: Cancer CARtography: charting out a new approach to cancer immunotherapy, Immunotherapy. 2014;6(6):675-8.
Pollock et al., Inducible T cell antigen 4-1BB. Analysis of expression and function, J Immunol 1993; 150:771-781.
Porter DL, et al. Chimeric antigen receptor T cells persist and induce sustained remissions in relapsed refractory chronic lymphocytic leukemia . Science translational medicine. 2015;7(303):303-39. doi: 10. I 126/scitransimed.aac5415. PubMed PMID:26333935.
Porter, D.L. et al., Chimeric antigen receptor-modified T cells in chronic lymphoid leukemia, N. Engl. J. Med., 2011, 365, 725-733.
Prasad et al., T-cell antigen CD28 interacts with the lipid kinase phosphatidylinositol3-kinase by a cytoplasmic Tyr(P)-Met-Xaa-Met motif, Proc. Natl. Acad. Sci. USA, vol. 91, pp. 2834-2838, Mar. 1994.
Product brochure for the Engineered Autologous Cell Therapy (eACT™) Platform, available from Kite Pharma, retrieved Oct. 25, 2015 from http://www.kitepharma.com/c/products/eact.php.
Pule et al., Artificial T-cell receptors, Cytotherapy (2003) 5(3):211-226.
Pule et al., Virus-specific T cells engineered to coexpress tumor-specific receptors: persistence and antitumor activity in individuals with neuroblastoma, Nat. Med. (2008); 14: 1264-1270.
Qin et al., Incorporation of a hinge domain improves the expansion of chimeric antigen receptor T cells, Journal of Hematology & Oncology (2017) 10:68.
Rai et al., Expression systems for production of heterologous proteins, Current Science2001, vol. 80, No. 9, pp. 1121-1128.
Recent patent applications in chimeric antigen receptors, *Nature Biotechnology* 32(3): 239 (2014).
Reddy et al., Elimination of Fc Receptor-Dependent Effector Functions of a Modified IgG4Monoclonal Antibody to Human CD4, J Immunol 2000; 164: 1925-1933.
Redmond et al., The role of OX40-mediated co-stimulation in T cell activation and survival, Crit. Rev. Immunol. 2009, 29(3): 187-201.
Reichert, J. Day 1, Emerging Disruptive Technologies and Cutting-Edge Analytical Techniques, MAbs, 2009, 1, 190-209.
Restifo et al., Adoptive immunotherapy for cancer: harnessing the T cell response, Nat. Rev. Immunol. (Mar. 22, 2012) 12(4):269-281.
Reubi, Jean Claude, Peptide Receptors as Molecular Targets for Cancer Diagnosis and Therapy, Endocrine Reviews 24(4): 389-427.
Riha et al., CD28 co-signaling in the adaptive immune response Self/Nonself 1:3,231-240; Jul./Aug./Sep. 2010.
Riley et al., The CD28 family: a T-cell rheostat for therapeutic control of T-cell activation, Blood, Jan. 1, 2005, vol. 105, No. 1, pp. 13-21.
Riviere, I., Gallardo, H. F., Hagani, A B. & Sadelain, M. Retroviral-mediated gene transfer in primary murine and human T-lymphocytes. Mol. Biotechnol. 15, 133-142 (2000).
Roberts et al., Chemistry for peptide and protein PEGylation, Advanced Drug Delivery Reviews (2002); 54:459-476.
Rodgers, D. et al., Switch-mediated activation and retargeting of CAR-T cells for B-cell malignancies, Proc. Natl. Acad. Sci., 2016, 113, E459-468.
Romeo, C. at al., Sequence requirements for induction of cytolysis by the T cell antigen/Fc receptor zeta chain, Cell (1992); 68:889-897.
Romeo, C., et al., Cellular immunity to HIV activated by CD4 fused to T cell or Fc receptor polypeptides, Cell (1991); 64:1037-1046.
Rosenberg Cell transfer immunotherapy for metastatic solid cancer—what clinicians need to know (2011) Nat Rev Clin Oncol. 8(10):577-85).
Rosenberg et al. Adoptive cell transfer: a clinical path to effective cancer immunotherapy. Nat Rev Cancer. Apr. 2008; 8(4):299-308.
Rosenberg, S. A. et al., Adoptive cell therapy for the treatment of patients with metastatic melanoma, Current Opinion in Immunology, 2009, 21, 233-240.

(56) References Cited

OTHER PUBLICATIONS

Rotz Seth J. et al. Severe cytokine release syndrome in a patient receivingPD-1-directed therapy Pediatr Blood Cancer. Dec. 2017;64(12). Epub May 24, 2017 (4 pages).
Rueckert S, et al., A monoclonal antibody as an effective therapeutic agent in breast cancer: trastuzumab Expert Opin Biol Ther. Jun. 2005;5(6):853-66.
Sadelain et al., Targeting Tumours with Genetically Enhanced T Lymphocytes, Nat Rev Cancer (Jan. 2003): 3(1): 35-45.
Sadelain, et al., The promise and potential pitfalls of chimeric antigen receptors, Current Opinion in Immunology (2009): 21: 215-223.
Sadelain, M. et al., The basic principles of chimeric antigen receptor design, Cancer Discov., 2013, 3, 388-398.
Saoulli, C, et al., CD28-Independent, TRAF2-dependent Costimulation of Resting T Cells by 4-1BB Ligand, Master of Science Thesis, Department of Immunology University of Toronto (1998), 77 pp.
Saraswat et al., DNA as Therapeutics; an Update, Indian J Pharm Sci. Sep.-Oct. 2009;71(5): 488-498.
Scholler, J., et al., Decade-long safety and function of retroviral-modified chimeric antigen receptor T cells, Sci Transl Med (May 2, 2012); 4(132): 132ra53 (7 pages).
Schonfeld, K, et al., Selective Inhibition of Tumor Growth by Clonal NK Cells Expressing an Erb82/HER2-Specific Chimeric Antigen Receptor , Mol. Ther., vol. 23 No. 2, 330-338 Feb. 2015.
Schreiber, S.L., Organic synthesis toward small-molecule probes and drugs PNAS, vol. 108, No. 17, Apr. 26, 2011, pp. 6699-6702.
Schwesinger et al., Unbinding forces of single antibody-antigen complexes correlate with their thermal dissociation rates, PNAS (2000) 97(18), 9972-9977.
Scott, D., et al., Immunogenicity of biotinylated hapten-avidin complexes, Mol Immunol(1984); 21(11): 1055-60.
Sega, E. et al., Tumor detection using folate receptor-targeted imaging agents, Cancer Metastasis Rev., 2008, 27, 655-664.
Sentman Challenges of creating effective chimeric antigen receptors for cancer therapy Immunotherapy. Aug. 2013;5(8):783-5.
Serghides et al., Evaluation of OX40 Ligand as a Costimulator of Human Antiviral Memory CD8 T Cell Responses: Comparison with B7.1 and 4-1BBL, The Journal of Immunology 175:6368-6377 (2005).
Shields et al., High Resolution Mapping of the Binding Site on Human IgG1 for FcγRI, FcγRII, FcγRIII, and FcRn and Design of IgG1 Variants with Improved Binding to the FcγR*, The Journal of Biological Chemistry 2001, vol. 276, No. 9, Issue of Mar. 2, pp. 6591-6604.
Shirasu, N. et al., Construction and Molecular Characterization of Human Chimeric T-Cell Antigen Receptors Specific for Carcinoembryonic Antigen, Anticancer Research (2010); 30:2731-2738.
Sobota et al., Binding of IgG-Opsonized Particles to FcγR Is an Active Stage of Phagocytosis That Involves Receptor Clustering and Phosphorylation, The Journal of Immunology 2005; 175:4450-4457.
Stancovski et al., Targeting of T Lymphocytes to Neu/HER2-Expressing Cells Using Chimeric Single Chain Fv Receptors, J. Immunol. (1993); 151(11):6577-6582.
Stein, P, et al., The Cytoplasmic Domain of CD28 Is both Necessary and Sufficient for Costimulation of Interleukin-2 Secretion and Association with Phosphatidylinositol3'-Kinase, American Society for Microbiology (1994); 14: 3392-3402.
Stephan et al., T cell-encoded CD80 and 4-1BBL induce auto- and transcostimulation, resulting in potent tumor rejection, Nature Medicine (Dec. 2007); 13(12): 1440-1449.
Stevens et al., Generation of Tumor-Specific CTLs from Melanoma Patients by Using Peripheral Blood Stimulated with Allogeneic Melanoma Tumor Cell Lines, J. Immunol(1995); 154:762-771.
Suhoski, M.M., et al., Engineering artificial antigen-presenting cells to express a diverse array of co-stimulatory molecules. Mol Ther, 2007. 15(5): p. 981-8.

Swanson et al., The coordination of signaling during Fc receptor-mediated phagocytosis, Journal of Leukocyte Biology, vol. 76, Dec. 2004, pp. 1093-1103.
Tam et al., Functional, Biophysical, and Structural Characterization of Human IgG1 andIgG4 Fc Variants with Ablated Immune Functionality, Antibodies 2017, 6, 12.
Tamada et al. Redirecting Gene-Modified T Cells toward Various Cancer Types Using Tagged Antibodies, Clinical Cancer Research (Oct. 2, 2012) vol. 18, Iss. 23, pp. 6436-6445, with correction.
Tanaka, Toshio et al. Immunotherapeutic implications of IL-6 blockade for cytokine storm. Immunotherapy. Jul. 2016;8(8):959-70.
Teachey D. T. et al. Cytokine release syndrome after blinatumomab treatment related to abnormal macrophage activation and ameliorated with cytokine-directed therapy Blood. Jun. 27, 2013;121(26):5154-7. doi: 10.1182/blood-2013-02-485623. Epub May 15, 2013.
Themeli, M., et al., Generation of tumor-targeted human T lymphocytes from induced pluripotent stem cells for cancer therapy, Nat Biotechnol (2013); 31(10):928-33 (Epub Aug. 11, 2013).
Tsukahara et al. CD19 target-engineered T-cells accumulate at tumor lesions in human B-cell lymphoma xenograft mouse models (2013) Biochem Biophys Res Commun 438(1): 84-9. Epub Jul. 17, 2013.
Tumor necrosis factor receptor superfamily, HUGO Gene Nomenclature Committee, 2 pp.
Turatti, F., et al., Redirected activity of human antitumor chimeric immune receptors is governed by antigen and receptor expression levels and affinity of interaction, J Immunother (2007); 30(7): 684-93.
Turtle et al., Engineered T cells for anti-cancer therapy Curr. Opin. Immunol., Oct. 2012; 24(5): 633-39. Epub Jul. 18, 2012.
Uherek, C, et al., Chimeric antigen receptors for the retargeting of cytotoxic effector cells, J. Hematother. Stem Cell Res. (2001); 10: 523-534.
UniProtKB—O43914, TYRO protein tyrosine kinase-binding protein , pp. 1-15.
UniProtKB—P01732 (CD8A_HUMAN). T-cell surface glycoprotein CD8 alpha chain; 11pages; retrieved on May 13, 2016 from http://www.uniprot.org/uniprot/P01732.
UniProtKB—P02701, AVidin Precursor—Gallus Chicken.
UniProtKB—P10747 (CD28_HUMAN).
UniProtKB—P10966 (CD8B_HUMAN).
UniProtKB—P20963 (CD3Z_HUMAN). T-cell surface glycoprotein CD3 zeta chain; 12pages; retrieved on May 13, 2016 from http://www.uniprot.org/uniprot/P20963.
UniProtKB—Q07011 (TNR9_HUMAN). Tumor necrosis factor receptor superfamily member 9: 14 pages; retrieved on May 13, 2016 from http://www.uniprot.org/uniprot/Q07011.
Urba, W.J. et al., Redirecting T cells, New Engl. J. Med., 2011, 365, 754-757.
Urbanska et al., A Universal Strategy for Adoptive Immunotherapy of Cancer through Use of a Novel T-cell Antigen Receptor, Cancer Research (2012) 72(7): 1844-1852.
Urbanska, K., et al., A Universal Immune Receptor Expressed by T Cells for the Targeting of Diverse and Multiple Tumor Associated Antigens IN Abstracts for the 26th Annual Scientific Meeting of the Society for Immunotherapy of Cancer (SITC), J Immunother, vol. 34, No. 9, Nov.-Dec. 2011 (62 pages), p. 381.
Uttenthal, B.J., et al., Challenges in T cell receptor gene therapy. J Gene Med (Jun. 2012); 14(6): 386-99.
Van Blitterswijk et al., Anticancer mechanisms and clinical application of alkylphopholipids, Biochimica et Biophysica Acta (2013) 1831(3):663-674.
Van Dam, G. et al., Intraoperative tumor-specific fluorescence imaging in ovarian cancer by folate receptor-α targeting: first in-human results, Nature Medicine, 2011, 17, 1315-1319.
Van der Luit et al., A new class of anticancer alkylphospholipids uses lipid rafts as membrane gateways to induce apoptosis in lymphoma cells, Mol Cancer Ther (2007) 6(8):2337-2345.
Van Rhijn et al., Nov. 30, 2015, Human autoreactive T cells recognize CD1b and phospholipids. Proceedings of the National Academy of Sciences 113(2):380-385.

(56) References Cited

OTHER PUBLICATIONS

Vaughan et al., Human antibodies with sub-nanomolar affinitis isolate from a large non-immunized phage display library, Nature Biotechnology (1996) vol. 14(3), pp. 309-314.
Verdine et al., The Challenge of Drugging Undruggable Targets in Cancer: Lessons Learned from Targeting BCL-2 Family Members Clin. Cancer Res. vol. 13, No. 24, Dec. 15, 2007, pp. 7264-7270.
Verhoeven et al. Lentiviral vector gene transfer into human T cells (2009) Methods Mol Biol. 506: 97-114.
Wang et al. Phenotypic and functional attributes of lentivirus-modified CD19-specific human CD8+ central memory T cells manufactured at clinical scale (2012) J Immunother.35(9):689-701.
Wang et al., Current status and perspectives of chimeric antigen receptor modified T cells for cancer treatment, Protein Cell 2017, 8(12):896-925.
Wayua, C. et al., Evaluation of a Cholecystokinin 2 Receptor—Targeted Near-Infrared Dye for Fluorescence—Guided Surgery of Cancer, Molecular Pharmaceutics, 2014, 11,468-476.
Weijtens, M. E. et al., Single chain Ig/gamma gene-redirected human T lymphocytes produce cytokines, specifically lyse tumor cells, and recycle lytic capacity., J. Immunol.(Jul. 15, 1996); 157(2):836-43.
Weissman et al., Molecular cloning and chromosomal localization of the human T-cell receptor zeta chain: Distinction from the molecular CD3 complex Proc. Natl. Acad. Sci. vol. 85, Dec. 1988, pp. 9709-9713.
Weissman et al., Role of the zeta chain in the expression of the T cell antigen receptor: genetic reconstitution studies The EMBO Journal, vol. 8, No. 12, 1989, pp. 3651-3656.
Wen, T, et al., 4-1BB Ligand-Mediated Costimulation of Human T Cells Induces CD4 andCD8 T Cell Expansion, Cytokine Production, and the Development of Cytolytic Effector Function1, 4897-4906.
Wesolowski, J, et al., Single domain antibodies: promising experimental and therapeutic tools in infection and immunity, Med Microbiol Immunol (2009) 198:157-174.
Wilkie et al., Retargeting of Human T Cells to Tumor-Associated MUC1: The Evolution of a Chimeric Antigen Receptor, The Journal of Immunology Apr. 2008, pp. 4901-4909.
Wilson, et al. DAP12 and KAP10 (DAP10)-novel transmembrane adapter proteins of the CD3zeta family, Immunol Res. (2000); 22(1):21-42.
Wu et al., Remote control of therapeutic T cells through a small molecule-gated chimeric receptor, Science (2015) vol. 350, Issue 6258, pp. 293 and aab4077-aab4077.
Wu et al., Adoptive T-cell therapy using An A tumor-infiltrating lymphocytes for metastatic melanoma: current status and future outlook Cancer, Mar. 18, 2012(2): 160-75.
Wu, et al., An activating immunoreceptor complex formed by NKG2D and DAP10, Science (1999); 285:730-732.
Xu et al., Cytokine release syndrome in cancer immunotherapy with chimeric antigen receptor engineered T cells Cancer Lett. Feb. 28, 2014;343(2):172-8. Epub Oct. 16, 2013.
Xu, X.J., et al., Efficacy and safety of adoptive immunotherapy using anti-CD 19 chimeric antigen receptor transduced T-cells: a systematic review of phase I clinical trials, LeukLymphoma (2013); 54(2): 255-60 (Published online: Sep. 8, 2012).
Ye, H, et al., The Structural Basis for the Recognition of Diverse Receptor Sequences by TRAF2, The Weill Medical College and Graduate School of Medical Sciences of Cornell University; v: 321-330.
Yee, C., et al., Prospects for Adoptive T Cell Therapy, Current Opinion in Immunology (1997); 9(5):702-708.
Zhang et al., Phase I Escalating-Dose Trial of CAR-T Therapy Targeting CEA + Metastatic Colorectal Cancers, Molecular Therapy (2017), 25(5): 1248-1258.
Zhang, H., et al., 4-IBB is superior to CD28 costimulation for generating CD8+ cytotoxic lymphocytes for adoptive immunotherapy. J Immunol, 2007. 179(7): p. 4910-8.
Zhao, Y. et al., A herceptin-based chimeric antigen receptor with modified signaling domains leads to enhanced survival of transduced T lymphocytes and antitumor activity, J. Immunol, 2009, 183, 5563-5574.
Zheng et al., Arming Tumor-Reactive T Cells with Costimulator B7-1 Enhances Therapeutic Efficacy of the T Cells, Cancer Research, 2006, vol. 66, No. 13, pp. 6793-6799.
Zhong, et al., Integrated CD28 and 4-1BB Signals Strongly Potentiate CD8+ T Cell Mediated Eradication of Metastatic Prostate Cancer, Molecular Therapy (Jan. 1, 2006); 13: p. S103, Abstract.
Altschul et al., "Local Alignment Statistics, [27] Multiple Alignment and Phylogenetic Trees," Methods in Enzymology (1996) 266:460-480.
Berger et al., Feb. 2015, Safety of targeting ROR1 in primates with chimeric antigen receptor modified T cells, Cancer Immunology Research, 3(2):206-216.
Bio-Rad 2016, The T Cell Marker, CD3 Antigen and Antibodies, retrieved on May 4, 2024 from the Internet: <URL: https://www.bio-rad-antibodies.com/static/2016/innate/the-t-cell-marker-cd3-antigen-and-antibodies.pdf>, 5 pp.
Caruana et al., 2013, Boosting in vivo CAR-redirected virus-specific CTLs with universal-artificial antigen presenting cells, Blood, 122(21):4204.
Cheng et al., Mar. 26, 2004, Hapten-directed targeting to single-chain antibody receptors, Cancer Gene Therapy, 11(5):380-388.
Chothia et al., December 1989, Conformations of immunoglobulin hypervariable regions, Nature, 342:877-883.
Deming et al., Oct. 6, 2014, Phospholipid ether analogs for the detection of colorectal tumors. PLOS One, 9(10):e109668.
Deng et al., 2019, Antitumor activity of NKG2D CAR-T cells against human colorectal cancer cells in vitro and in vivo, Am J. Cancer Res, 9(5):945-958.
Dissanayake et al., Mar. 19, 2014, Peptide-pulsed dendritic cells have superior ability to induce immune-mediated tissue destruction compared to peptide with adjuvant. PLOS One, 9(3):e92380, 10 pp.
Fang et al., Jul. 17, 2013, Lipid-insertion enables targeting functionalization of erythrocyte membrane- cloaked nanoparticles, Nanoscale, 5(19): 8884-8888.
Hudecek et al. Jun. 15, 2013, Receptor affinity and extracellular domain modifications affect tumor recognition by ROR1-specific chimeric antigen receptor T-cells. Clin Cancer Res. 19(12):3153-3164.
Johnson et al., 2000, Kabat database and its applications: 30 years after the first variability plot, Nucleic Acids Res., 28(1): 214-218.
Kabat et al., 1991, Sequences of Proteins of Immunological Interest, 5th Ed. Public Health Service, National Institutes of Health, Bethesda, Md. (TOC).
Kozer et al., 2011, Evidence for extended YFP-EGFR dimers in the absence of ligand on the surface of living cells, Physical Biology, 8:066002, 12 pp.
Kunik et al., Jun. 6, 2012, Paratome: an online tool for systematic identification of antigen-binding regions in antibodies based on sequence or structure, Nucl Acids Res. 40:W521-W524.
Lee et al., Jan. 15, 2019, Use of a single CAR T cell and several bispecific adapters facilitates eradication of multiple antigenically different solid tumors, Cancer Research, 79(2):387-396.
Lefranc et al., 2003, IMGT unique numbering for immunoglobulin and T cell receptor variable domains and Ig superfamily V-like domains, Dev Comp Immunol. 27:55-77.
Li et al., Jan. 2020, CAIZ-specific CAR-T cells and sunitinib show synergistic effects against metastatic renal cancer models, J Immunother, 43(1): 16-28.
Lohmueller et al., 2018, mSA2 affinity-enhanced biotin-binding CAR T cells for universal tumor targeting, Oncoimmunology, 7(1):e1368604.
Lu et al., Mar. 2019, Preclinical Evaluation of Bispecific Adaptor Molecule Controlled Folate Receptor CAR-T Cell Therapy with Special Focus on Pediatric Malignancies. Frontiers in Oncology, 9(51): 1-20.
Ma et al., Jul. 12, 2019, Enhanced CAR-T cell activity against solid tumors by vaccine boosting through the chimeric receptor, Science, 365(6449): 162-168.

(56) References Cited

OTHER PUBLICATIONS

Makabe et al., Jan. 11, 2008, Thermodynamic consequences of mutations in Vernier zone residues of a humanized anti-human epidermal growth factor receptor murine antibody, 528, Journal of Biological Chemistry, 283(2): 1156-1166.

Martin et al., Dec. 1989, Modeling antibody hypervariable loops: a combined algorithm, Proc Natl Acad Sci (USA), 86:9268-9272.

McEnaney et al., Jul. 20, 2012, Antibody-recruiting molecules: an emerging paradigm for engaging immune function in treating human disease. ACS Chem Biol. 7(7): 1139-1151.

Ruella et al., 2016, Dual CD19 and CD123 targeting prevents antigen-loss relapses after cd19-directed immunotherapies, J Clin Invest. 126(10): 3814-3826.

Samudrala et al., 1999, Ab Initio Protein Structure Prediction Using a Combined Hierarchical Approach, Proteins, Structure, Function and Genetics Suppl., 3:194-198.

Sun et al., Jan. 2018, Immunotherapy with CAR-Modified T cells: toxicities and overcoming strategies, Journal of Immunology Research, 2018:1-10.

Tatsumi et al., 2012, he non-invasive cell surface modification of hepatocytes with PEG-lipid derivatives, Biomaterials, 33:821-828.

Weichert et al., Jun. 11, 2014, Alkylphosphocholine analogs for broad-spectrum cancer imaging and therapy. Science Translational Medicine, 6(240):240ra75, 24 pp.

Zarour, 2016, Reversing T-cell dysfunction and exhaustion in cancer, Clinical Cancer Research, 22(8): 1856-1864.

\* cited by examiner

SEQUENCE LISTING

```
<160> NUMBER OF SEQ ID NOS: 13

<210> SEQ ID NO 1
<211> LENGTH: 251
<212> TYPE: PRT
<213> ORGANISM: Artificial Sequence
<220> FEATURE:
<223> OTHER INFORMATION: antiFL(FITC-E2 Mut2 CAR)

<400> SEQUENCE: 1

Ser Val Leu Thr Gln Pro Ser Ser Val Ser Ala Ala Pro Gly Gln Lys
1               5                   10                  15

Val Thr Ile Ser Cys Ser Gly Ser Thr Ser Asn Ile Gly Asn Asn Tyr
            20                  25                  30

Val Ser Trp Tyr Gln Gln His Pro Gly Lys Ala Pro Lys Leu Met Ile
        35                  40                  45
```

Tyr Asp Val Ser Lys Arg Pro Ser Gly Val Pro Asp Arg Phe Ser Gly
        50                  55                  60

Ser Lys Ser Gly Asn Ser Ala Ser Leu Asp Ile Ser Gly Leu Gln Ser
65                  70                  75                  80

Glu Asp Glu Ala Asp Tyr Tyr Cys Ala Ala Trp Asp Asp Ser Leu Ser
                85                  90                  95

Glu Phe Leu Phe Gly Thr Gly Thr Lys Leu Thr Val Leu Gly Gly Gly
            100                 105                 110

Gly Ser Gly Gly Gly Gly Ser Gly Gly Gly Gly Ser Gln Val Gln
        115                 120                 125

Leu Val Glu Ser Gly Gly Asn Leu Val Gln Pro Gly Gly Ser Leu Arg
    130                 135                 140

Leu Ser Cys Ala Ala Ser Gly Phe Thr Phe Gly Ser Phe Ser Met Ser
145                 150                 155                 160

Trp Val Arg Gln Ala Pro Gly Gly Leu Glu Trp Val Ala Gly Leu
                165                 170                 175

Ser Ala Arg Ser Ser Leu Thr His Tyr Ala Asp Ser Val Lys Gly Arg
            180                 185                 190

Phe Thr Ile Ser Arg Asp Asn Ala Lys Asn Ser Val Tyr Leu Gln Met
        195                 200                 205

Asn Ser Leu Arg Val Glu Asp Thr Ala Val Tyr Tyr Cys Ala Arg Arg
210                 215                 220

Ser Tyr Asp Ser Ser Gly Tyr Trp Gly His Phe Ala Ser Tyr Met Asp
225                 230                 235                 240

Val Trp Gly Gln Gly Thr Leu Val Thr Val Ser
                245                 250

<210> SEQ ID NO 2
<211> LENGTH: 254
<212> TYPE: PRT
<213> ORGANISM: Artificial Sequence
<220> FEATURE:
<223> OTHER INFORMATION: (antiFL(4M5.3) CAR)

<400> SEQUENCE: 2

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Ser Ser Ala Asp Asp Ala Lys Lys Asp Ala Ala Lys Lys Asp Asp Ala
        115                 120                 125

Lys Lys Asp Asp Ala Lys Lys Asp Gly Val Lys Leu Asp Glu Thr
    130                 135                 140

Gly Gly Gly Leu Val Gln Pro Gly Gly Ala Met Lys Leu Ser Cys Val
145                 150                 155                 160

```
Thr Ser Gly Phe Thr Phe Gly His Tyr Trp Met Asn Trp Val Arg Gln
            165                 170                 175

Ser Pro Glu Lys Gly Leu Glu Trp Val Ala Gln Phe Arg Asn Lys Pro
        180                 185                 190

Tyr Asn Tyr Glu Thr Tyr Tyr Ser Asp Ser Val Lys Gly Arg Phe Thr
            195                 200                 205

Ile Ser Arg Asp Asp Ser Lys Ser Ser Val Tyr Leu Gln Met Asn Asn
        210                 215                 220

Leu Arg Val Glu Asp Thr Gly Ile Tyr Tyr Cys Thr Gly Ala Ser Tyr
225                 230                 235                 240

Gly Met Glu Tyr Leu Gly Gln Gly Thr Ser Val Thr Val Ser
            245                 250
```

<210> SEQ ID NO 3
<211> LENGTH: 244
<212> TYPE: PRT
<213> ORGANISM: Artificial Sequence
<220> FEATURE:
<223> OTHER INFORMATION: (antiFL(4420) CAR)

<400> SEQUENCE: 3

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Gln Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
            85                  90                  95

Thr His Val Pro Trp Thr Phe Gly Gly Gly Thr Lys Leu Glu Ile Gly
            100                 105                 110

Gly Gly Gly Ser Gly Gly Gly Gly Ser Gly Gly Gly Gly Ser Glu Val
        115                 120                 125

Lys Leu Asp Glu Thr Gly Gly Gly Leu Val Gln Pro Gly Arg Pro Met
130                 135                 140

Lys Leu Ser Cys Val Ala Ser Gly Phe Thr Phe Ser Asp Tyr Trp Met
145                 150                 155                 160

Asn Trp Val Arg Gln Ser Pro Glu Lys Gly Leu Glu Trp Val Ala Gln
            165                 170                 175

Ile Arg Asn Lys Pro Tyr Asn Tyr Glu Thr Tyr Tyr Ser Asp Ser Val
        180                 185                 190

Lys Gly Arg Phe Thr Ile Ser Arg Asp Asp Ser Lys Ser Ser Val Tyr
            195                 200                 205

Leu Gln Met Asn Asn Leu Arg Val Glu Asp Met Gly Ile Tyr Tyr Cys
        210                 215                 220

Thr Gly Ser Tyr Tyr Gly Met Asp Tyr Trp Gly Gln Gly Thr Ser Val
225                 230                 235                 240

Thr Val Ser Ser
```

<210> SEQ ID NO 4
<211> LENGTH: 265
<212> TYPE: PRT

<213> ORGANISM: Artificial Sequence
<220> FEATURE:
<223> OTHER INFORMATION: (antiFL(4D5Flu) CAR)

<400> SEQUENCE: 4

```
Asp Tyr Lys Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Ser Leu
            20                  25                  30

Val His Ser Gln Gly Asn Thr Tyr Leu Arg Trp Tyr Gln Lys Pro
        35                  40                  45

Gly Lys Ala Pro Lys Val Leu Ile Tyr Lys Val Ser Asn Arg Phe Ser
50                  55                  60

Gly Val Pro Ser Arg Phe Ser Gly Ser Gly Ser Gly Thr Asp Phe Thr
65                  70                  75                  80

Leu Thr Ile Ser Ser Leu Gln Pro Glu Asp Phe Ala Thr Tyr Tyr Cys
                85                  90                  95

Gln Gln Ser Thr His Val Pro Trp Thr Phe Gly Gln Gly Thr Lys Val
            100                 105                 110

Glu Leu Lys Arg Ala Gly Gly Gly Ser Gly Gly Gly Ser Gly
        115                 120                 125

Gly Gly Gly Ser Ser Gly Gly Gly Ser Gly Gly Gly Ser Gly Gly
            130                 135                 140

Gly Gly Ser Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Asp Tyr Trp Met Asn Trp Val Arg Gln Ala Pro Gly Lys Gly Leu
            180                 185                 190

Glu Trp Val Ala Gln Ile Arg Asn Lys Pro Tyr Asn Tyr Glu Thr Tyr
        195                 200                 205

Tyr Ala Asp Ser Val Lys Gly Arg Phe Thr Ile Ser Arg Asp Thr Ser
    210                 215                 220

Lys Asn Thr Val Tyr Leu Gln Met Asn Ser Leu Arg Ala Glu Asp Thr
225                 230                 235                 240

Ala Val Tyr Tyr Cys Thr Gly Ser Tyr Tyr Gly Met Asp Tyr Trp Gly
                245                 250                 255

Gln Gly Thr Leu Val Thr Val Ser Ser
            260                 265
```

<210> SEQ ID NO 5
<211> LENGTH: 251
<212> TYPE: PRT
<213> ORGANISM: Artificial Sequence
<220> FEATURE:
<223> OTHER INFORMATION: (antiFL(FITCE2) CAR)

<400> SEQUENCE: 5

```
Ser Val Leu Thr Gln Pro Ser Ser Val Ser Ala Ala Pro Gly Gln Lys
1               5                   10                  15

Val Thr Ile Ser Cys Ser Gly Ser Thr Ser Asn Ile Gly Asn Asn Tyr
            20                  25                  30

Val Ser Trp Tyr Gln Gln His Pro Gly Lys Ala Pro Lys Leu Met Ile
        35                  40                  45

Tyr Asp Val Ser Lys Arg Pro Ser Gly Val Pro Asp Arg Phe Ser Gly
50                  55                  60
```

```
Ser Lys Ser Gly Asn Ser Ala Ser Leu Asp Ile Ser Gly Leu Gln Ser
 65                  70                  75                  80

Glu Asp Glu Ala Asp Tyr Tyr Cys Ala Ala Trp Asp Ser Leu Ser
             85                  90                  95

Glu Phe Leu Phe Gly Thr Gly Thr Lys Leu Thr Val Leu Gly Gly Gly
            100                 105                 110

Gly Gly Ser Gly Gly Gly Gly Ser Gly Gly Gly Ser Gln Val Gln
            115                 120                 125

Leu Val Glu Ser Gly Gly Asn Leu Val Gln Pro Gly Gly Ser Leu Arg
            130                 135                 140

Leu Ser Cys Ala Ala Ser Gly Phe Thr Phe Gly Ser Phe Ser Met Ser
145                 150                 155                 160

Trp Val Arg Gln Ala Pro Gly Gly Gly Leu Glu Trp Val Ala Gly Leu
            165                 170                 175

Ser Ala Arg Ser Ser Leu Thr His Tyr Ala Asp Ser Val Lys Gly Arg
            180                 185                 190

Phe Thr Ile Ser Arg Asp Asn Ala Lys Asn Ser Val Tyr Leu Gln Met
            195                 200                 205

Asn Ser Leu Arg Val Glu Asp Thr Ala Val Tyr Tyr Cys Ala Arg Arg
210                 215                 220

Ser Tyr Asp Ser Ser Gly Tyr Trp Gly His Phe Tyr Ser Tyr Met Asp
225                 230                 235                 240

Val Trp Gly Gln Gly Thr Leu Val Thr Val Ser
            245                 250

<210> SEQ ID NO 6
<211> LENGTH: 251
<212> TYPE: PRT
<213> ORGANISM: Artificial Sequence
<220> FEATURE:
<223> OTHER INFORMATION: (antiFL(FITCE2 HisH131Ala))

<400> SEQUENCE: 6

Ser Val Leu Thr Gln Pro Ser Ser Val Ser Ala Ala Pro Gly Gln Lys
 1               5                  10                  15

Val Thr Ile Ser Cys Ser Gly Ser Thr Ser Asn Ile Gly Asn Asn Tyr
            20                  25                  30

Val Ser Trp Tyr Gln Gln His Pro Gly Lys Ala Pro Lys Leu Met Ile
            35                  40                  45

Tyr Asp Val Ser Lys Arg Pro Ser Gly Val Pro Asp Arg Phe Ser Gly
 50                 55                  60

Ser Lys Ser Gly Asn Ser Ala Ser Leu Asp Ile Ser Gly Leu Gln Ser
 65                 70                  75                  80

Glu Asp Glu Ala Asp Tyr Tyr Cys Ala Ala Trp Asp Ser Leu Ser
            85                  90                  95

Glu Phe Leu Phe Gly Thr Gly Thr Lys Leu Thr Val Leu Gly Gly Gly
            100                 105                 110

Gly Gly Ser Gly Gly Gly Gly Ser Gly Gly Gly Ser Gln Val Gln
            115                 120                 125

Leu Val Glu Ser Gly Gly Asn Leu Val Gln Pro Gly Gly Ser Leu Arg
            130                 135                 140

Leu Ser Cys Ala Ala Ser Gly Phe Thr Phe Gly Ser Phe Ser Met Ser
145                 150                 155                 160

Trp Val Arg Gln Ala Pro Gly Gly Gly Leu Glu Trp Val Ala Gly Leu
            165                 170                 175
```

```
Ser Ala Arg Ser Ser Leu Thr His Tyr Ala Asp Ser Val Lys Gly Arg
            180                 185                 190

Phe Thr Ile Ser Arg Asp Asn Ala Lys Asn Ser Val Tyr Leu Gln Met
        195                 200                 205

Asn Ser Leu Arg Val Glu Asp Thr Ala Val Tyr Tyr Cys Ala Arg Arg
    210                 215                 220

Ser Tyr Asp Ser Ser Gly Tyr Trp Gly Ala Phe Tyr Ser Tyr Met Asp
225                 230                 235                 240

Val Trp Gly Gln Gly Thr Leu Val Thr Val Ser
                245                 250

<210> SEQ ID NO 7
<211> LENGTH: 229
<212> TYPE: PRT
<213> ORGANISM: Artificial Sequence
<220> FEATURE:
<223> OTHER INFORMATION: (IgG4 hinge connected to a CH2 domain to a CH3
      domain spacer)

<400> SEQUENCE: 7

Glu Ser Lys Tyr Gly Pro Pro Cys Pro Pro Cys Pro Ala Pro Glu Phe
1               5                   10                  15

Asp Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 8
<211> LENGTH: 119
<212> TYPE: PRT
<213> ORGANISM: Artificial Sequence
<220> FEATURE:
<223> OTHER INFORMATION: (IgG4 hinge connected to a CH3 domain spacer)
```

<400> SEQUENCE: 8

Glu Ser Lys Tyr Gly Pro Pro Cys Pro Pro Cys Pro Gly Gln Pro Arg
1               5                   10                  15
Glu Pro Gln Val Tyr Thr Leu Pro Pro Ser Gln Glu Glu Met Thr Lys
            20                  25                  30
Asn Gln Val Ser Leu Thr Cys Leu Val Lys Gly Phe Tyr Pro Ser Asp
        35                  40                  45
Ile Ala Val Glu Trp Glu Ser Asn Gly Gln Pro Glu Asn Asn Tyr Lys
    50                  55                  60
Thr Thr Pro Pro Val Leu Asp Ser Asp Gly Ser Phe Phe Leu Tyr Ser
65                  70                  75                  80
Arg Leu Thr Val Asp Lys Ser Arg Trp Gln Glu Gly Asn Val Phe Ser
                85                  90                  95
Cys Ser Val Met His Glu Ala Leu His Asn His Tyr Thr Gln Lys Ser
            100                 105                 110
Leu Ser Leu Ser Leu Gly Lys
        115

<210> SEQ ID NO 9
<211> LENGTH: 12
<212> TYPE: PRT
<213> ORGANISM: Artificial Sequence
<220> FEATURE:
<223> OTHER INFORMATION: (IgG4 hinge only spacer)

<400> SEQUENCE: 9

Glu Ser Lys Tyr Gly Pro Pro Cys Pro Pro Cys Pro
1               5                   10

<210> SEQ ID NO 10
<211> LENGTH: 3198
<212> TYPE: DNA
<213> ORGANISM: Artificial Sequence
<220> FEATURE:
<223> OTHER INFORMATION: E2 anti-fluorescein antibody fragment CAR
      nucleic acid sequence

<400> SEQUENCE: 10
atgcttctcc tggtgacaag ccttctgctc tgtgagttac cacacccagc attcctcctg      60
atcccaagcg tgctgacaca gcctagctcc gtgtctgccg cccctggcca gaaagtgacc     120
atcagctgta gcggcagcac cagcaacatc ggcaacaact acgtgtcctg gtatcagcag     180
caccccggca aggcccccaa gctgatgatc tacgacgtgt ccaagcggcc cagcggcgtg     240
cccgatagat tttccggcag caagagcggc aacagcgcca gcctggatat cagcggcctg     300
cagtctgagg acgaggccga ctactattgc gccgcctggg acgatagcct gagcgagttc     360
ctgtttggca ccggcaccaa gctgacagtg ctgggcggag cggaggatc tggcggcgga     420
ggaagtggcg aggggggatc tcaggtgcag ctggtggaaa gcggcggcaa cctggtgcag     480
cctggcggat ctctgagact gagctgtgcc gccagcggct tcaccttcgg cagcttcagc     540
atgagctggg tgcgccaggc tcctggggga ggactggaat gggtggcagg actgagcgcc     600
agaagcagcc tgacccacta cgccgatagc gtgaagggcc ggttcaccat cagccgggac     660
aacgccaaga cagcgtgta cctgcagatg aacagcctgc gggtggaaga taccgccgtg     720
tactactgcg ccagacggtc ctacgacagc agcggctact ggggccactt ctacagctac     780
atggacgtgt ggggccaggg cacctcgtg acagtgtctg agagcaagta cggaccgccc     840
tgccccccctt gccctgcccc cgagttcgac ggcggaccca gcgtgttcct gttccccccc     900

```
aagcccaagg acaccctgat gatcagccgg acccccgagg tgacctgcgt ggtggtggac    960
gtgagccagg aagatcccga ggtccagttc aattggtacg tggacggcgt ggaagtgcac   1020
aacgccaaga ccaagcccag agaggaacag ttccagagca cctaccgggt ggtgtctgtg   1080
ctgaccgtgc tgcaccagga ctggctgaac ggcaaagaat acaagtgcaa ggtgtccaac   1140
aagggcctgc ccagcagcat cgaaaagacc atcagcaagg ccaagggcca gcctcgcgag   1200
ccccaggtgt acaccctgcc tccctcccag gaagagatga ccaagaacca ggtgtccctg   1260
acctgcctgg tgaagggctt ctaccccagc gacatcgccg tggagtggga gagcaacggc   1320
cagcctgaga caactacaa gaccacccct cccgtgctgg acagcgacgg cagcttcttc   1380
ctgtacagcc ggctgaccgt ggacaagagc cggtggcagg aaggcaacgt cttttagctgc   1440
agcgtgatgc acgaggccct gcacaaccac tacacccaga gagcctgag cctgtccctg   1500
ggcaagatgt tctgggtgct ggtggtggtg ggcggggtgc tggcctgcta cagcctgctg   1560
gtgacagtgg ccttcatcat cttttgggtg aaacggggca gaaagaaact cctgtatata   1620
ttcaaacaac catttatgag accagtacaa actactcaag aggaagatgg ctgtagctgc   1680
cgatttccag aagaagaaga aggaggatgt gaactgcggg tgaagttcag cagaagcgcc   1740
gacgcccctg cctaccagca gggccagaat cagctgtaca cgagctgaa cctgggcaga   1800
agggaagagt acgacgtcct ggataagcgg agaggccggg accctgagat gggcggcaag   1860
cctcggcgga agaaccccca ggaaggcctg tataacgaac tgcagaaaga caagatggcc   1920
gaggcctaca gcgagatcgg catgaagggc gagcggaggc ggggcaaggg ccacgacggc   1980
ctgtatcagg gcctgtccac cgccaccaag gatacctacg acgccctgca catgcaggcc   2040
ctgccccaa ggctcgaggg cggcggagag ggcagaggaa gtcttctaac atgcggtgac   2100
gtggaggaga atcccggccc taggatgctt ctcctggtga caagccttct gctctgtgag   2160
ttaccacacc cagcattcct cctgatccca cgcaaagtgt gtaacggaat aggtattggt   2220
gaatttaaag actcactctc cataaatgct acgaatatta aacacttcaa aaactgcacc   2280
tccatcagtg gcgatctcca catcctgccg gtggcattta ggggtgactc cttcacacat   2340
actcctcctc tggatccaca ggaactggat attctgaaaa ccgtaaagga atcacaggg   2400
tttttgctga ttcaggcttg gcctgaaaac aggacggacc tccatgcctt tgagaaccta   2460
gaaatcatac gcggcaggac caagcaacat ggtcagtttt ctcttgcagt cgtcagcctg   2520
aacataacat ccttgggatt acgctccctc aaggagataa gtgatggaga tgtgataatt   2580
tcaggaaaca aaaatttgtg ctatgcaaat acaataaact ggaaaaaact gtttgggacc   2640
tccggtcaga aaccaaaat tataagcaac agaggtgaaa acagctgcaa ggccacaggc   2700
caggtctgcc atgccttgtg ctcccccgag ggctgctggg gccggagcc cagggactgc   2760
gtctcttgcc ggaatgtcag ccgaggcagg gaatgcgtgg acaagtgcaa ccttctggag   2820
ggtgagccaa gggagtttgt ggagaactct gagtgcatac agtgccaccc agagtgcctg   2880
cctcaggcca tgaacatcac ctgcacagga cggggaccag acaactgtat ccagtgtgcc   2940
cactacattg acggccccca ctgcgtcaag acctgcccgg caggagtcat gggagaaaac   3000
aacaccctgg tctggaagta cgcagacgcc ggccatgtgt gccacctgtg ccatccaaac   3060
tgcacctacg gatgcactgg gccaggtctt gaaggctgtc aacgaatgg gcctaagatc   3120
ccgtccatcg ccactgggat ggtggggggcc ctcctcttgc tgctggtggt ggccctgggg   3180
atcggcctct tcatgtga                                                 3198
```

<210> SEQ ID NO 11
<211> LENGTH: 1065
<212> TYPE: PRT
<213> ORGANISM: Artificial Sequence
<220> FEATURE:
<223> OTHER INFORMATION: E2 anti-fluorescein antibody fragment CAR amino acid sequence

<400> SEQUENCE: 11

```
Met Leu Leu Val Thr Ser Leu Leu Cys Glu Leu Pro His Pro
1               5                   10                  15

Ala Phe Leu Leu Ile Pro Ser Val Leu Thr Gln Pro Ser Ser Val Ser
            20                  25                  30

Ala Ala Pro Gly Gln Lys Val Thr Ile Ser Cys Ser Gly Ser Thr Ser
        35                  40                  45

Asn Ile Gly Asn Asn Tyr Val Ser Trp Tyr Gln His Pro Gly Lys
    50                  55                  60

Ala Pro Lys Leu Met Ile Tyr Asp Val Ser Lys Arg Pro Ser Gly Val
65                  70                  75                  80

Pro Asp Arg Phe Ser Gly Ser Lys Ser Gly Asn Ser Ala Ser Leu Asp
                85                  90                  95

Ile Ser Gly Leu Gln Ser Glu Asp Glu Ala Asp Tyr Tyr Cys Ala Ala
            100                 105                 110

Trp Asp Asp Ser Leu Ser Glu Phe Leu Phe Gly Thr Gly Thr Lys Leu
            115                 120                 125

Thr Val Leu Gly Gly Gly Gly Ser Gly Gly Gly Gly Ser Gly Gly
        130                 135                 140

Gly Gly Ser Gln Val Gln Leu Val Glu Ser Gly Gly Asn Leu Val Gln
145                 150                 155                 160

Pro Gly Gly Ser Leu Arg Leu Ser Cys Ala Ala Ser Gly Phe Thr Phe
                165                 170                 175

Gly Ser Phe Ser Met Ser Trp Val Arg Gln Ala Pro Gly Gly Gly Leu
            180                 185                 190

Glu Trp Val Ala Gly Leu Ser Ala Arg Ser Ser Leu Thr His Tyr Ala
            195                 200                 205

Asp Ser Val Lys Gly Arg Phe Thr Ile Ser Arg Asp Asn Ala Lys Asn
        210                 215                 220

Ser Val Tyr Leu Gln Met Asn Ser Leu Arg Val Glu Asp Thr Ala Val
225                 230                 235                 240

Tyr Tyr Cys Ala Arg Arg Ser Tyr Asp Ser Ser Gly Tyr Trp Gly His
                245                 250                 255

Phe Tyr Ser Tyr Met Asp Val Trp Gly Gln Gly Thr Leu Val Thr Val
            260                 265                 270

Ser Glu Ser Lys Tyr Gly Pro Pro Cys Pro Pro Cys Pro Ala Pro Glu
        275                 280                 285

Phe Asp Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser Gln Glu Asp Pro Glu Val Gln Phe Asn Trp Tyr Val Asp Gly
                325                 330                 335

Val Glu Val His Asn Ala Lys Thr Lys Pro Arg Glu Glu Gln Phe Gln
            340                 345                 350

Ser Thr Tyr Arg Val Val Ser Val Leu Thr Val Leu His Gln Asp Trp
        355                 360                 365
```

```
Leu Asn Gly Lys Glu Tyr Lys Cys Lys Val Ser Asn Lys Gly Leu Pro
        370                 375                 380

Ser Ser Ile Glu Lys Thr Ile Ser Lys Ala Lys Gly Gln Pro Arg Glu
385                 390                 395                 400

Pro Gln Val Tyr Thr Leu Pro Pro Ser Gln Glu Glu Met Thr Lys Asn
                405                 410                 415

Gln Val Ser Leu Thr Cys Leu Val Lys Gly Phe Tyr Pro Ser Asp Ile
                420                 425                 430

Ala Val Glu Trp Glu Ser Asn Gly Gln Pro Glu Asn Asn Tyr Lys Thr
                435                 440                 445

Thr Pro Pro Val Leu Asp Ser Asp Gly Ser Phe Phe Leu Tyr Ser Arg
450                 455                 460

Leu Thr Val Asp Lys Ser Arg Trp Gln Glu Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Leu Gly Lys Met Phe Trp Val Leu Val Val Val Gly Gly
                500                 505                 510

Val Leu Ala Cys Tyr Ser Leu Leu Val Thr Val Ala Phe Ile Ile Phe
                515                 520                 525

Trp Val Lys Arg Gly Arg Lys Lys Leu Leu Tyr Ile Phe Lys Gln Pro
530                 535                 540

Phe Met Arg Pro Val Gln Thr Thr Gln Glu Glu Asp Gly Cys Ser Cys
545                 550                 555                 560

Arg Phe Pro Glu Glu Glu Glu Gly Gly Cys Glu Leu Arg Val Lys Phe
                565                 570                 575

Ser Arg Ser Ala Asp Ala Pro Ala Tyr Gln Gln Gly Gln Asn Gln Leu
                580                 585                 590

Tyr Asn Glu Leu Asn Leu Gly Arg Arg Glu Glu Tyr Asp Val Leu Asp
                595                 600                 605

Lys Arg Arg Gly Arg Asp Pro Glu Met Gly Gly Lys Pro Arg Arg Lys
610                 615                 620

Asn Pro Gln Glu Gly Leu Tyr Asn Glu Leu Gln Lys Asp Lys Met Ala
625                 630                 635                 640

Glu Ala Tyr Ser Glu Ile Gly Met Lys Gly Glu Arg Arg Arg Gly Lys
                645                 650                 655

Gly His Asp Gly Leu Tyr Gln Gly Leu Ser Thr Ala Thr Lys Asp Thr
                660                 665                 670

Tyr Asp Ala Leu His Met Gln Ala Leu Pro Pro Arg Leu Glu Gly Gly
                675                 680                 685

Gly Glu Gly Arg Gly Ser Leu Leu Thr Cys Gly Asp Val Glu Glu Asn
                690                 695                 700

Pro Gly Pro Arg Met Leu Leu Leu Val Thr Ser Leu Leu Leu Cys Glu
705                 710                 715                 720

Leu Pro His Pro Ala Phe Leu Leu Ile Pro Arg Lys Val Cys Asn Gly
                725                 730                 735

Ile Gly Ile Gly Glu Phe Lys Asp Ser Leu Ser Ile Asn Ala Thr Asn
                740                 745                 750

Ile Lys His Phe Lys Asn Cys Thr Ser Ile Ser Gly Asp Leu His Ile
                755                 760                 765

Leu Pro Val Ala Phe Arg Gly Asp Ser Phe Thr His Thr Pro Pro Leu
770                 775                 780
```

-continued

```
Asp Pro Gln Glu Leu Asp Ile Leu Lys Thr Val Lys Glu Ile Thr Gly
785                 790                 795                 800

Phe Leu Leu Ile Gln Ala Trp Pro Glu Asn Arg Thr Asp Leu His Ala
            805                 810                 815

Phe Glu Asn Leu Glu Ile Ile Arg Gly Arg Thr Lys Gln His Gly Gln
        820                 825                 830

Phe Ser Leu Ala Val Val Ser Leu Asn Ile Thr Ser Leu Gly Leu Arg
    835                 840                 845

Ser Leu Lys Glu Ile Ser Asp Gly Asp Val Ile Ile Ser Gly Asn Lys
850                 855                 860

Asn Leu Cys Tyr Ala Asn Thr Ile Asn Trp Lys Lys Leu Phe Gly Thr
865                 870                 875                 880

Ser Gly Gln Lys Thr Lys Ile Ile Ser Asn Arg Gly Glu Asn Ser Cys
            885                 890                 895

Lys Ala Thr Gly Gln Val Cys His Ala Leu Cys Ser Pro Glu Gly Cys
        900                 905                 910

Trp Gly Pro Glu Pro Arg Asp Cys Val Ser Cys Arg Asn Val Ser Arg
    915                 920                 925

Gly Arg Glu Cys Val Asp Lys Cys Asn Leu Leu Glu Gly Glu Pro Arg
930                 935                 940

Glu Phe Val Glu Asn Ser Glu Cys Ile Gln Cys His Pro Glu Cys Leu
945                 950                 955                 960

Pro Gln Ala Met Asn Ile Thr Cys Thr Gly Arg Gly Pro Asp Asn Cys
            965                 970                 975

Ile Gln Cys Ala His Tyr Ile Asp Gly Pro His Cys Val Lys Thr Cys
        980                 985                 990

Pro Ala Gly Val Met Gly Glu Asn Asn Thr Leu Val Trp Lys Tyr Ala
    995                 1000                1005

Asp Ala Gly His Val Cys His Leu Cys His Pro Asn Cys Thr Tyr Gly
   1010                1015                1020

Cys Thr Gly Pro Gly Leu Glu Gly Cys Pro Thr Asn Gly Pro Lys Ile
1025                1030                1035                1040

Pro Ser Ile Ala Thr Gly Met Val Gly Ala Leu Leu Leu Leu Leu Val
            1045                1050                1055

Val Ala Leu Gly Ile Gly Leu Phe Met
        1060                1065

<210> SEQ ID NO 12
<211> LENGTH: 1068
<212> TYPE: PRT
<213> ORGANISM: Artificial Sequence
<220> FEATURE:
<223> OTHER INFORMATION: 4M5.3-CAR amino acid sequence

<400> SEQUENCE: 12

Met Leu Leu Leu Val Thr Ser Leu Leu Leu Cys Glu Leu Pro His Pro
1               5                   10                  15

Ala Phe Leu Leu Ile Pro Asp Val Val Met Thr Gln Thr Pro Leu Ser
            20                  25                  30

Leu Pro Val Ser Leu Gly Asp Gln Ala Ser Ile Ser Cys Arg Ser Ser
        35                  40                  45

Gln Ser Leu Val His Ser Asn Gly Asn Thr Tyr Leu Arg Trp Tyr Leu
    50                  55                  60

Gln Lys Pro Gly Gln Ser Pro Lys Val Leu Ile Tyr Lys Val Ser Asn
65                  70                  75                  80
```

-continued

```
Arg Val Ser Gly Val Pro Asp Arg Phe Ser Gly Ser Gly Ser Gly Thr
                 85                  90                  95
Asp Phe Thr Leu Lys Ile Asn Arg Val Glu Ala Glu Asp Leu Gly Val
            100                 105                 110
Tyr Phe Cys Ser Gln Ser Thr His Val Pro Trp Thr Phe Gly Gly Gly
            115                 120                 125
Thr Lys Leu Glu Ile Lys Ser Ser Ala Asp Asp Ala Lys Lys Asp Ala
            130                 135                 140
Ala Lys Lys Asp Asp Ala Lys Lys Asp Asp Ala Lys Lys Asp Gly Gly
145                 150                 155                 160
Val Lys Leu Asp Glu Thr Gly Gly Gly Leu Val Gln Pro Gly Gly Ala
                165                 170                 175
Met Lys Leu Ser Cys Val Thr Ser Gly Phe Thr Phe Gly His Tyr Trp
                180                 185                 190
Met Asn Trp Val Arg Gln Ser Pro Glu Lys Gly Leu Glu Trp Val Ala
            195                 200                 205
Gln Phe Arg Asn Lys Pro Tyr Asn Tyr Glu Thr Tyr Tyr Ser Asp Ser
    210                 215                 220
Val Lys Gly Arg Phe Thr Ile Ser Arg Asp Asp Ser Lys Ser Ser Val
225                 230                 235                 240
Tyr Leu Gln Met Asn Asn Leu Arg Val Glu Asp Thr Gly Ile Tyr Tyr
                245                 250                 255
Cys Thr Gly Ala Ser Tyr Gly Met Glu Tyr Leu Gly Gln Gly Thr Ser
                260                 265                 270
Val Thr Val Ser Glu Ser Lys Tyr Gly Pro Pro Cys Pro Pro Cys Pro
            275                 280                 285
Ala Pro Glu Phe Asp Gly Gly Pro Ser Val Phe Leu Phe Pro Pro Lys
    290                 295                 300
Pro Lys Asp Thr Leu Met Ile Ser Arg Thr Pro Glu Val Thr Cys Val
305                 310                 315                 320
Val Val Asp Val Ser Gln Glu Asp Pro Glu Val Gln Phe Asn Trp Tyr
                325                 330                 335
Val Asp Gly Val Glu Val His Asn Ala Lys Thr Lys Pro Arg Glu Glu
            340                 345                 350
Gln Phe Gln Ser Thr Tyr Arg Val Val Ser Val Leu Thr Val Leu His
    355                 360                 365
Gln Asp Trp Leu Asn Gly Lys Glu Tyr Lys Cys Lys Val Ser Asn Lys
    370                 375                 380
Gly Leu Pro Ser Ser Ile Glu Lys Thr Ile Ser Lys Ala Lys Gly Gln
385                 390                 395                 400
Pro Arg Glu Pro Gln Val Tyr Thr Leu Pro Pro Ser Gln Glu Glu Met
                405                 410                 415
Thr Lys Asn Gln Val Ser Leu Thr Cys Leu Val Lys Gly Phe Tyr Pro
            420                 425                 430
Ser Asp Ile Ala Val Glu Trp Glu Ser Asn Gly Gln Pro Glu Asn Asn
    435                 440                 445
Tyr Lys Thr Thr Pro Pro Val Leu Asp Ser Asp Gly Ser Phe Phe Leu
    450                 455                 460
Tyr Ser Arg Leu Thr Val Asp Lys Ser Arg Trp Gln Glu Gly Asn Val
465                 470                 475                 480
Phe Ser Cys Ser Val Met His Glu Ala Leu His Asn His Tyr Thr Gln
                485                 490                 495
```

```
Lys Ser Leu Ser Leu Ser Leu Gly Lys Met Phe Trp Val Leu Val Val
            500                 505                 510

Val Gly Gly Val Leu Ala Cys Tyr Ser Leu Leu Val Thr Val Ala Phe
        515                 520                 525

Ile Ile Phe Trp Val Lys Arg Gly Arg Lys Leu Leu Tyr Ile Phe
        530                 535             540

Lys Gln Pro Phe Met Arg Pro Val Gln Thr Thr Gln Glu Glu Asp Gly
545                 550                 555                 560

Cys Ser Cys Arg Phe Pro Glu Glu Glu Gly Gly Cys Glu Leu Arg
                565                 570                 575

Val Lys Phe Ser Arg Ser Ala Asp Ala Pro Ala Tyr Gln Gln Gly Gln
            580                 585                 590

Asn Gln Leu Tyr Asn Glu Leu Asn Leu Gly Arg Arg Glu Glu Tyr Asp
            595                 600                 605

Val Leu Asp Lys Arg Arg Gly Arg Asp Pro Glu Met Gly Gly Lys Pro
        610                 615                 620

Arg Arg Lys Asn Pro Gln Glu Gly Leu Tyr Asn Glu Leu Gln Lys Asp
625                 630                 635                 640

Lys Met Ala Glu Ala Tyr Ser Glu Ile Gly Met Lys Gly Glu Arg Arg
                645                 650                 655

Arg Gly Lys Gly His Asp Gly Leu Tyr Gln Gly Leu Ser Thr Ala Thr
            660                 665                 670

Lys Asp Thr Tyr Asp Ala Leu His Met Gln Ala Leu Pro Pro Arg Leu
            675                 680                 685

Glu Gly Gly Gly Glu Gly Arg Gly Ser Leu Leu Thr Cys Gly Asp Val
            690                 695                 700

Glu Glu Asn Pro Gly Pro Arg Met Leu Leu Leu Val Thr Ser Leu Leu
705                 710                 715                 720

Leu Cys Glu Leu Pro His Pro Ala Phe Leu Leu Ile Pro Arg Lys Val
                725                 730                 735

Cys Asn Gly Ile Gly Ile Gly Glu Phe Lys Asp Ser Leu Ser Ile Asn
            740                 745                 750

Ala Thr Asn Ile Lys His Phe Lys Asn Cys Thr Ser Ile Ser Gly Asp
            755                 760                 765

Leu His Ile Leu Pro Val Ala Phe Arg Gly Asp Ser Phe Thr His Thr
            770                 775                 780

Pro Pro Leu Asp Pro Gln Glu Leu Asp Ile Leu Lys Thr Val Lys Glu
785                 790                 795                 800

Ile Thr Gly Phe Leu Leu Ile Gln Ala Trp Pro Glu Asn Arg Thr Asp
                805                 810                 815

Leu His Ala Phe Glu Asn Leu Glu Ile Ile Arg Gly Arg Thr Lys Gln
            820                 825                 830

His Gly Gln Phe Ser Leu Ala Val Val Ser Leu Asn Ile Thr Ser Leu
            835                 840                 845

Gly Leu Arg Ser Leu Lys Glu Ile Ser Asp Gly Asp Val Ile Ile Ser
        850                 855                 860

Gly Asn Lys Asn Leu Cys Tyr Ala Asn Thr Ile Asn Trp Lys Lys Leu
865                 870                 875                 880

Phe Gly Thr Ser Gly Gln Lys Thr Lys Ile Ile Ser Asn Arg Gly Glu
            885                 890                 895
```

```
Asn Ser Cys Lys Ala Thr Gly Gln Val Cys His Ala Leu Cys Ser Pro
            900                 905                 910
Glu Gly Cys Trp Gly Pro Glu Pro Arg Asp Cys Val Ser Cys Arg Asn
        915                 920                 925
Val Ser Arg Gly Arg Glu Cys Val Asp Lys Cys Asn Leu Leu Glu Gly
    930                 935                 940
Glu Pro Arg Glu Phe Val Glu Asn Ser Glu Cys Ile Gln Cys His Pro
945                 950                 955                 960
Glu Cys Leu Pro Gln Ala Met Asn Ile Thr Cys Thr Gly Arg Gly Pro
                965                 970                 975
Asp Asn Cys Ile Gln Cys Ala His Tyr Ile Asp Gly Pro His Cys Val
            980                 985                 990
Lys Thr Cys Pro Ala Gly Val Met Gly Glu Asn Thr Leu Val Trp
        995                 1000                1005
Lys Tyr Ala Asp Ala Gly His Val Cys His Leu Cys His Pro Asn Cys
    1010                1015                1020
Thr Tyr Gly Cys Thr Gly Pro Gly Leu Glu Gly Cys Pro Thr Asn Gly
1025                1030                1035                1040
Pro Lys Ile Pro Ser Ile Ala Thr Gly Met Val Gly Ala Leu Leu Leu
                1045                1050                1055
Leu Leu Val Val Ala Leu Gly Ile Gly Leu Phe Met
            1060                1065

<210> SEQ ID NO 13
<211> LENGTH: 3207
<212> TYPE: DNA
<213> ORGANISM: Artificial Sequence
<220> FEATURE:
<223> OTHER INFORMATION: 4M5.3-CAR nucleotide sequence

<400> SEQUENCE: 13
atgcttctcc tggtgacaag ccttctgctc tgtgagttac cacacccagc attcctcctg      60
atcccagacg ttgtaatgac ccagacccct ctgtctctcc ccgtaagctt gggcgaccag     120
gcgagcatct cttgtcggtc ttcccagtcc ctggtccatt caaacggcaa tacttacttg     180
cggtggtact gcagaagcc cggtcaatcc ccaaaagtgc tgatatacaa ggttagcaat     240
cgggtcagtg gagtgcccga ccgcttcagc ggaagcggat ccgggactga cttcactctg     300
aagatcaacc gggtagaagc tgaagacctg ggggtgtact tctgctctca gtcaacacac     360
gtgccatgga cctttggagg tggcaccaag ctggaaatca atcatcagc ggacgatgcc     420 aaaaagacg cggccaagaa ggacgatgcc aagaaggatg atgctaaaaa ggatggcgga     480
gtcaaattgg acgagacagg cggggactg gtgcagcccg gcggtgccat gaaactgtct     540
tgtgtgacca gcggctttac cttcgggcat tattggatga ctgggtgcg acagtctcca     600 gagaaagggc tcgagtgggt ggcccagttt cgaaataaac cgtacaatta tgagacctac     660
tattcagatt ctgtgaaagg cgcttcact atttcacgcg acgacagcaa aagttccgtc     720
taccttcaga tgaacaacct tagagtggag ataccggaa tatactactg cacgggtgcc     780
agttatggca tggagtactt ggggcagggg acatctgtga ccgtttctga gagcaagtac     840
ggaccgccct gcccccttg ccctgccccc gagttcgacg gcggaccag cgtgttcctg     900 ttcccccca gcccaagga caccctgatg atcagccgga cccccgaggt gacctgcgtg     960
```

```
gtggtggacg tgagccagga agatcccgag gtccagttca attggtacgt ggacggcgtg    1020
gaagtgcaca acgccaagac caagcccaga gaggaacagt tccagagcac ctaccgggtg    1080
gtgtctgtgc tgaccgtgct gcaccaggac tggctgaacg gcaaagaata caagtgcaag    1140
gtgtccaaca agggcctgcc cagcagcatc gaaaagacca tcagcaaggc caagggccag    1200
cctcgcgagc cccaggtgta caccctgcct ccctcccagg aagagatgac caagaaccag    1260
gtgtccctga cctgcctggt gaagggcttc taccccagcg acatcgccgt ggagtgggag    1320
agcaacggcc agcctgagaa caactacaag accaccccctc ccgtgctgga cagcgacggc    1380
agcttcttcc tgtacagccg gctgaccgtg gacaagagcc ggtggcagga aggcaacgtc    1440
tttagctgca gcgtgatgca cgaggccctg cacaaccact acacccagaa gagcctgagc    1500
ctgtccctgg gcaagatgtt ctgggtgctg gtggtggtgg gcggggtgct ggcctgctac    1560
agcctgctgg tgacagtggc cttcatcatc ttttgggtga acgggcag aaagaaactc    1620 ctgtatatat tcaaacaacc atttatgaga ccagtacaaa ctactcaaga ggaagatggc    1680
tgtagctgcc gatttccaga agaagaagaa ggaggatgtg aactgcgggt gaagttcagc    1740
agaagcgccg acgcccctgc ctaccagcag ggccagaatc agctgtacaa cgagctgaac    1800
ctgggcagaa gggaagagta cgacgtcctg ataagcgga gaggccggga ccctgagatg    1860
ggcggcaagc ctcggcggaa gaaccccag gaaggcctgt ataacgaact gcagaaagac    1920
aagatggccg aggcctacag cgagatcggc atgaagggcg agcggaggcg gggcaagggc    1980
cacgacggcc tgtatcaggg cctgtccacc gccaccaagg ataccctacga cgccctgcac    2040 atgcaggccc tgccccaag gctcgagggc ggcggagagg gcagaggaag tcttctaaca    2100
tgcggtgacg tggaggagaa tcccggccct aggatgcttc tcctggtgac aagccttctg    2160
ctctgtgagt taccacaccc agcattcctc ctgatcccac gcaaagtgtg taacggaata    2220
ggtattggtg aatttaaaga ctcactctcc ataaatgcta cgaatattaa acacttcaaa    2280
aactgcacct ccatcagtgg cgatctccac atcctgccgg tggcatttag gggtgactcc    2340
ttcacacata ctcctcctct ggatccacag gaactggata ttctgaaaac cgtaaaggaa    2400
atcacagggt ttttgctgat tcaggcttgg cctgaaaaca ggacggacct ccatgccttt    2460
gagaacctag aaatcatacg cggcaggacc aagcaacatg gtcagttttc tcttgcagtc    2520
gtcagcctga acataacatc cttgggatta cgctccctca aggagataag tgatggagat    2580
gtgataattt caggaaacaa aaatttgtgc tatgcaaata caataaactg gaaaaaactg    2640
tttgggacct ccggtcagaa aaccaaaatt ataagcaaca gaggtgaaaa cagctgcaag    2700
gccacaggcc aggtctgcca tgccttgtgc tcccccgagg gctgctgggg cccggagccc    2760
agggactgcg tctcttgccg gaatgtcagc cgaggcaggg aatgcgtgga caagtgcaac    2820
cttctggagg tgagccaagg gagtttgtg gagaactctg agtgcataca gtgccaccca    2880
gagtgcctgc ctcaggccat gaacatcacc tgcacaggac ggggaccaga caactgtatc    2940
cagtgtgccc actacattga cggccccac tgcgtcaaga cctgcccggc aggagtcatg    3000
ggagaaaaca cacccctggt ctggaagtac gcagacgccg ccatgtgtg ccacctgtgc    3060 catccaaaact gcacctacgg atgcactggg ccaggtcttg aaggctgtcc aacgaatggg    3120
cctaagatcc cgtccatcgc cactgggatg gtgggggccc tcctcttgct gctggtggtg    3180
gccctgggga tcggcctctt catgtga                                       3207
```

FLUORESCEIN-SPECIFIC CARS EXHIBITING OPTIMAL T CELL FUNCTION AGAINST FL-PLE LABELLED TUMORS

CROSS-REFERENCE TO RELATED APPLICATIONS

This application is a U.S. National Phase Application of PCT International Application Number PCT/US2019/014054, filed on Jan. 17, 2019, designating the United States of America and published in the English language, which is an International Application of and claims the benefit of priority to U.S. Provisional Application No. 62/627,147, filed on Feb. 6, 2018. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SeqList-SCRI-163NP.txt, created Jul. 29, 2020, which is approximately 42 Kb in size. The information in the electronic format of the Sequence Listing is hereby expressly incorporated by reference in its entirety

FIELD OF THE INVENTION

The alternatives described herein pertain to engineered chimeric antigen receptors (CARs) and compositions thereof having specificity and affinity for fluorescein containing ligands presented on the surface of tumor cells. Accordingly, provided herein are compositions and methods of making and using these compositions.

BACKGROUND

The adoptive transfer of human T lymphocytes that are engineered by gene transfer to express chimeric antigen receptors (CARs) specific for surface molecules expressed on tumor cells has the potential to effectively treat cancer. Chimeric receptors are synthetic receptors that include an extracellular ligand binding domain, most commonly a single chain variable fragment of a monoclonal antibody (scFv) linked to intracellular signaling components, most commonly CD3ζ alone or combined with one or more costimulatory domains. Much of the research in the design of chimeric antigen receptors has focused on defining scFvs and other ligand binding elements that target malignant cells without causing serious toxicity to essential normal tissues, and on defining the optimal composition of intracellular signaling modules to activate T cell effector functions. There remains a need for a CAR T cell-mediated therapy that is selective for specific targets and which minimizes adverse side effects.

SUMMARY

In a first aspect, a complex is provided, wherein the complex comprises a chimeric antigen receptor (CAR) or a T cell receptor (TCR), wherein the CAR or TCR is joined to a lipid, wherein the lipid comprises a target moiety and the CAR is joined to said lipid through an interaction with said target moiety, and wherein the CAR or TCR comprises a spacer domain having a spacer length of 1-22 amino acids, 23-50 amino acids, 51-100 amino acids, 100 to 150 amino acids or 151-250 amino acids or a spacer length that is within a range defined by any two of the aforementioned lengths. In some alternatives, the CAR or TCR comprises a sequence as set forth in any one of SEQ ID NOs: 1-6. In some alternatives, the spacer domain is a IgG4 hinge connected to a CH2 domain to a CH3 domain. In some such embodiments, the spacer domain comprises the amino acid sequence SEQ ID NO: 7. In some alternatives, the spacer domain is an IgG4 hinge connected to a CH3 domain. In some such embodiments, the spacer domain comprises the amino acid sequence SEQ ID NO: 8. In some alternatives, the spacer domain is an IgG4 hinge only. In some such embodiments, the spacer domain comprises the amino acid sequence SEQ ID NO: 9. Some embodiments include nucleic acids that encode any one of SEQ ID NO: 1-9, which may be present on a vector and/or introduced to a cell (e.g., a T cell). In some alternatives, the spacer comprises a length of 229 amino acids. In some alternatives, the lipid comprises a polar head group and a hydrophobic group. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the polar-head group comprises phosphocholine, a piperidine moiety or a trimethylarseno-ethyl-phosphate moiety. In some alternatives, the hydrophobic group is fatty acid, such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid, such as a steroid or cholesterol. In some alternatives, the hydrophobic group comprises an ether linkage, wherein the ether linkage is between the polar head group and the aliphatic chain. In some alternatives, the sugar residue is a glycerol. In some alternatives, the hydrophobic group comprises a carbon alkyl chain, wherein the carbon alkyl chain comprises 10, 11, 12, 13, 14, 15, 16, 17, 18, 19 or 20 carbons or any number that is within a range defined by any two aforementioned values. In some alternatives, the carbon alkyl chain comprises 18 carbons. In some alternatives, the lipid is a phospholipid ether. In some alternatives, the target moiety is biotin, digoxigenin, dinitrophenol or fluorescein. In some alternatives, the spacer comprises a PEG spacer, a Hapten (2x) spacer, or an alkane chain. In some alternatives, the PEG spacer comprises 1, 2, 3, 4, 5, 6, 7, 8, 9, 10, 11, 12, 13, 14, 15 or 16 PEG molecules, or any amount of PEG molecules that is within a range defined by any two aforementioned values. In some alternatives, the CAR or TCR is expressed by a cell or a T cell. In some alternatives, the CAR or TCR is on the surface of a cell or a T cell. In some alternatives, the cell is a precursor T cell. In some alternatives, the precursor T cell is a hematopoietic stem cell. In some alternatives, the cell is a CD8+T cytotoxic lymphocyte cell selected from the group consisting of naïve CD8+ T cells, central memory CD8+ T cells, effector memory CD8+ T cells and bulk CD8+ T cells. In some alternatives, the cell is a CD4+T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell. In some alternatives, the target cell is a tumor cell. In some alternatives, the target cell is an immune cell. In some alternatives, the immune cell is a T cell or a B cell. In some alternatives, the target cell is present in a tumor microenvironment.

In a second aspect, a cell comprising a complex of any one of the alternatives herein is provided, the cell comprising a chimeric antigen receptor (CAR) or T cell receptor (TCR), wherein the CAR or TCR is bound to or is configured to bind to a lipid, wherein the lipid comprises a target moiety and the cell comprising the CAR is bound to the target moiety of the lipid, and wherein the CAR or TCR comprises a spacer domain. In some alternatives, the complex comprises a chimeric antigen receptor (CAR) or a T cell receptor (TCR), wherein the CAR or TCR is joined to or is configured to be joined to a lipid, wherein the lipid comprises a target moiety and the CAR is joined to or configured to be joined to said lipid through an interaction with said target moiety, and wherein the CAR or TCR comprises a spacer domain having a spacer length of 1-22 amino acids, 23-50 amino acids, 51-100 amino acids, 100 to 150 amino acids or 151-250 amino acids or a spacer length that is within a range defined by any two of the aforementioned lengths. In some alternatives, the CAR or TCR comprises a sequence as set forth in any one of SEQ ID NOs: 1-6. In some alternatives, the spacer domain is an IgG4 hinge connected to a CH2 domain to a CH3 domain. In some such embodiments, the spacer domain comprises the amino acid sequence SEQ ID NO: 7. In some alternatives, the spacer domain is an IgG4 hinge connected to a CH3 domain. In some such embodiments, the spacer domain comprises the amino acid sequence SEQ ID NO: 8. In some alternatives, the spacer domain is an IgG4 hinge only. In some such embodiments, the spacer domain comprises the amino acid sequence SEQ ID NO: 9. In some alternatives, the cell comprises a nucleic acid encoding any one of SEQ ID. NO: 1-9). In some alternatives, the spacer comprises a length of 229 amino acids. In some alternatives, the lipid comprises a polar head group and a hydrophobic group. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the polar-head group comprises phosphocholine, a piperidine moiety or a trimethylarseno-ethylphosphate moiety. In some alternatives, the hydrophobic group is fatty acid, such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid, such as a steroid or cholesterol. In some alternatives, the hydrophobic group comprises an ether linkage, wherein the ether linkage is between the polar head group and the aliphatic chain. In some alternatives, the sugar residue is a glycerol or sugar alcohol. In some alternatives, the hydrophobic group comprises a carbon alkyl chain, wherein the carbon alkyl chain comprises 10, 11, 12, 13, 14, 15, 16, 17, 18, 19 or 20 carbons or any number that is within a range defined by any two aforementioned values. In some alternatives, the carbon alkyl chain comprises 18 carbons. In some alternatives, the lipid is a phospholipid ether. In some alternatives, the target moiety is biotin, digoxigenin, dinitrophenol or fluorescein. In some alternatives, the spacer comprises a PEG spacer, a Hapten (2×) spacer, or an alkane chain. In some alternatives, the PEG spacer comprises 1, 2, 3, 4, 5, 6, 7, 8, 9, 10, 11, 12, 13, 14, 15 or 16 PEG molecules, or any amount of PEG molecules that is within a range defined by any two aforementioned values. In some alternatives, the CAR or TCR is expressed by a cell or a T cell. In some alternatives, the CAR or TCR is on the surface of a cell or a T cell. In some alternatives, the cell is a precursor T cell. In some alternatives, the precursor T cell is a hematopoietic stem cell. In some alternatives, the cell is a CD8+T cytotoxic lymphocyte cell selected from the group consisting of naïve CD8+ T cells, central memory CD8+ T cells, effector memory CD8+ T cells and bulk CD8+ T cells. In some alternatives, the cell is a CD4+T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell. In some alternatives, the target cell is a tumor cell. In some alternatives, the target cell is an immune cell. In some alternatives, the immune cell is a T cell or a B cell. In some alternatives, the target cell is present in a tumor microenvironment. In some alternatives, the cell is a precursor T cell. In some alternatives, the precursor T cell is a hematopoietic stem cell. In some alternatives, the cell is a CD8+T cytotoxic lymphocyte cell selected from the group consisting of naïve CD8+ T cells, central memory CD8+ T cells, effector memory CD8+ T cells and bulk CD8+ T cells. In some alternatives, the cell is a CD4+T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell. In some alternatives, the target cell is a tumor cell. In some alternatives, the target cell is an immune cell. In some alternatives, the immune cell is a T cell or a B cell. In some alternatives, the target cell is present in a tumor microenvironment.

In a third aspect, a method of treating, ameliorating, or inhibiting a cancer in a subject is provided, the method comprising a) introducing, providing, or administering to a subject a composition that comprises a lipid, which comprises a target moiety that is bound to a masking moiety, b) introducing, providing, or administering to said subject a cell comprising a chimeric antigen receptor (CAR) or T cell receptor (TCR), which is specific for the target moiety once the masking moiety is removed from the target moiety, and wherein the CAR or TCR comprises a spacer domain, c) removing the masking moiety from the target moiety thereby allowing the target moiety to bind to the CAR present on the cell, and, d) optionally, measuring or evaluating the binding of the cell comprising the CAR to the lipid, after steps a-c and/or e) optionally, measuring or evaluating the treatment, amelioration, or inhibition of said cancer after steps a-d, and/or f) and optionally, identifying a subject in need of a therapy for cancer prior to steps a-c. In some alternatives, the complex or the cell is provided to the subject at the same time as the composition or 1, 2, 3, 4, 5, 6, 7, 8, 9, 10, 11, 12, 15, 20, 24, 36 or 48 hours before or after administration of the composition, or any time within a range defined by any two aforementioned values. In some alternatives, the cell is provided to the subject 1, 2, 3, 4, 5, 6, 7, 8, 9, 10, 11, 12, 15, 20, 24, 36 or 48 hours before administration of the composition, or any time within a range defined by any two aforementioned values. In some alternatives, the cell is provided to the subject within seconds or minutes, such as less than an hour, of providing the composition to the subject. In some alternatives, a boost of the cell and/or the composition is provided to the subject. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is a solid tumor, such as colon, breast, ovarian, lung, pancreatic, prostate, melanoma, renal, pancreatic, glioblastoma, neuroblastoma, medulloblastoma, sarcoma or liver cancer; or a non-solid tumor, such as a leukemia, or a multiple myeloma. In some alternatives, the spacer domain is an IgG4 hinge connected to a CH2 domain to a CH3 domain. In some such embodiments, the spacer domain comprises the amino acid sequence SEQ ID NO: 7. In some alternatives, the spacer domain is an IgG4 hinge connected to a CH3 domain. In some such embodiments, the spacer domain comprises the amino acid sequence SEQ ID NO: 8. In some alternatives, the spacer domain is a IgG4 hinge only. In some such embodiments, the spacer domain comprises the amino acid sequence SEQ ID NO: 9. In some alternatives, the spacer comprises a sequence set forth in SEQ ID NO: 7. In some alternatives, binding of the target moiety to the CAR present on the cell induces production of at least one cytokine. In some alternatives, the at least one cytokine comprises IL-2, TNF-α and/or INF-α.

In a fourth aspect, a kit comprising a pharmaceutical grade FL-PLE is provided. In some alternatives, the pharmaceutical grade FL-PLE comprises a hapten. In some alternatives, the pharmaceutical grade FL-PLE comprises fluorescein (e.g., FITC).

BRIEF DESCRIPTION OF THE DRAWINGS

FIG. 1A shows an example of: (i) a second-generation CAR. The antigen recognition moiety (uppermost portion of molecule), which is presented at a desired distance by a short spacer domain, from the cell surface. This spacer is connected to a transmembrane domain, which is connected to two signaling domains; (ii) a medium spacer CAR, where another domain is added to the short spacer; and (iii) a long spacer CAR, where another domain is added to the medium spacer. FIG. 1B shows an example of different spacers exposed on CAR T cells. In some embodiments, long, medium, and short spacers can comprise a sequence as set forth in SEQ ID NO: 7, 8, and 9, respectively.

DETAILED DESCRIPTION

Figure 1A:
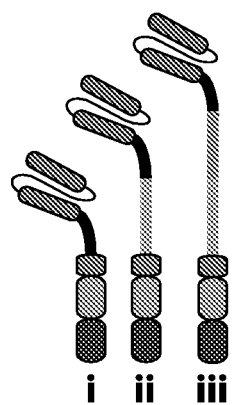
FIG. 1A and FIG. 1B schematically depict different spacers for CAR T cells.
Figure 1B:
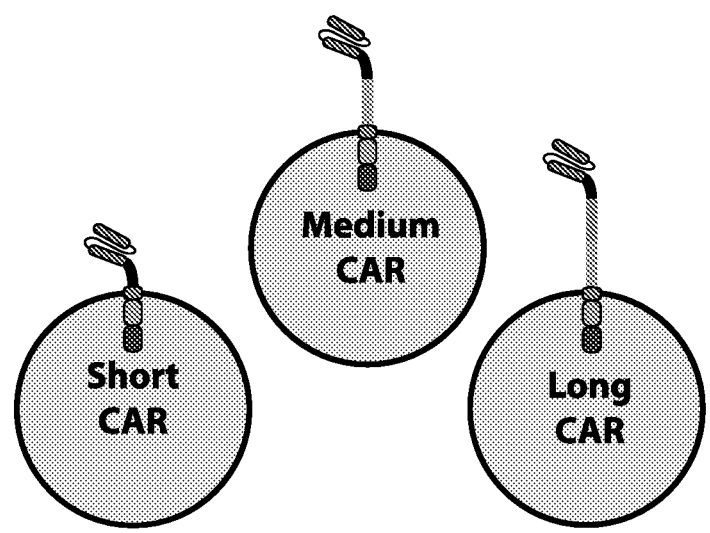
Figure 2:
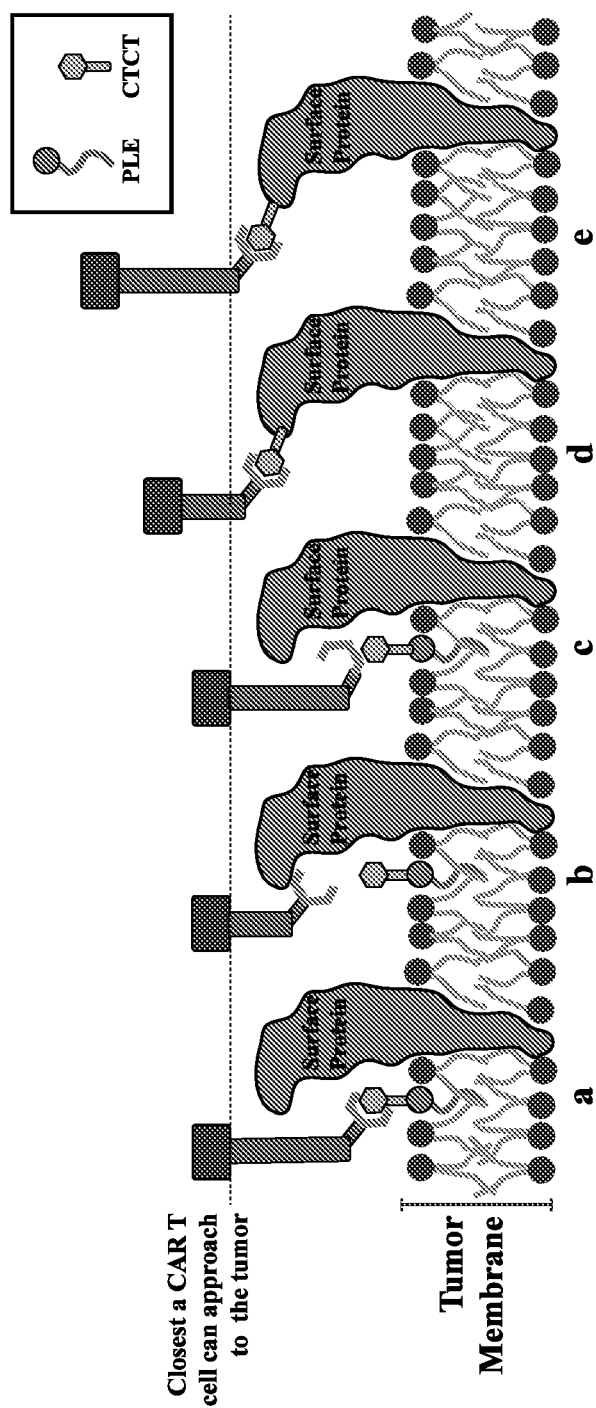
FIG. 2 schematically depicts an example of spacer length and orientation on a surface of a tumor cell. A tumor cell whose surface is labeled with CART cell tumor targeting agent (CTCT). The tumor surface has proteins and other cellular debris protruding from the surface, which can impact a CTCT specific CAR's ability to recognize the CAR T cell tumor targeting agent (CTCT). Panels A-C depict example embodiments of a PLE-CTCT imbedded into the lipid membrane, whereas panels D-E depict example embodiments of a CAR T cell tumor targeting agent (CTCT) conjugated to a surface protein. In panel A, a long CAR is able to reach and activate via the PLE-CTCT. In panel B, a short CAR is unable to reach the CAR T cell tumor targeting agent (CTCT) and will not be able to activate. In panel C, a long CAR whose recognition domain is placed in a different orientation and is unable recognize the CAR T cell tumor targeting agent (CTCT). In panels D and E, the long CAR from shown in panel C and the short CAR depicted in panel B are both able to recognize and activate through a CAR T cell tumor targeting agent (CTCT) that is conjugated to a surface protein.
Figure 3:
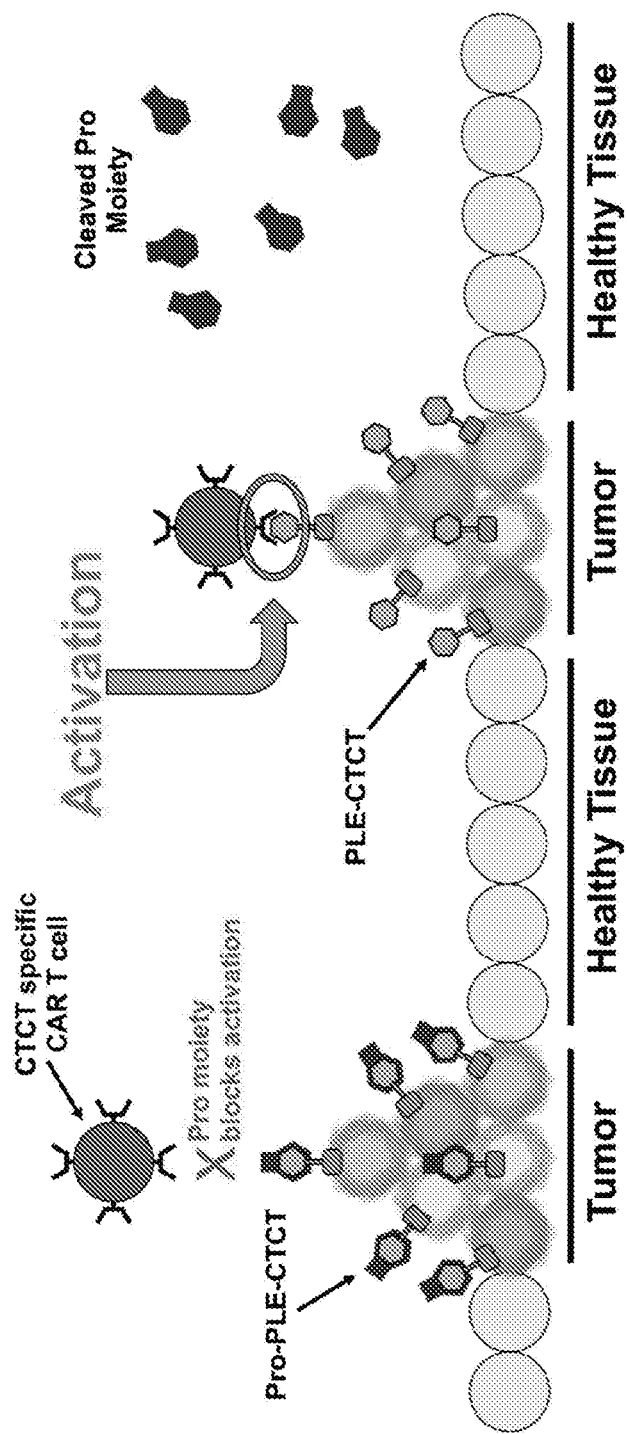
FIG. 3 schematically depicts an example of a CTCT CART cell recognizing only unmasked PLE-CTCT and being activated. A tumor loaded with a prodrug version of PLE-CTCT. In this example embodiment, the prodrug provides steric hindrance to the CTCT specific CAR T cell making the Pro-PLE-CTCT unrecognizable to the CTCT specific CAR T cell. Once the tumor microenvironment has cleaved the pro part of the Pro-PLE-CTCT, the CTCT specific CAR can recognize and activate through the unmasked PLE-CTCT.
Figure 4A:
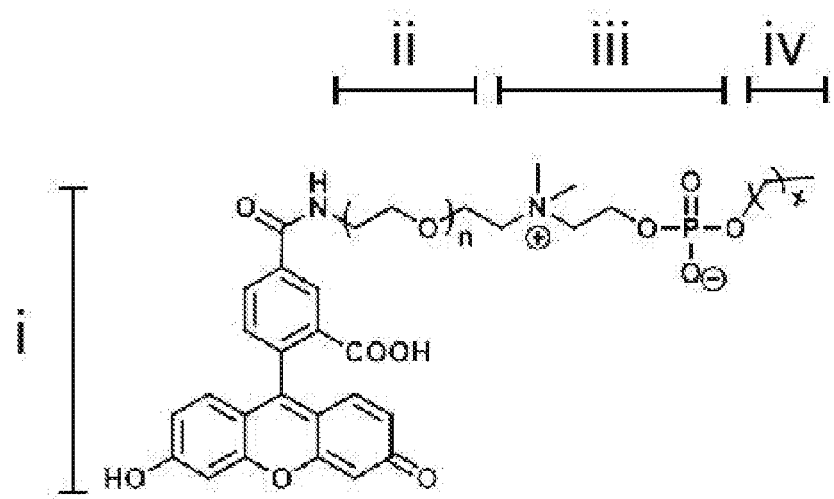
FIG. 4A depicts an example embodiment of a phospholipid conjugated with a hapten, fluorescein (PLE-CTCT). Structure of phospholipid ether (PLE) tethered to the hapten fluorescein (FL-PLE). (i) FL (fluorescein), the target for CAR T cells. (ii) Polyethylene glycol (PEG), the spacer used to extend the target an ideal distance from the cell surface. (iii & iv) PLE, (iii) is the polar head group and (iv) is the hydrophobic tail for incorporation or tethering into the cell plasma membrane.
Figure 4B:
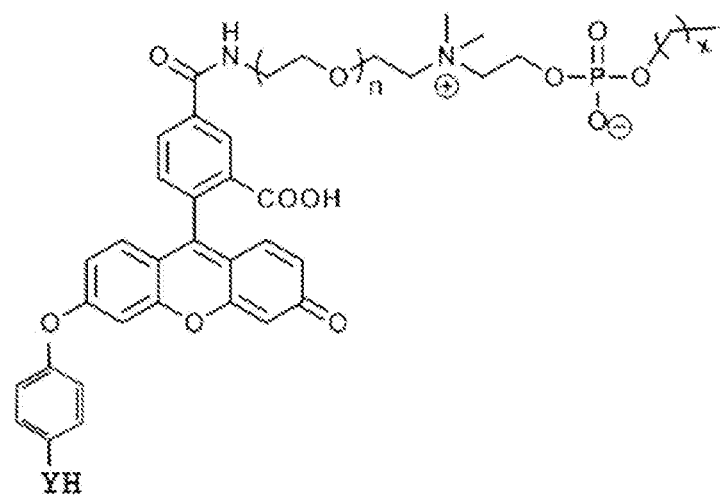
FIG. 4B depicts an example prodrug version of FL-PLE in which a Pro moiety is conjugated to the hapten (fluorescein) via a cleavable bond indicated by the arrow. The masked FL-PLE is substantially non-florescent. The bond can be cleaved by the presence of reactive oxygen species (ROS), such as in a tumor microenvironment. Once unmasked the resulting structure is FL-PLE, which provides a florescent signal and can be bind an antiFL CAR.
Figure 5:
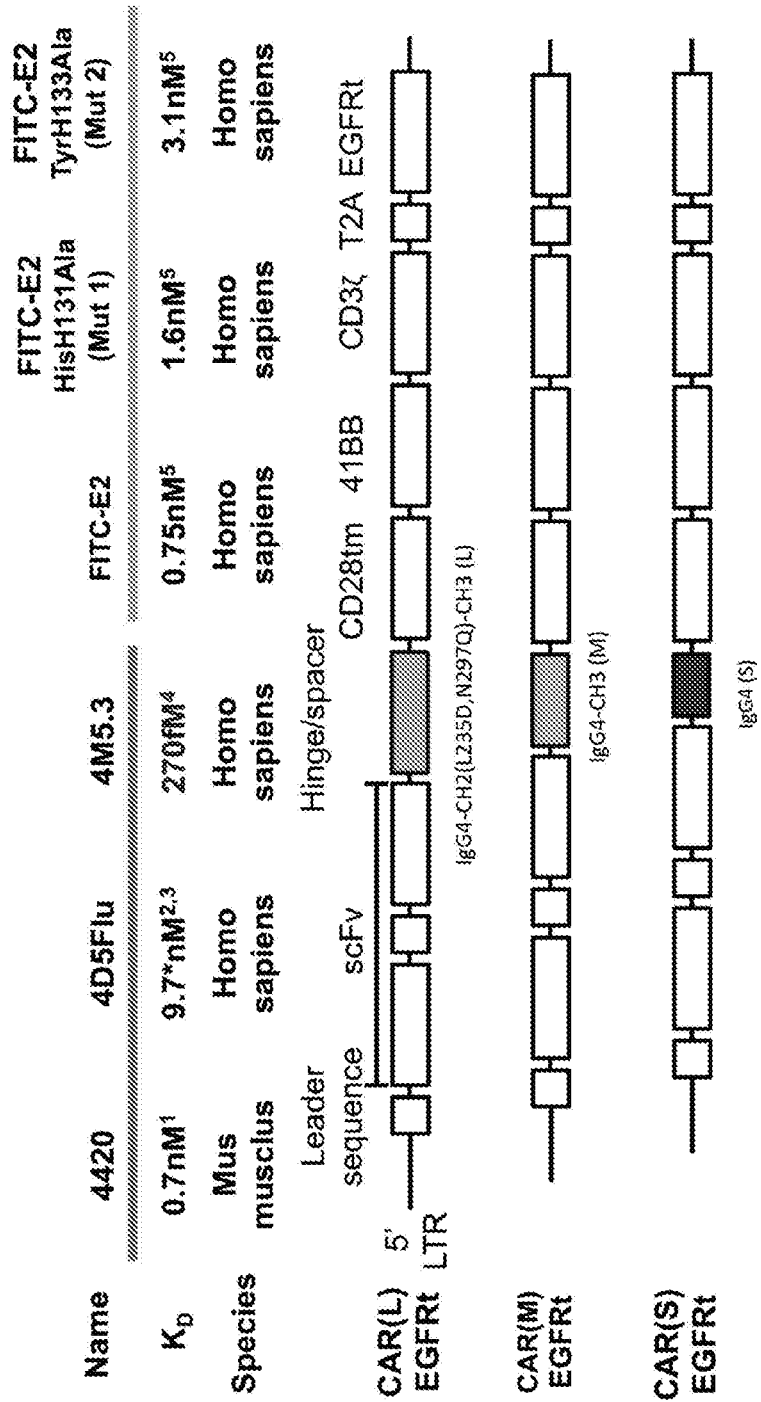
FIG. 5 depicts examples of different antiFL scFvs that were selected to create an antiFL CAR library (upper portion). Lower portion depicts structures of example CARs with a long spacer (L), a medium spacer (M), or a short spacer (S). The structures include a leader sequence, an scFv, a hinge/spacer, a CD28tm domain, a 41BB domain, a CD3ζ, a T2A sequence, and an EGFRt domain. In total 18 different plasmids were used to create antiFL CAR T cells.

Described herein are engineered chimeric antigen receptors (CARs) with specificity and a selected or designed affinity for the molecule fluorescein when presented on the surface of tumor cells loaded with exogenous FL-PLE, which results in redirected anti-tumor T cell reactivity. In some embodiments, FL-PLE is a synthetic molecular structure that is designed to integrate into the plasma membrane of tumors such that the molecule's fluorescein is present adjacent to the outer leaflet of the plasma membrane in the extracellular space. In some embodiments, the FL-PLE structure includes therapeutically important attributes. In some embodiments, a CAR that targets the fluorescein (FL) moiety of the FL-PLE is provided, and methods of making and using the same are also contemplated. These CARs can either be constitutively expressed or placed under regulated control.

While the adoptive transfer of transgene modified T cells has been successful in select settings, such as CD19 B cell lineage malignancies, these therapies have proved difficult to genericize to other cancer types because of the lack of a single target antigen that is present on all forms of cancer but not normal, healthy cells. Accordingly, the development of CAR T cell therapies was hampered by the onerous task of identifying and vetting tens of hundreds of antigens, such as CAR targets, as was the development of associated CARs in order to address each type of cancer afflicting humans. Previous work developed a FL-PLE that integrates into all tumors displaying one synthetic target molecule for CAR T cells to recognize. This eliminates the need for validation of tens of hundreds of CARs and instead allows for the use of a single FL specific CAR.

The present disclosure addresses the identification, creation, and engineering of suitable CAR T cells for binding to the FL moiety of FL-PLE. In some embodiments, the FL moiety may be masked and unmasked such that the FL moiety can be activated to receive the CAR T cell. In some embodiments, a FL specific CAR may recognize only unmasked CAR T cell tumor targeting agents (CTCTs) and not masked FLs.

Some embodiments of the methods and compositions provided herein can include aspects disclosed in WO 2018/148224 entitled "PHOSPHOLIPID ETHER (PLE) CAR T CELL TUMOR TARGETING (CTCT) AGENTS" which is hereby expressly incorporated by reference in its entirety.

Definitions

In the description that follows, the terms should be given their plain and ordinary meaning when read in light of the specification. One of skill in the art would understand the terms as used in view of the whole specification.

As used herein, "a" or "an" may mean one or more than one.

As used herein, the term "about" indicates that a value includes the inherent variation of error for the method being employed to determine a value, or the variation that exists among experiments.

"Chimeric receptor" as used herein refers to a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. Chimeric receptor can also be referred to as artificial T cell receptors, chimeric T cell receptors, chimeric immunoreceptors, and chimeric antigen receptors (CARs). These receptors can be used to graft the specificity of a monoclonal antibody or binding fragment thereof onto a T-cell, wherein transfer of their coding sequences is facilitated by viral vectors, such as a retroviral vector or a lentiviral vector. CARs are genetically engineered T-cell receptors designed to redirect T-cells to target cells that express specific cell-surface antigens. T-cells can be removed from a subject and modified so that they can express receptors that can be specific for an antigen by a process called adoptive cell transfer. The T-cells are reintroduced into the patient where they can then recognize and target an antigen. These CARs are engineered receptors that can graft a selected specificity onto an immune receptor cell. The term chimeric antigen receptors or "CARs" are also considered by some investigators to include the antibody or antibody fragment, the spacer, signaling domain, and transmembrane region. Due to the surprising effects of modifying the different components or domains of the CAR described herein, such as the epitope binding region (for example, antibody fragment, scFv, or portion thereof), spacer, transmembrane domain, and/or signaling domain), the components of the CAR are frequently distinguished throughout this disclosure in terms of independent elements.

"CAR T cell targeting agent," (CTCT) is given its plain and ordinary meaning in view of the specification and can be described, for example as a composition that that can integrate into the membrane of a target cell. In the alternatives herein, the CTCT comprises a lipid, wherein the lipid comprises a target moiety and a masking moiety. The masking moiety may be unmasked in the presence of low pH, ROS species and within a tumor microenvironment, for example. In some embodiments, the masking moiety inhibits specific binding of a CAR to the target moiety. The target moiety may be recognized and bound by a chimeric antigen receptor that is specific for the target moiety. In some alternatives herein, the masking moiety is removed at a pH of 4, 5, 6, or 6.5 or any pH in between a range defined by any two aforementioned values.

A "T cell receptor" or "TCR" is a molecule that is found on the surface of T lymphocytes or T cells that is responsible for the recognition of fragments of antigen bound to a major histocompatibility complex molecule.

"Target moiety" as described herein, refers to a specific group or site on a molecule or chemical that is a binding target for another chemical or protein of interest. In some alternatives, a complex is provided, wherein the complex comprises a chimeric antigen receptor (CAR) or a T cell receptor (TCR) joined to a lipid, wherein the lipid comprises a target moiety and the CAR is joined to said lipid through an interaction with said target moiety. In some alternatives, the target moiety is biotin, digoxigenin, dinitrophenol or fluorescein.

A "single-chain variable fragment," (scFv) is a fusion protein that can have variable regions of the heavy (VH) and light chains (VL) of immunoglobulins, connected with a short linker peptide of ten to 25 amino acids. The short linker peptide can comprise 10, 11, 12, 13, 14, 15, 16, 17, 18, 19, 20, 21, 22, 23, 24, 25 amino acids or any number of amino acids in between a range defined by any two aforementioned values. The linker is usually rich in glycine for flexibility, as well as, serine or threonine for solubility, and can either connect the N-terminus of the VH with the C-terminus of the VL, or vice versa. This protein retains the specificity of the original immunoglobulin, despite removal of the constant regions and the introduction of the linker. The scFv can be specific for an antigen. "Antigen" or "Ag" as used herein, refers to a molecule that provokes an immune response. This immune response can involve either antibody production, or the activation of specific immunologically-competent cells, or both. An antigen can be generated, synthesized, produced recombinantly or can be derived from a biological sample. Such a biological sample can include, but is not limited to a tissue sample, a tumor sample, a cell or a biological fluid such, for example, blood, plasma or ascites fluid. In some alternatives herein, a composition is provided, wherein the composition comprises cells manufactured by any one of the alternative methods herein. In some alternatives, the cells comprise a chimeric antigen receptor, wherein the chimeric antigen receptor comprises a scFv that is specific for an antigen.

Some embodiments provided herein relate to a ScFv described herein as antiFL(FITCE2 TyrH133Ala) (also referred to as antiFL(FITC-E2 Mut2), or as antiFL(Mut2)), which can be incorporated into a CAR in accordance with this disclosure (SEQ ID NO: 1), having an amino acid sequence of

```
SVLTQPSSVSAAPGQKVTISCSGSTSNIGNNYVSWYQQHPGKAPKLMIYD
VSKRPSGVPDRFSGSKSGNSASLDISGLQSEDEADYYCAAWDDSLSEFLF
GTGTKLTVLGGGGGSGGGGSGGGGSQVQLVESGGNLVQPGGSLRLSCAAS
GFTFGSFSMSWVRQAPGGGLEWVAGLSARSSLTHYADSVKGRFTISRDNA
KNSVYLQMNSLRVEDTAVYYCARRSYDSSGYWGHFASYMDVWGQGTLVTV
S.
```

Some embodiments provided herein relate to a scFv described herein as antiFL(4M5.3), which can be incorporated into a CAR in accordance with this disclosure (SEQ ID NO: 2), having an amino acid sequence of

```
DVVMTQTPLSLPVSLGDQASISCRSSQSLVHSNGNTYLRWYLQKPGQSPK
VLIYKVSNRVSGVPDRFSGSGSGTDFTLKINRVEAEDLGVYFCSQSTHVP
WTFGGGTKLEIKSSADDAKKDAAKKDDAKKDDAKKDGGVKLDETGGGLVQ
PGGAMKLSCVTSGFTFGHYWMNWVRQSPEKGLEWVAQFRNKPYNYETYYS
DSVKGRFTISRDDSKSSVYLQMNNLRVEDTGIYYCTGASYGMEYLGQGTS
VTVS.
```

Some embodiments provided herein relate to a ScFv described herein as antiFL(4420), which can be incorporated into a CAR in accordance with this disclosure (SEQ ID NO: 3), having an amino acid sequence of

```
DVVMTQTPLSLPVSLGDQASISCRSSQSLVHSQGNTYLRWYLQKPGQSPK
VLIYKVSNRFSGVPDRFSGSGSGTDFTLKISRVEAEDLGVYFCSQSTHVP
WTFGGGTKLEIGGGGSGGGGSGGGGSEVKLDETGGGLVQPGRPMKLSCVA
SGFTFSDYWMNWVRQSPEKGLEWVAQIRNKPYNYETYYSDSVKGRFTISR
DDSKSSVYLQMNNLRVEDMGIYYCTGSYYGMDYWGQGTSVTVSS.
```

Some embodiments provided herein relate to a ScFv described herein as antiFL(4D5Flu), which can be incorporated into a CAR in accordance with this disclosure (SEQ ID NO: 4), having an amino acid sequence of

```
DYKDIQMTQSPSSLSASVGDRVTITCRASQSLVHSQGNTYLRWYQQKPGK
APKVLIYKVSNRFSGVPSRFSGSGSGTDFTLTISSLQPEDFATYYCQQST
```

-continued
HVPWTFGQGTKVELKRAGGGGSGGGGSGGGGSSGGGSGGGGSGGGGSEVQ

LVESGGGLVQPGGSLRLSCAASGFTFSMWMNWVRQAPGKGLEWVAQIRNK

PYNYETYYADSVKGRFTISRDTSKNTVYLQMNSLRAEDTAVYYCTGSYYG

MDYWGQGTLVTVSS.

Some embodiments provided herein relate to a ScFv described herein as antiFL(FITCE2), which can be incorporated into a CAR in accordance with this disclosure (SEQ ID NO: 5), having an amino acid sequence of

SVLTQPSSVSAAPGQKVTISCSGSTSNIGNNYVSWYQQHPGKAPKLMIYD

VSKRPSGVPDRFSGSKSGNSASLDISGLQSEDEADYYCAAWDDSLSEFLF

GTGTKLTVLGGGGSGGGGSGGGGSQVQLVESGGNLVQPGGSLRLSCAAS

GFTFGSFSMSWVRQAPGGGLEWVAGLSARSSLTHYADSVKGRFTISRDNA

KNSVYLQMNSLRVEDTAVYYCARRSYDSSGYWGHFYSYMDVWGQGTLVTV

S.

Some embodiments provided herein relate to a ScFv described herein as antiFL(FITCE2 HisH131Ala), which can be incorporated into a CAR in accordance with this disclosure (SEQ ID NO: 6), having an amino acid sequence of

SVLTQPSSVSAAPGQKVTISCSGSTSNIGNNYVSWYQQHPGKAPKLMIYD

VSKRPSGVPDRFSGSKSGNSASLDISGLQSEDEADYYCAAWDDSLSEFLF

GTGTKLTVLGGGGSGGGGSGGGGSQVQLVESGGNLVQPGGSLRLSCAAS

GFTFGSFSMSWVRQAPGGGLEWVAGLSARSSLTHYADSVKGRFTISRDNA

KNSVYLQMNSLRVEDTAVYYCARRSYDSSGYWGAFYSYMDVWGQGTLVTV

S.

"Antigen specific binding domains" can include protein or protein domains that can specifically bind to an epitope on a protein at a low or high binding affinity (fM to mM binding capacity). In some alternatives, the fusion protein comprises a protein or portion thereof that can modulate an immune response. In some alternatives, the protein comprises an antigen specific binding domain.

T-cells" or "T lymphocytes" as used herein, can be from any mammalian species, preferably primate, including monkeys, dogs, and humans. In some alternatives the T-cells are allogeneic (from the same species but different donor) as the recipient subject; in some alternatives the T-cells are autologous (the donor and the recipient are the same); in some alternatives the T-cells are syngeneic (the donor and the recipients are different but are identical twins).

"Combination therapy" as described herein, refers to a therapy that uses more than one medication or modality for a treatment. Combination therapy, for example, can also refer to multiple therapies for a single disease, and often all the therapies are pharmaceutical product combinations. Combination therapy can also involve prescribing and administering separate drugs in which the dosage can also have more than one active ingredient. In some alternatives, a combination therapy is provided, wherein the combination therapy comprises administering a genetically modified immune cell for modifying a tumor microenvironment. In some alternatives, the combination therapy comprises administering a genetically modified immune cell for modulating the suppression of the immune response in a tumor microenvironment. In some alternatives, the combination therapy comprises administering a genetically modified immune cell for minimizing the proliferation of tumor and suppressive cells in a subject in need thereof e.g. a human. In some alternatives, the combination therapy comprises administering a genetically modified immune cell for increasing the efficiency of an anti-cancer therapy, anti-infection therapy, antibacterial therapy, anti-viral therapy, or anti-tumoral therapy in a subject in need thereof e.g., a human. In some alternatives, the combination therapy further comprises administration of an inhibitor. In some alternatives, the inhibitor is not an enzymatic inhibitor. In some alternatives, the inhibitor is an enzymatic inhibitor. In some alternatives, the combination therapy comprises administering a therapeutic dose of an inhibitor or an antibody or a binding fragment thereof. These antibodies or binding fragments thereof can be humanized in some alternatives. In some alternatives, the combination therapy can further comprise administering a CAR bearing T-cell to a subject in need e.g., a human.

"Chemotherapeutic drugs" are a category of anti-cancer medicaments that can use, for example, chemical substances, such as anti-cancer drugs (chemotherapeutic agents), which can be administered as part of a standardized chemotherapy regimen. Chemotherapeutic drugs can be administered with a curative intent or to prolong life or to reduce symptoms (palliative chemotherapy). Additional chemotherapies can also include hormonal therapy and targeted therapy, as it is one of the major categories of medical oncology (pharmacotherapy for cancer). These modalities are often used in conjunction with other cancer therapies, such as radiation therapy, surgery, and/or hyperthermia therapy. In a few cases, cancer has been known to spread due to surgery. In some alternatives, a genetically modified immune cell is administered to the tumor site prior to or after a surgical procedure.

Chemotherapy, in which chemotherapeutic drugs are administered, can use one drug at a time (single-agent chemotherapy) or several drugs at once (combination chemotherapy or polychemotherapy). The combination of chemotherapy and radiotherapy is chemoradiotherapy. Chemotherapy using drugs that convert to cytotoxic activity only upon light exposure is called photochemotherapy or photodynamic therapy. In some alternatives of administering the genetically modified immune cell described herein, the method can further comprise administering to a subject having cancer, photochemotherapy or photodynamic therapy after receiving the genetically modified immune cells or genetically engineered macrophages (GEMs).

Chemotherapuetic drugs can include but are not limited to antibody-drug conjugates (for example, an antibody attached to a drug by a linker), nanoparticles (for example a nanoparticle can be 1-1000 nanometer sized particle for promoting tumor selectivity and aid in delivering low-solubility drugs), electochemotherapy, alkylating agents, antimetabolites (for example, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, or Thioguanine), anti-tumor antibiotics, topoisomerase inhibitors, mitotic inhibitors, corticosteroids, DNA intercalating agents, or checkpoint inhibitors (for example checkpoint kinases CHK1, or CHK2). In some alternatives of the methods described herein, the genetically modified immune cells or compositions comprising genetically modified immune cells are administered in combination with one or more anti-cancer agents, such as any one or more of the foregoing compounds or therapies. In some alternatives, the one or more anti-cancer agent that is co-administered or administered in conjunction with the genetically modified immune cells, comprises antibody-drug conjugates, nanoparticles, electro-chemotherapy, alkylating agents, antimetabolites, anti-tumor antibiotics, topoisomerase inhibitors, mitotic inhibitors, corticosteroids, DNA intercalating agents, or checkpoint inhibitors. In some alternatives, the antimetabolites comprise 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, or Thioguanine.

"Subject" or "patient," as described herein, refers to any organism upon which the alternatives described herein may be used or administered, e.g., for experimental, diagnostic, prophylactic, and/or therapeutic purposes. Subjects or patients include, for example, animals. In some alternatives, the subject is mice, rats, rabbits, non-human primates, and humans. In some alternatives, the subject is a cow, sheep, pig, horse, dog, cat, primate or a human.

Some embodiments relate to a CAR T cell tumor targeting (CTCT) agent. Some embodiments provided herein relate to a phospholipid ether (PLE) tethered to the hapten fluorescein (FL-PLE). "Fluorescein" as described herein, is a synthetic organic compound that is soluble in water and alcohol. It is widely used as a fluorescent tracer for many applications. In the alternatives herein, fluorescein is a target moiety on a lipid that is specifically recognized by a chimeric antigen receptor designed and/or selected for its ability to bind or interact with the fluorescein. In some alternatives, the lipid is a phospholipid ether.

"Lipid" as described herein, is a class of organic compounds that comprise carbon chains, fatty acids or a fatty acid derivative that is typically insoluble in water but can integrate into or mix with hydrophobic or organic solvents. Without being limiting, lipids can include fats, waxes, fat soluble vitamins, monoglycerides, diglycerides, triglycerides, sphingolipids, cerebrosides, ceramides, or phospholipids. Described herein are amphiphilic lipids that can have a polar head group and a hydrophobic moiety or hydrophobic group. "Hydrophobic group" or hydrophobic moiety, as described herein, is a molecule or a part of a molecule that is repelled from a mass of water and tends to be non-polar. This can include alkanes, oils or fats. Without being limiting, lipids can be glycerolipids, glycerophospholipids, sphingolipids, sterol lipids, prenol lipids, saccharolipids or polyketides. In the alternatives herein a complex is provided, wherein the complex comprises a lipid. In some alternatives, the lipid comprises a polar head group and a hydrophobic moiety. In some alternatives, the hydrophobic moiety is a hydrophobic carbon tail. In some alternatives the hydrophobic carbon tail is saturated or unsaturated. In some alternatives, the hydrophobic carbon tail comprises 10, 11, 12, 13, 14, 15, 16, 17, 18, 19, 20, 21, 22, 23, 24 or 25 carbons or any number of carbons in between a range set forth in any aforementioned value. In some alternatives, the hydrophobic moiety is a steroid or a cholesterol. In some alternatives, the lipid comprises a glycerolipid, glycerophospholipid, sphingolipid, sterol lipid, prenol lipid, saccharolipid or polyketide. In some alternatives, the lipid is a phospholipid ether. In some alternatives, the lipid contains branched alkyl tails.

In some alternatives, the lipid can be a sphingolipid. The sphingolipid can contain a backbone of sphingoid bases, such as a set of aliphatic amino alcohols that includes sphingosine. A sphingolipid with an R group consisting of a hydrogen atom only is a ceramide. Other common R groups include phosphocholine, yielding a sphingomyelin, and various sugar monomers or dimers, yielding cerebrosides and globosides, respectively. Cerebrosides and globosides are collectively known as glycosphingolipids. In some alternatives, the lipid is a glycosphingolipid.

As provided herein, the lipid comprises a polar head group and a hydrophobic group. In some alternatives, the hydrophobic group comprises a fatty acid such as an aliphatic chain. The fatty acid can be saturated or unsaturated. In some alternatives, the hydrophobic group comprises an alkyl, alkenyl or alkynyl group. In some alternatives, the hydrophobic group comprises a terpenoid lipid, such as a steroid or cholesterol. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol or sugar alcohol.

In some alternatives, the lipid is a single chain alkylphospholipid.

In some alternatives, the lipid comprises a structure of synthetic alkylphospholipids, such as edelfosine, perifosine or erucylphosphocholine. In some alternatives, the lipid is a lysophosphatidylcholine, edlfosine, erucylphosphocholine, D-21805 or perfisone. Such lipids are described for example, in van der Lui et al ("A new class of anticancer alkylphospholipids uses lipid rafts as membrane gateways to induce apoptosis in lymphoma cells" Mol Cancer Ther 2007; 6(8), 2007; hereby expressly incorporated by reference in its entirety). In some alternatives of the lipids described herein, a choline within the polar head group can be substituted with a piperidine moiety. In some alternatives, the lipid is an anticancer alkylphospholipid. Anticancer phospholipids are described by vander Lui et al. ("A new class of anticancer alkylphospholipids uses lipid rafts as membrane gateways to induce apoptosis in lymphoma cells" Mol Cancer Ther 2007; 6(8), 2007; hereby expressly incorporated by reference in its entirety).

In some alternatives, the lipids provided herein are synthetic and structurally related antitumor agents that interact with a cell membrane. These types of synthetic lipids are alkylphospholipids and are described by e.g., van Blitterswijk et al. ("Anticancer mechanisms and clinical application of alkylphopholipids" Biochimica et Biophysica Acta 1831 (2013) 663-674; hereby incorporated by reference in its entirety herein). Without being limiting, the synthetic alkylphospholipids can include edelfosine, miltefosine, perifosine, erucylphosphocholine or Erufosine. In some alternatives, the lipid is edelfosine, miltefosine, perifosine, erucylphosphocholine or Erufosine. In some alternatives, the lipid is a stable analog of lysophosphatidylcholine. In some alternatives, the lipid is a thio-ether variant of edelfosine, or 1-hexadecylthio-2-methoxymethyl-rac-glycero-3-phosphocholine. In some alterantives, the lipid is LysoPC, edelfosine, Ilmofosine, Miltefosine, Perifosine, Erucylphochocholine, or Erufosine.

"Polar-head group" as described herein, is the hydrophilic group of a lipid, such as a phospholipid. "Phospholipids" as described herein are a specific class of lipids that can form lipid bilayers due to their amphiphilic characteristic. The phospholipid molecule comprises at least one hydrophobic fatty acid "tail" and a hydrophilic "head" or "polar-head group." In the alternative herein, the phospholipid or phospholipid ether comprises a polar-head group. In some alternatives, the polar-head group comprises phosphocholine, a piperidine moiety or a trimethylarseno-ethyl-phosphate moiety. In some alternatives, the lipid comprises a target moiety and the CAR is joined to or is configured to join to said lipid through an interaction with said target moiety. In some alternatives, the lipid comprises a polar-head group (e.g., comprising an aromatic ring) and a carbon alkyl chain. In some alternatives herein, a complex is provided, wherein the complex comprises one or more of said lipids. In some alternatives, the lipid comprises a polar head group. In some alternatives, the lipid is a phospholipid ether. In some alternatives, the phospholipid ether comprises a target moiety and the CAR is joined to or is configured to join to said phospholipid ether through an interaction and/or binding with said target moiety. In some alternatives, the phospholipid ether comprises a polar-head group and a carbon alkyl chain. In some alternatives, the polar head group comprises a choline, a phosphatidylcholine, sphingomyelin, phosphoethanolamine group, an oligosaccharide residue, a sugar residue, phosphatidyl serine or phosphatidyl inositol. In some alternatives, the polar head group comprises phosphocholine, a piperidine moiety or a trimethylarseno-ethyl-phosphate moiety. In some alternatives, the lipid is a phospholipid ether. In some alternatives, the sugar is a glycerol or sugar alcohol. In some alternatives, the polar head group comprises a sugar group. In some alternatives, the lipid comprises a mannose-containing head group. In some alternatives, the polar head group comprises sphingosine. In some alternatives, the polar head group comprises a glucose. In some alternatives, the polar head group comprises a di-, tri- or tetra-saccharide. In some alternatives, the lipid is a glucosylcerebroside. In some alternatives, the lipid is a lactosylceramide. In some alternatives, the lipid is a glycolipid. In some alternatives, the glycolipid comprises sugar units, such as n-glucose, n-galactose or N-actyl-n-glactosamine. In some alternatives, the lipid comprises a hydrocarbon ring such as a sterol.

In some alternatives, the polar head group of the lipid comprises glycerol or a sugar alcohol. In some alternatives, the polar head group of the lipid comprises a phosphate group. In some alternatives, the polar head group of the lipid comprises choline. In some alternatives, the lipid is a phosphatidylethanolomine. In some alternatives, the lipid is a phosphatidylinositol. In some alternatives, the lipid comprises a sphingoid base backbone. In some alternatives, the lipid comprises a sterol lipid, such as cholesterol or its derivatives. In some alternatives, the lipid comprises saccharolipids. In some alternatives, the polar head group comprises choline, phosphate and/or glycerol.

In some alternatives, the lipid is a glycolipid. In some alternatives, the lipid comprises a sugar. In some alternatives, the lipid is derived from sphingosine. In some alternatives, the lipid is a glycerol-glycolipid or a sphingoglycolipid.

In some alternatives, the lipid is an ether lipid with branched hydrophobic chains.

"Saturated" as described herein is a fatty acid molecule, in which there are no double bonds within the carbon molecules. Unsaturated as described herein indicates that there are one or more double bonds in a fatty acid chain. In some alternatives herein a complex comprising a lipid is provided. In some alternatives, the lipid comprises a fatty acid chain, in which the fatty acid is saturated or unsaturated.

"Alkyl" as described herein, is an alkyl substituent that has a missing hydrogen.

An "alkenyl" group is an unsaturated hydrocarbon that contains at least one carbon-carbon double bond.

An "alkynyl" group is an unsaturated hydrocarbon containing at least one carbon-carbon triple bond.

"Terpenoid" as described herein, is a molecule that is derived from five carbon isoprene units. Steroids and sterols can be produced from terpenoid precursors. For example, steroids and cholesterol can be biosynthesized by terpenoid precursors.

"Phospholipid ether" as described herein is a lipid in which one or more of the carbon atoms on a polar head group are bonded to an alkyl chain via an ether linkage, as opposed to the more common ester linkage. In some alternatives, the polar head group is a glycerol.

Several types of "spacers" are described herein. The spacer for a chimeric antigen receptor refers to a polypeptide spacer, which spacer length is configured to or is selected for its ability to promote an increase in binding or interaction with a chimeric antigen receptor or to reduce or minimizes an adverse side effect associated with CAR T cell therapy. In some embodiments, a short spacer domain of a CAR has about 12 amino acids or less but greater than 1 amino acid and comprises all or a portion of a IgG4 hinge region sequence or variant thereof. In some embodiments, an intermediate spacer domain of a CAR has about 119 amino acids or less but greater than 1 amino acid and comprises all or a portion of a IgG4 hinge region sequence and a CH3 region or variant thereof. In some embodiments, a long spacer domain of a CAR has about 229 amino acids or less but greater than 1 amino acid and comprises all or a portion of a IgG4 hinge region sequence, a CH2 region, and a CH3 region or variant thereof. With regards to the lipid, the lipid can also comprise a spacer that separates the target moiety from the lipid and is bound to the polar-head group of the lipid. The spacer of the lipid can comprise a PEG spacer, a Hapten spacer, a small peptide or an alkane chain. In some alternatives, the hapten spacer comprises two haptens (hapten (2x) spacer). In some alternatives, the lipid comprises a hydrophobic group, such as an alkane chain. In some alternatives, the alkane chain can comprise 2, 3, 4, 5, 6, 7, 8, 9, 10, 11, 12, 13, 14, 15, 16, 17, or 18 carbons, or any number of carbons between a range defined by any two aforementioned values. In some alternatives, the PEG spacer comprises 1, 2, 3, 4, 5, 6, 7, 8, 9, 10, 11, 12, 13, 14, 15 or 16 PEG molecules, or any amount of PEG molecules that is within a range defined by any two aforementioned values.

"Hapten" as described herein is a small molecule that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this. In some embodiments, a hapten is a small molecule binding moiety, which can be bound by or have specificity towards a scFv or antibody.

In some alternatives herein, the cells provided are cytotoxic T lymphocytes. "Cytotoxic T lymphocyte" (CTL) as used herein refers to a T lymphocyte that expresses CD8 on the surface thereof (e.g., a $CD8^+$ T cell). In some alternatives, such cells are preferably "memory" T cells (TM cells) that are antigen-experienced. In some alternatives, the cell is a precursor T cell. In some alternatives, the precursor T cell is a hematopoietic stem cell. In some alternatives, the cell is a CD8+T cytotoxic lymphocyte cell selected from the group consisting of naïve CD8+ T cells, central memory CD8+ T cells, effector memory CD8+ T cells and bulk CD8+ T cells. In some alternatives, the cell is a CD4+T helper lymphocyte cell that is selected from the group consisting of naïve CD4+ T cells, central memory CD4+ T cells, effector memory CD4+ T cells, and bulk CD4+ T cells.

"Masking moiety" as used herein, refers to a moiety on a lipid ether that is bound to the target moiety. The masking moiety functions as a protective group to prevent recognition of the lipid's target moiety by blocking binding and recognition of a chimeric antigen receptor that is specific for the target moiety. When the lipid is integrated into a cell, wherein the cell exists in a tumor environment or site of reactive oxygen species, the masking moiety can be self-cleaved, thus allowing binding, interaction and/or recognition of the target moiety by the chimeric antigen receptor. In some alternatives, the lipid is a phospholipid ether. In some alternatives, the masking moiety comprises a phenolic hydroxyl group or PEG. In some alternatives, the phenolic hydroxyl group is bound to a hydroxyl on a xanthene moiety of fluorescein. In some alternatives, the masking moiety is bound to the target moiety by a cleavable moiety, which is optionally configured to be specifically cleavable in a tumor microenvironment. In some alternatives, the cleavable moiety, which is configured to be cleavable in a tumor microenvironment, is cleaved by a reactive oxygen species reaction, an acidic pH, hypoxia, or nitrosylation. In some alternatives, the phospholipid ether comprises a target moiety and the CAR is joined to said phospholipid ether through an interaction with said target moiety. In some alternatives, the phospholipid ether comprises a polar-head group and a carbon alkyl chain.

"Cancer," as described herein, is a group of diseases involving abnormal cell growth with the potential to invade or spread to other parts of the body. Subjects that can be addressed using the methods described herein include subjects identified or selected as having cancer, including but not limited to colon, lung, liver, breast, renal, prostate, ovarian, skin (including melanoma), bone, leukemia, multiple myeloma, or brain cancer, etc. Such identification and/or selection can be made by clinical or diagnostic evaluation. In some alternatives, the tumor associated antigens or molecules are known, such as melanoma, breast cancer, brain cancer, squamous cell carcinoma, colon cancer, leukemia, myeloma, or prostate cancer. Examples include but are not limited to B cell lymphoma, breast cancer, brain cancer, prostate cancer, and/or leukemia. In some alternatives, one or more oncogenic polypeptides are associated with kidney, uterine, colon, lung, liver, breast, renal, prostate, ovarian, skin (including melanoma), bone, brain cancer, adenocarcinoma, pancreatic cancer, chronic myelogenous leukemia or leukemia. In some alternatives, a method of treating, ameliorating, or inhibiting a cancer in a subject is provided. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the subject that receives one of the therapies described herein is also selected to receive an additional cancer therapy, which can include a cancer therapeutic, radiation, chemotherapy, or a cancer therapy drug. In some alternatives, the cancer therapy drug provided comprises Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine or Zoledronic acid.

"Tumor microenvironment" as described herein is a cellular environment, wherein a tumor exists. Without being limiting, the tumor microenvironment can include surrounding blood vessels, immune cells, fibroblasts, bone marrow-derived inflammatory cells, lymphocytes, signaling molecules or the extracellular matrix (ECM).

In some embodiments, the method includes human tumor therapy in which patients receive infusions of FL-PLE or derivatives thereof in combination with infusions of FL-specific CAR T cells. In this scenario, this system represents a universal target antigen used in combination with a universal CAR and/or universal CAR expressing anti-tumor effector cells. In some embodiments, a PLE (18C alkyl chain) having a FL appended CAR recognition element, which is appended to the polar head group's choline via three repeat PEG spacers is provided. An antiFL CAR library may be generated with different single chain variable fragments (scFvs), such as 6 or more different scFvs, with dissociation constants ranging from 200 fM to 10 nM, such as 200 fM, 210 fM, 220 fM, 230 fM, 240 fM, 250 fM, 260 fM, 270 fM, 280 fM, 290 fM, 300 fM, 400 fM, 500 fM, 600 fM, 700 fM, 800 fM, 900 fM, 1 pM, 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, or 10 nm, or an amount within a range defined by any two of the aforementioned values, which connect the scFv to the spacing element of the CAR. Each scFv binds FL in a slightly different manner. Without wishing to be bound by theory, the binding of scFv to FL is partially due to the difference in binding affinities through mutations in the binding pocket and due to the fact that some scFvs were derived from phage display compared to yeast display. In some embodiments, three different spacers (all derived from antibody components) may be used, including, for example: long, IgG4 hinge connected to a CH2 domain to a CH3 domain; medium, IgG4 hinge connected to a CH3 domain; and short, IgG4 hinge only. In some embodiments, only FL-specific scFv CAR T cells with the correct orientation and spacer length exhibit redirected anti-tumor function in both in vitro and in vivo tumors loaded with FL PLE-CTCTs. Moreover, the shape and size of the scFv's binding pocket can play a role in how well the CAR can activate.

Some embodiments provided herein relate to a FL-specific CAR T cell comprising a targeting and recognition domain presented in a correct orientation with spacing and a binding affinity selected to create a desired T cell response. In some embodiments, the spacing is selected for generating a T cell response in the specific cells of interest. In some embodiments, the binding affinity is selected for generating a T cell response in the specific cells of interest. In some embodiments, different tumors or cells benefit from different orientation, different spacer lengths, and affinities of CAR T cells to allow for desired CAR T cell responses. Therefore, some embodiments provided herein relate to generating a desired or selected combination of orientation, spacer length, and binding affinity for a selected therapy.

In some embodiments, an indication or measure of successful CAR T cells in vitro include cell lysis and the production of cytokines. As described herein in further detail, short spacer CARs typically do not produce cytokines; whereas the long spacer CARs produce a large quantity of cytokines.

In some embodiments, an antiFL(4D5Flu) CAR, which comprises SEQ ID NO: 4, and which is not able to produce cytokines with FL-PLE, is provided; whereas when cells are labeled with FL by another approach the antiFL(4D5Flu) CAR produces cytokines highlighting that the orientation of scFv to FL moiety of FL-PLE is an important and previously unrecognized variable in T cell activity. In some embodiments, lowering the dissociation constant, such as improving the binding affinity, does not necessarily improve the activation of the CAR. In some embodiments, asymmetric T cell antitumor reactivity does not correlate with scFv KD. In some embodiments, asymmetric T cell antitumor reactivity may be spacer length dependent. In some embodiments, an antiFL(FITC-E2 Mut2) CAR, which comprises SEQ ID NO: 1, is a robust CAR, which could not have been predicted from any prior knowledge of CAR structure function or scFv studies. In contrast, the field teaches that the highest scFv affinity results in the best CAR.

In some embodiments, FL-PLE administered to tumor-bearing mammals serves as a generic tumor-targeting agent that is retained on the tumor cell plasma membrane for recognition by FL-specific CAR T cells. Provided herein is the identification of a FL-specific CAR with unexpected T cell signaling robustness upon engagement of tumor cells loaded with FL-PLE. This disclosure relates, in some embodiments, to the full development of a pharmaceutical-grade FL-PLE to be used in conjunction with a CAR T cell product, including in a kit. Other haptens could replace FL with CAR designed to react with these PLEs.

TABLE 1 lists certain example sequences useful with embodiments provided herein.

TABLE 1

| SEQ ID NO.<br>(description) | SEQUENCE |
|---|---|
| SEQ ID NO: 01<br>(scFv of antiFL<br>(FITCE2 Mut2 CAR) | SVLTQPSSVSAAPGQKVTISCSGSTSNIGNNYVSWYQQHPGKAPKLMIY<br>DVSKRPSGVPDRFSGSKSGNSASLDISGLQSEDEADYYCAAWDDSLSEF<br>LFGTGTKLTVLGGGGGSGGGGSGGGGSQVQLVESGGNLVQPGGSLRLSC<br>AASGFTFGSFSMSWVRQAPGGGLEWVAGLSARSSLTHYADSVKGRFTIS<br>RDNAKNSVYLQMNSLRVEDTAVYYCARRSYDSSGYWGHFASYMDVWGQG<br>TLVTVS |
| SEQ ID NO: 02<br>(antiFL(4M5.3) CAR) | DVVMTQTPLSLPVSLGDQASISCRSSQSLVHSNGNTYLRWYLQKPGQSPKVLI<br>YKVSNRVSGVPDRFSGSGSGTDFTLKINRVEAEDLGVYFCSQSTHVPWTFGGG<br>TKLEIKSSADDAKKDAAKKDDAKKDDAKKDGGVKLDETGGGLVQPGGAMKL<br>SCVTSGFTFGHYWMNWVRQSPEKGLEWVAQFRNKPYNYETYYSDSVKGRFT<br>ISRDDSKSSVYLQMNNLRVEDTGIYYCTGASYGMEYLGQGTSVTVS |
| SEQ ID NO: 03<br>(scFv of<br>antiFL(4420) CAR) | DVVMTQTPLSLPVSLGDQASISCRSSQSLVHSQGNTYLRWYLQKPGQSPKVLI<br>YKVSNRFSGVPDRFSGSGSGTDFTLKISRVEAEDLGVYFCSQSTHVPWTFGGG<br>TKLEIGGGGSGGGGSGGGGSEVKLDETGGGLVQPGRPMKLSCVASGFTFSDY<br>WMNWVRQSPEKGLEWVAQIRNKPYNYETYYSDSVKGRFTISRDDSKSSVYLQ<br>MNNLRVEDMGIYYCTGSYYGMDYWGQGTSVTVSS |
| SEQ ID NO: 04<br>(scFv of<br>antiFL(4D5Flu) CAR) | DYKDIQMTQSPSSLSASVGDRVTITCRASQSLVHSQGNTYLRWYQQKPGK<br>APKVLIYKVSNRFSGVPSRFSGSGSGTDFTLTISSLQPEDFATYYCQQST<br>HVPWTFGQGTKVELKRAGGGGSGGGGSGGGGSSGGGSGGGGSGGGGSEVQ<br>LVESGGGLVQPGGSLRLSCAASGFTFSDYWMNWVRQAPGKGLEWVAQIRN<br>KPYNYETYYADSVKGRFTISRDTSKNTVYLQMNSLRAEDTAVYYCTGSYY<br>GMDYWGQGTLVTVSS |
| SEQ ID NO: 05<br>(scFv of<br>antiFL(FITCE2) CAR) | SVLTQPSSVSAAPGQKVTISCSGSTSNIGNNYVSWYQQHPGKAPKLMIYDV<br>SKRPSGVPDRFSGSKSGNSASLDISGLQSEDEADYYCAAWDDSLSEFLFGT<br>GTKLTVLGGGGGSGGGGSGGGGSQVQLVESGGNLVQPGGSLRLSCAASGFT<br>FGSFSMSWVRQAPGGGLEWVAGLSARSSLTHYADSVKGRFTISRDNAKNSV<br>YLQMNSLRVEDTAVYYCARRSYDSSGYWGHFYSYMDVWGQGTLVTVS |
| SEQ ID NO: 06<br>(scFv of<br>antiFL(FITCE2<br>HisH131Ala)) | SVLTQPSSVSAAPGQKVTISCSGSTSNIGNNYVSWYQQHPGKAPKLMIYDV<br>SKRPSGVPDRFSGSKSGNSASLDISGLQSEDEADYYCAAWDDSLSEFLFGT<br>GTKLTVLGGGGGSGGGGSGGGGSQVQLVESGGNLVQPGGSLRLSCAASGFT<br>FGSFSMSWVRQAPGGGLEWVAGLSARSSLTHYADSVKGRFTISRDNAKNSV<br>YLQMNSLRVEDTAVYYCARRSYDSSGYWGAFYSYMDVWGQGTLVTVS |
| SEQ ID NO: 07<br>(IgG4 hinge<br>connected to a CH2<br>domain to a CH3<br>domain spacer) | ESKYGPPCPPCPAPEFDGGPSVFLFPPKPKDTLMISRTPEVTCVVVDVSQE<br>DPEVQFNWYVDGVEVHNAKTKPREEQFQSTYRVVSVLTVLHQDWLNGKEYK<br>CKVSNKGLPSSIEKTISKAKGQPREPQVYTLPPSQEEMTKNQVSLTCLVKG<br>FYPSDIAVEWESNGQPENNYKTTPPVLDSDGSFFLYSRLTVDKSRWQEGNV<br>FSCSVMHEALHNHYTQKSLSLSLGK |
| SEQ ID NO: 08<br>(IgG4 hinge<br>connected to a CH3<br>domain spacer) | ESKYGPPCPPCPGQPREPQVYTLPPSQEEMTKNQVSLTCLVKGFYPSDIAV<br>EWESNGQPENNYKTTPPVLDSDGSFFLYSRLTVDKSRWQEGNVFSCSVMHE<br>ALHNHYTQKSLSLSLGK |

TABLE 1-continued

| SEQ ID NO. (description) | SEQUENCE |
|---|---|
| SEQ ID NO: 09 (IgG4 hinge only spacer) | ESKYGPPCPPCP |
| SEQ ID NO: 10 (E2 anti-fluorescein antibody fragment CAR nucleic acid sequence) | ATGCTTCTCCTGGTGACAAGCCTTCTGCTCTGTGAGTTACCACACCCAGCAT<br>TCCTCCTGATCCCAAGCGTGCTGACACAGCCTAGCTCCGTGTCTGCCGCCCC<br>TGGCCAGAAAGTGACCATCAGCTGTAGCGGCAGCACCAGCAACATCGGCA<br>ACAACTACGTGTCCTGGTATCAGCAGCACCCCGGCAAGGCCCCCAAGCTGA<br>TGATCTACGACGTGTCCAAGCGGCCCAGCGGCGTGCCCGATAGATTTTCCG<br>GCAGCAAGAGCGGCAACAGCGCCAGCCTGGATATCAGCGGCCTGCAGTCT<br>GAGGACGAGGCCGACTACTATTGCGCCGCCTGGGACGATAGCCTGAGCGA<br>GTTCCTGTTTGGCACCGGCACCAAGCTGACAGTGCTGGGCGGAGGCGGAG<br>GATCTGGCGGCGGAGGAAGTGGCGGAGGGGGATCTCAGGTGCAGCTGGT<br>GGAAAGCGGCGGCAACCTGGTGCAGCCTGGCGGATCTCTGAGACTGAGCT<br>GTGCCGCCAGCGGCTTCACCTTCGGCAGCTTCAGCATGAGCTGGGTGCGC<br>CAGGCTCCTGGGGAGGACTGGAATGGGTGGCAGGACTGAGCGCCAGAA<br>GCAGCCTGACCCACTACGCCGATAGCGTGAAGGGCCGGTTCACCATCAGC<br>CGGGACAACGCCAAGAACAGCGTGTACCTGCAGATGAACAGCCTGCGGGT<br>GGAAGATACCGCCGTGTACTACTGCGCCAGACGGTCCTACGACAGCAGCG<br>GCTACTGGGGCCACTTCTACAGCTACATGGACGTGTGGGGCCAGGGCACC<br>CTCGTGACAGTGTCTGAGAGCAAGTACGGACCGCCCTGCCCCCCTTGCCCT<br>GCCCCCGAGTTCGACGGCGGACCCAGCGTGTTCCTGTTCCCCCCCAAGCCC<br>AAGGACACCCTGATGATCAGCCGGACCCCCGAGGTGACCTGCGTGGTGGT<br>GGACGTGAGCCAGGAAGATCCCGAGGTCCAGTTCAATTGGTACGTGGACG<br>GCGTGGAAGTGCACAACGCCAAGACCAAGCCCAGAGAGGAACAGTTCCA<br>GAGCACCTACCGGGTGGTGTCTGTGCTGACCGTGCTGCACCAGGACTGGC<br>TGAACGGCAAAGAATACAAGTGCAAGGTGTCCAACAAGGGCCTGCCCAGC<br>AGCATCGAAAAGACCATCAGCAAGGCCAAGGGCCAGCCTCGCGAGCCCCA<br>GGTGTACACCCTGCCTCCCTCCCAGGAAGAGATGACCAAGAACCAGGTGT<br>CCCTGACCTGCCTGGTGAAGGGCTTCTACCCCAGCGACATCGCCGTGGAGT<br>GGGAGAGCAACGGCCAGCCTGAGAACAACTACAAGACCACCCCTCCCGTG<br>CTGGACAGCGACGGCAGCTTCTTCCTGTACAGCCGGCTGACCGTGGACAA<br>GAGCCGGTGGCAGGAAGGCAACGTCTTTAGCTGCAGCGTGATGCACGAG<br>GCCCTGCACAACCACTACACCCAGAAGAGCCTGAGCCTGTCCCTGGGCAA<br>GATGTTCTGGGTGCTGGTGGTGGTGGGCGGGGTGCTGGCCTGCTACAGCC<br>TGCTGGTGACAGTGGCCTTCATCATCTTTTGGGTGAAACGGGGCAGAAAG<br>AAACTCCTGTATATATTCAAACAACCATTTATGAGACCAGTACAAACTACTC<br>AAGAGGAAGATGGCTGTAGCTGCCGATTTCCAGAAGAAGAAGAAGGAGG<br>ATGTGAACTGCGGGTGAAGTTCAGCAGAAGCGCCGACGCCCCTGCCTACC<br>AGCAGGGCCAGAATCAGCTGTACAACGAGCTGAACCTGGGCAGAAGGGA<br>AGAGTACGACGTCCTGGATAAGCGGAGAGGCCGGGACCCTGAGATGGGC<br>GGCAAGCCTCGGCGGAAGAACCCCCAGGAAGGCCTGTATAACGAACTGCA<br>GAAAGACAAGATGGCCGAGGCCTACAGCGAGATCGGCATGAAGGGCGAG<br>CGGAGGCGGGCAAGGGCCACGACGGCCTGTATCAGGGCCTGTCCACCG<br>CCACCAAGGATACCTACGACGCCCTGCACATGCAGGCCCTGCCCCCAAGGC<br>TCGAGGGCGGCGGAGAGGGCAGAGGAAGTCTTCTAACATGCGGTGACGT<br>GGAGGAGAATCCCGGCCCTAGGATGCTTCTCCTGGTGACAAGCCTTCTGCT<br>CTGTGAGTTACCACACCCAGCATTCCTCCTGATCCCACGCAAAGTGTGTAAC<br>GGAATAGGTATTGGTGAATTTAAAGACTCACTCTCCATAAATGCTACGAAT<br>ATTAAACACTTCAAAAACTGCACCTCCATCAGTGGCGATCTCCACATCCTGC<br>CGGTGGCATTTAGGGGTGACTCCTTCACACATACTCCTCCTCTGGATCCACA<br>GGAACTGGATATTCTGAAAACCGTAAAGGAAATCACAGGGTTTTTGCTGAT<br>TCAGGCTTGGCCTGAAAACAGGACGGACCTCCATGCCTTTGAGAACCTAGA<br>AATCATACGCGGCAGGACCAAGCAACATGGTCAGTTTTCTCTTGCAGTCGT<br>CAGCCTGAACATAACATCCTTGGGATTACGCTCCCTCAAGGAGATAAGTGA<br>TGGAGATGTGATAATTTCAGGAAACAAAAATTTGTGCTATGCAAATACAAT<br>AAACTGGAAAAAACTGTTTGGGACCTCCGGTCAGAAAACCAAAATTATAA<br>GCAACAGAGGTGAAAACAGCTGCAAGGCCACAGGCCAGGTCTGCCATGCC<br>TTGTGCTCCCCCGAGGGCTGCTGGGGCCCGGAGCCCAGGGACTGCGTCTC<br>TTGCCGGAATGTCAGCCGAGGCAGGGAATGCGTGGACAAGTGCAACCTTC<br>TGGAGGGTGAGCCAAGGGAGTTTGTGGAGAACTCTGAGTGCATACAGTG<br>CCACCCAGAGTGCCTGCCTCAGGCCATGAACATCACCTGCACAGGACGGG<br>GACCAGACAACTGTATCCAGTGTGCCCACTACATTGACGGCCCCCACTGCG<br>TCAAGACCTGCCCGGCAGGAGTCATGGGAGAAAACAACACCCTGGTCTGG<br>AAGTACGAGACGCCGGCCATGTGTGCCACCTGTGCCATCCAAACTGCACC<br>TACGGATGCACTGGGCCAGGTCTTGAAGGCTGTCCAACGAATGGGCCTAA<br>GATCCCGTCCATCGCCACTGGGATGGTGGGGCCCTCCTCTTGCTGCTGGT<br>GGTGGCCCTGGGGATCGGCCTCTTCATGTGA |
| SEQ ID NO: 11 (E2 anti-fluorescein antibody fragment CAR amino acid sequence) | MLLLVTSLLLCELPHPAFLLIPSVLTQPSSVSAAPGQKVTISCSGSTSNIGN<br>NYVSWYQQHPGKAPKLMIYDVSKRPSGVPDRFSGSKSGNSASLDISGLQSED<br>EADYCAAWDDSLSEFLFGTGTKLTVLGGGGSGGGGSGGGGSQVQLVESGG<br>NLVQPGGSLRLSCAASGFTFGSFSMSWVRQAPGGGLEWVAGLSARSSLTHYA<br>DSVKGRFTISRDNAKNSVYLQMNSLRVEDTAVYYCARRSYDSSGYWGHFYSY<br>MDVWGQGTLVTVSESKYGPPCPPCPAPEFDGGPSVFLFPPKPKDTLMISRTP<br>EVTCVVVDVSQEDPEVQFNWYVDGVEVHNAKTKPREEQFQSTYRVVSVLTVL |

TABLE 1-continued

| SEQ ID NO. (description) | SEQUENCE |
|---|---|
| | HQDWLNGKEYKCKVSNKGLPSSIEKTISKAKGQPREPQVYTLPPSQEEMTKN QVSLTCLVKGFYPSDIAVEWESNGQPENNYKTTPPVLDSDGSFFLYSRLTVD KSRWQEGNVFSCSVMHEALHNHYTQKSLSLSLGKMFWVLVVVGGVLACYSLL VTVAFIIFWVKRGRKKLLYIFKQPFMRPVQTTQEEDGCSCRFPEEEEGGCEL RVKFSRSADAPAYQQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPRLEGGGEGRGSLLTCGDVEENPGPRMLLLVTSLLLCELPHPAFLL IPRKVCNGIGIGEFKDSLSINATNIKHFKNCTSISGDLHILPVAFRGDSFTH TPPLDPQELDILKTVKEITGFLLIQAWPENRTDLHAFENLEIIRGRTKQHGQ FSLAVVSLNITSLGLRSLKEISDGDVIISGNKNLCYANTINWKKLFGTSGQK TKIISNRGENSCKATGQVCHALCSPEGCWGPEPRDCVSCRNVSRGRECVDKC NLLEGEPREFVENSECIQCHPECLPQAMNITCTGRGPDNCIQCAHYIDGPHC VKTCPAGVMGENNTLVWKYADAGHVCHLCHPNCTYGCTGPGLEGCPTNGPKI PSIATGMVGALLLLLVVALGIGLFM |
| SEQ ID NO: 12 (4M5.3-CAR amino acid sequence) | MLLLVTSLLLCELPHPAFLLIPDVVMTQTPLSLPVSLGDQASISCRSSQS LVHSNGNTYLRWYLQKPGQSPKVLIYKVSNRVSGVPDRFSGSGSGTDFTL KINRVEAEDLGVYFCSQSTHVPWTFGGGTKLEIKSSADDAKKDAAKKDDA KKDDAKKDGGVKLDETGGGLVQPGGAMKLSCVTSGFTFGHYWMNWVRQSP EKGLEWVAQFRNKPYNYETYYSDSVKGRFTISRDDSKSSVYLQMNNLRVE DTGIYYCTGASYGMEYLGQGTSVTVSESKYGPPCPPCPAPEFDGGPSVFL FPPKPKDTLMISRTPEVTCVVVDVSQEDPEVQFNWYVDGVEVHNAKTKPR EEQFQSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNYK TTPPVLDSDGSFFLYSRLTVDKSRWQEGNVFSCSVMHEALHNHYTQKSLS LSLGKMFWVLVVVGGVLACYSLLVTVAFIIFWVKRGRKKLLYIFKQPFMR PVQTTQEEDGCSCRFPEEEEGGCELRVKFSRSADAPAYQQGQNQLYNELN LGRREEYDVLDKRRGRDPEMGGKPRRKNPQEGLYNELQKDKMAEAYSEIG MKGERRRGKGHDGLYQGLSTATKDTYDALHMQALPPRLEGGGEGRGSLLT CGDVEENPGPRMLLLVTSLLLCELPHPAFLLIPRKVCNGIGIGEFKDSLS INATNIKHFKNCTSISGDLHILPVAFRGDSFTHTPPLDPQELDILKTVKE ITGFLLIQAWPENRTDLHAFENLEIIRGRTKQHGQFSLAVVSLNITSLGL RSLKEISDGDVIISGNKNLCYANTINWKKLFGTSGQKTKIISNRGENSCK ATGQVCHALCSPEGCWGPEPRDCVSCRNVSRGRECVDKCNLLEGEPREFV ENSECIQCHPECLPQAMNITCTGRGPDNCIQCAHYIDGPHCVKTCPAGVM GENNTLVWKYADAGHVCHLCHPNCTYGCTGPGLEGCPTNGPKIPSIATGM VGALLLLLVVALGIGLFM |
| SEQ ID NO: 13 (4M 5.3-CAR nucleotide seq uence) | ATGCTTCTCCTGGTGACAAGCCTTCTGCTCTGTGAGTTACCACACCCAGCAT TCCTCCTGATCCCAGACGTTGTAATGACCCAGACCCCTCTGTCTCTCCCGT AAGCTTGGGCGACCAGGCGAGCATCTCTTGTCGGTCTTCCCAGTCCCTGGT CCATTCAAACGGCAATACTTACTTGCGGTGGTACTTGCAGAAGCCCGGTCA ATCCCCAAAAGTGCTGATATACAAGGTTAGCAATCGGGTCAGTGGAGTGC CCGACCGCTTCAGCGGAAGCGGATCCGGGACTGACTTCACTCTGGAAGATC AACCCGGGTAGAAGCTGAAGACCTGGGGGTGTACTTCTGCTCTCAGTCAAC ACACGTGCCATGGACCTTTGGAGGTGGCACCAAGCTGGAAATCAAATCAT CAGCGGACGATGCCAAAAAGGACGCGGCCAAGAAGGACGATGCCAAGAA GGATGATGCTAAAAAGGATGGCGGAGTCAAATTGGACGAGACAGGCGGG GGACTGGTGCAGCCCGGCGGTGCCATGAAACTGTCTTGTGTGACCAGCGG CTTTACCTTCGGGCATTATTGGATGAACTGGGTGCGACAGTCTCCAGAGAA AGGGCTCGAGTGGGTGGCCCAGTTTCGAAATAAACCGTACAATTATGAGA CCTACTATTCAGATTCTGTGAAAGGGCGCTTCACTATTTCACGCGACGACA GCAAAAGTTCCGTCTACCTTCAGATGAACAACCTTAGAGTGGAGGATACCG GAATATACTACTGCACGGGTGCCAGTTATGGCATGGAGTACTTGGGGCAG GGGACATCTGTGACCGTTTCTGAGAGCAAGTACGGACCGCCCTGCCCCCT TGCCCTGCCCCCAGAGTTCGACGGCGGACCCAGCGTGTTCCTGTTCCCCCC AAGCCCAAGGACACCCTGATGATCAGCCGGACCCCCGAGGTGACCTGCGT GGTGGTGGACGTGAGCCAGGAAGATCCCGAGGTCCAGTTCAATTGGTACG TGGACGGCGTGGAAGTGCACAACGCCAAGACCAAGCCCAGAGAGGAACA GTTCCAGAGCACCTACCGGGTGGTGTCTGTGCTGACCGTGCTGCACCAGG ACTGGCTGAACGGCAAAGAATACAAGTGCAAGGTGTCCAACAAGGGCCTG CCCAGCAGCATCGAAAAGACCATCAGCAAGGCCAAGGGCCAGCCTCGCGA GCCCCAGGTGTACACCCTGCCTCCCTCCCAGGAAGAGATGACCAAGAACCA GGTGTCCCTGACCTGCCTGGTGAAGGGCTTCTACCCCAGCGACATCGCCGT GGAGTGGGAGAGCAACGGCCAGCCTGAGAACAACTACAAGACCACCCCTC CCGTGCTGGACAGCGACGGCAGCTTCTTCCTGTACAGCCGGCTGACCGTG GACAAGAGCCGGTGGCAGGAAGGCAACGTCTTTAGCTGCAGCGTGATGCA CGAGGCCCTGCACAACCACTACACCCAGAAGAGCCTGAGCCTGTCCCTGG GCAAGATGTTCTGGGTGCTGGTGGTGGTGGGCGGGGTGCTGGCCTGCTAC AGCCTGCTGGTGACAGTGGCCTTCATCATCTTTTGGGTGAAACGGGGCAG AAAGAAACTCCTGTATATATTCAAACAACCATTTATGAGACCAGTACAAAC TACTCAAGAGGAAGATGGCTGTAGCTGCCGATTTCCAGAAGAAGAAGAG GAGGATGTGAACTGCGGGTGAAGTTCAGCAGAAGCGCCGACGCCCCTGCC TACCAGCAGGGCCAGAATCAGCTGTACAACGAGCTGAACCTGGGCAGAAG GGAAGAGTACGACGTCCTGGATAAGCGGAGAGGCCGGGACCCTGAGATG GGCGGCAAGCCTCGGCGGAAGAACCCCCAGGAAGGCCTGTATAACGAACT GCAGAAAGACAAGATGGCCGAGGCCTACAGCGAGATCGGCATGAAGGGC |

TABLE 1-continued

| SEQ ID NO.<br>(description) | SEQUENCE |
|---|---|
| | GAGCGGAGGCGGGGCAAGGGCCACGACGGCCTGTATCAGGGCCTGTCCA<br>CCGCCACCAAGGATACCTACGACGCCCTGCACATGCAGGCCCTGCCCCCAA<br>GGCTCGAGGGCGGCGGAGAGGGCAGAGGAAGTCTTCTAACATGCGGTGA<br>CGTGGAGGAGAATCCCGGCCCTAGGATGCTTCTCCTGGTGACAAGCCTTCT<br>GCTCTGTGAGTTACCACACCCAGCATTCCTCCTGATCCCACGCAAAGTGTGT<br>AACGGAATAGGTATTGGTGAATTTAAAGACTCACTCTCCATAAATGCTACG<br>AATATTAAACACTTCAAAAACTGCACCTCCATCAGTGGCGATCTCCACATCC<br>TGCCGGTGGCATTTAGGGGTGACTCCTTCACACATACTCCTCCTCTGGATCC<br>ACAGGAACTGGATATTCTGAAAACCGTAAAGGAAATCACAGGGTTTTTGCT<br>GATTCAGGCTTGGCCTGAAAACAGGACGGACCTCCATGCCTTTGAGAACCT<br>AGAAATCATACGCGGCAGGACCAAGCAACATGGTCAGTTTTCTCTTGCAGT<br>CGTCAGCCTGAACATAACATCCTTGGGATTACGCTCCCTCAAGGAGATAAG<br>TGATGGAGATGTGATAATTTCAGGAAACAAAAATTTGTGCTATGCAAATAC<br>AATAAACTGGAAAAAACTGTTTGGGACCTCCGGTCAGAAAACCAAAATTAT<br>AAGCAACAGAGGTGAAAACAGCTGCAAGGCCACAGGCCAGGTCTGCCAT<br>GCCTTGTGCTCCCCCGAGGGCTGCTGGGGCCCGGAGCCCAGGGACTGCGT<br>CTCTTGCCGGAATGTCAGCCGAGGCAGGGAATGCGTGGACAAGTGCAACC<br>TTCTGGAGGGTGAGCCAAGGGAGTTTGTGGAGAACTCTGAGTGCATACAG<br>TGCCACCCAGAGTGCCTGCCTCAGGCCATGAACATCACCTGCACAGGACG<br>GGGACCAGACAACTGTATCCAGTGTGCCCACTACATTGACGGCCCCCACTG<br>CGTCAAGACCTGCCCGGCAGGAGTCATGGGAGAAAACAACACCCTGGTCT<br>GGAAGTACGCAGACGCCGGCCATGTGTGCCACCTGTGCCATCCAAACTGC<br>ACCTACGGATGCACTGGGCCAGGTCTTGAAGGCTGTCCAACGAATGGGCC<br>TAAGATCCCGTCCATCGCCACTGGGATGGTGGGGGCCCTCCTCTTGCTGCT<br>GGTGGTGGCCCTGGGGATCGGCCTCTTCATGTGA |

Methods of Therapy

Some embodiments of the methods and compositions provided herein include methods of treating or ameliorating or inhibiting a cancer in a subject. Some such embodiments include administering an effective amount to the subject a composition comprising a lipid conjugated to a target moiety, wherein the target moiety comprises a masking moiety; and administering a cell, such as a population of the cells, to the subject, wherein the cell comprises a chimeric antigen receptor (CAR) or T cell receptor (TCR), which specifically binds to the target moiety in the absence of the masking moiety, wherein the CAR or TCR comprises: an amino acid sequence having at least 95% identity with a sequence selected from SEQ ID NO:01-06; and/or a spacer domain comprising, consisting essentially of, or consisting of: a IgG4 hinge connected to a CH2 domain to a CH3 domain, such as a long spacer having an amino acid sequence with at least 95% identity with SEQ ID NO:07, or having an amino acid sequence of SEQ ID NO:07; a IgG4 hinge connected to a CH3 domain, such as a medium spacer having an amino acid sequence with at least 95% identity with SEQ ID NO:08, or having an amino acid sequence of SEQ ID NO:08; or a IgG4 hinge, such as short spacer having an amino acid sequence with at least 95% identity with SEQ ID NO:09, or having an amino acid sequence of SEQ ID NO:09.

In some embodiments, the CAR or TCR comprises an amino acid sequence selected from SEQ ID NO: 1-6. In some embodiments, the spacer comprises a length of 229 amino acids. In some embodiments, the CAR or TCR comprises an scFv domain having the amino acid sequence of SEQ ID NO:1 (FITC-E2 Mut2); and a spacer domain having the amino acid sequence of SEQ ID NO:07 (an exemplary long spacer). In some embodiments, the CAR or TCR comprises an scFv domain having the amino acid sequence of SEQ ID NO:2 (4M5.3); and a spacer domain having the amino acid sequence of SEQ ID NO:07 (an exemplary long spacer). In some embodiments, the CAR or TCR comprises: an scFv domain having the amino acid sequence of SEQ ID NO:5 (FITC-E2); and a spacer domain having the amino acid sequence of SEQ ID NO:07 (an exemplary long spacer).

Some embodiments of the methods and compositions provided herein include methods method of treating, ameliorating, or inhibiting a cancer in a subject comprising (a) introducing, providing, or administering to a subject a composition that comprises a lipid, which comprises a target moiety that is bound to a masking moiety; (b) introducing, providing, or administering to said subject a cell comprising a chimeric antigen receptor (CAR) or T cell receptor (TCR), which is specific for the target moiety once the masking moiety is removed from the target moiety, wherein the CAR or TCR comprises a spacer domain having a spacer length of 1-22 amino acids, 23-50 amino acids, 51-100 amino acids, 100 to 150 amino acids or 151-250 amino acids, wherein: the CAR or TCR comprises a sequence selected from SEQ ID NO:01-06; and/or the spacer domain comprises, consists essentially of, or consists of: an IgG4 hinge connected to a CH2 domain to a CH3 domain, such as a long spacer having an amino acid sequence with at least 95% identity with SEQ ID NO:07, or having an amino acid sequence of SEQ ID NO:07; a IgG4 hinge connected to a CH3 domain, such as a medium spacer having an amino acid sequence with at least 95% identity with SEQ ID NO:08, or having an amino acid sequence of SEQ ID NO:08; or a IgG4 hinge, such as short spacer having an amino acid sequence with at least 95% identity with SEQ ID NO: 9, or having an amino acid sequence of SEQ ID NO:09; (c) removing the masking moiety from the target moiety thereby allowing the target moiety to bind to the CAR present on the cell; and (d) optionally, measuring or evaluating the binding of the cell comprising the CAR to the lipid, after steps a-c; and/or (e) optionally, measuring or evaluating the treatment, amelioration, or inhibition of said cancer after steps a-d; and/or (f) optionally, identifying a subject in need of a therapy for cancer prior to steps a-c.

In some embodiments, the cell is provided to the subject at the same time or 1, 2, 3, 4, 5, 6, 7, 8, 9, 10, 11, 12, 15, 20, 24, 36 or 48 hours before or after administration of the composition, or any time within a range defined by any two aforementioned values. In some embodiments, the cell is provided to the subject 1, 2, 3, 4, 5, 6, 7, 8, 9, 10, 11, 12, 15, 20, 24, 36 or 48 hours before administration of the composition, or any time within a range defined by any two aforementioned values. In some embodiments, the cell is provided to the subject within seconds or minutes, such as less than an hour, of providing the composition to the subject.

In some embodiments, a boost of the cell and/or the composition is provided to the subject.

In some embodiments, an additional cancer therapy is provided to said subject, such as a small molecule, e.g., a chemical compound, an antibody therapy, e.g., a humanized monoclonal antibody with or without conjugation to a radionuclide, toxin, or drug, surgery, and/or radiation.

In some embodiments, the cancer is a solid tumor. In some embodiments the cancer is a colon cancer, breast cancer, ovarian cancer, lung cancer, pancreatic cancer, prostate cancer, melanoma, renal cancer, pancreatic cancer, brain cancer, glioblastoma, neuroblastoma, medulloblastoma, sarcoma, bone cancer, bladder cancer, head and neck cancer, or liver cancer. In some embodiments, the cancer is a non-solid tumor, such as a leukemia or multiple myeloma. Examples of solid tumors include sarcomas, carcinomas, and lymphomas. More examples of cancers, such as solid and non-solid tumors are listed in Amin, M. B., et al., (Eds.). AJCC Cancer Staging Manual (8th edition). Springer International Publishing: American Joint Commission on Cancer; 2017 which is incorporated herein by reference in its entirety.

In some embodiments, binding of the target moiety to the CAR present on the cell induces production of at least one cytokine. In some embodiments, wherein the at least one cytokine comprises IL-2, TNF-α and/or INF-α.

In some embodiments, the lipid comprises a polar head group and a hydrophobic group. In some embodiments, the polar head comprises a choline, a phosphatidylcholine, sphingomyelin, phosphoethanolamine group, an oligosaccharide residue, a sugar residue, phosphatidyl serine or phosphatidyl inositol. In some, the polar-head group comprises phosphocholine, a piperidine moiety or a trimethylarseno-ethyl-phosphate moiety. In some embodiments, the hydrophobic group is fatty acid, such as an aliphatic chain. In some embodiments, the fatty acid is saturated or unsaturated. In some embodiments, the hydrophobic group comprises an alkyl, alkenyl or alkynyl group. In some embodiments, the hydrophobic group comprises a terpenoid lipid, such as a steroid or cholesterol. In some embodiments, the hydrophobic group comprises an ether linkage, wherein the ether linkage is between the polar head group and the aliphatic chain. In some embodiments, the sugar residue is a glycerol or a sugar alcohol. In some embodiments, the hydrophobic group comprises a carbon alkyl chain, wherein the carbon alkyl chain comprises 10, 11, 12, 13, 14, 15, 16, 17, 18, 19 or 20 carbons or any number that is within a range defined by any two aforementioned values. In some embodiments, the carbon alkyl chain comprises 18 carbons. In some embodiments, the lipid is a phospholipid ether.

In some embodiments, the target moiety is biotin, digoxigenin, dinitrophenol, or fluorescein, or a derivative thereof. In some embodiments, the target moiety is fluorescein, or a derivative thereof.

In some embodiments, the spacer comprises a polyethylene glycol (PEG) spacer, a Hapten (2x) spacer, or an alkane chain. In some embodiments, the PEG spacer comprises 1, 2, 3, 4, 5, 6, 7, 8, 9, 10, 11, 12, 13, 14, 15 or 16 PEG molecules, or any amount of PEG molecules that is within a range defined by any two aforementioned values.

In some embodiments, the cell is a precursor T cell. In some embodiments, the precursor T cell is a hematopoietic stem cell. In some embodiments, naïve CD8+ T cells, central memory CD8+ T cells, effector memory CD8+ T cells and bulk CD8+ T cells. In some embodiments, the cell is a CD4+T helper lymphocyte cell that is selected from the group consisting of naïve CD4+ T cells, central memory CD4+ T cells, effector memory CD4+ T cells, and bulk CD4+ T cells.

Kits

Some embodiments of the methods and compositions provided herein include kits. In some embodiments, a kit can include a pharmaceutical grade lipid conjugated with a targeting moiety.

In some embodiments, the lipid comprises a polar head group and a hydrophobic group. In some embodiments, the polar head comprises a choline, a phosphatidylcholine, sphingomyelin, phosphoethanolamine group, an oligosaccharide residue, a sugar residue, phosphatidyl serine or phosphatidyl inositol. In some embodiments, the polar-head group comprises phosphocholine, a piperidine moiety or a trimethylarseno-ethyl-phosphate moiety. In some embodiments, the hydrophobic group is fatty acid, such as an aliphatic chain. In some embodiments, the fatty acid is saturated or unsaturated. In some embodiments, the hydrophobic group comprises an alkyl, alkenyl or alkynyl group. In some embodiments, the hydrophobic group comprises a terpenoid lipid, such as a steroid or cholesterol. In some embodiments, the hydrophobic group comprises an ether linkage, wherein the ether linkage is between the polar head group and the aliphatic chain. In some embodiments, the sugar residue is a glycerol or a sugar alcohol. In some embodiments, the hydrophobic group comprises a carbon alkyl chain, wherein the carbon alkyl chain comprises 10, 11, 12, 13, 14, 15, 16, 17, 18, 19 or 20 carbons or any number that is within a range defined by any two aforementioned values. In some embodiments, the carbon alkyl chain comprises 18 carbons. In some embodiments, the lipid is a phospholipid ether.

In some embodiments, the target moiety is biotin, digoxigenin, dinitrophenol, or fluorescein, or a derivative thereof. In some embodiments, the target moiety is fluorescein, or a derivative thereof.

In some embodiments, the spacer comprises a polyethylene glycol (PEG) spacer, a Hapten (2x) spacer, or an alkane chain. In some embodiments, the PEG spacer comprises 1, 2, 3, 4, 5, 6, 7, 8, 9, 10, 11, 12, 13, 14, 15 or 16 PEG molecules, or any amount of PEG molecules that is within a range defined by any two aforementioned values.

EXAMPLES

Example 1—Preparation of CAR T Cells

T cells were isolated from leukocyte reduction "cones" that are normally disposed of after plateletpheresis. Specifically, Ficoll density centrifugation was used to generate the T cell-containing peripheral blood mononuclear cell (PBMC) fraction and CD8+ and CD4+ T cells were sequentially purified using the appropriate magnetic enrichment kits. T cells were either immediately placed into CAR production the same day as isolation. T cells, ranging from 0.5-5 million cells, were stimulated with anti-human CD3/CD28 activator beads at a 1:1 ratio on Day 0. In some alternatives, the concentrations of the cells can range between 0.5, 1, 2, 3, 4 or 5 million cells that are produced for use with the anti-human CD3/CD28 activator beads.

On Days 1-3 of stimulation, T cells were transduced with CAR-containing lentivirus at a multiplicity of infection (MOI) ranging from 1 to 6 in the presence of protamine sulfate via spinoculation. Half or full-media exchanges were conducted every 2-3 days to maintain the cell cultures at appropriate cell densities and expanded to larger culture vessels as needed. In general, cells were moved to larger culture vessels when cell concentrations reach 1.5-2 million cells/mL or when cultures appear visibly dense and media is yellow. Starting at Day 0 and for every cell feeding, CD4+ T cells were reconstituted with fresh rhIL-7 and rhIL-15 at a final concentration of 50 ng/mL and 0.5 ng/mL, respectively, and CD8+ T cells were reconstituted with fresh rhIL-2 and rhIL-15 at a final concentration of 50 U/mL and 0.5 ng/mL, respectively. Activator beads were magnetically removed on Days 9-11 of stimulation.

For CAR T cells that did not contain DHFRdm for methotrexate-mediated selection of CAR expression (such as those used in examples depicted in FIG. 8B, FIG. 15A, FIG. 15C, FIG. 15D, FIG. 15D, FIG. 15E, FIG. 18C, FIG. 19b, FIG. 19C, FIG. 21A and FIG. 21B), cells were magnetically sorted based on reporter EGFRt expression using biotinylated antibody and anti-biotin microbeads during Days 10-21 of culture. For the CAR T cells that did contain DHFRdm for methotrexate-mediated enrichment of CAR expression (such as those used in examples depicted in FIG. 9, FIG. 10, FIG. 12, FIG. 13, FIG. 14A, and FIG. 14B), cells were first treated on Days 7-14 of culture with 50 nM methotrexate, then ramped up to 100 nM methotrexate on Days 14-19 of culture, and finally brought back down to 50 nM for Days 19-21 of culture. To prevent cultures from crashing due to poor cell viability from methotrexate selection, cells were separated on Ficol on Day 12 of culture to remove dead cells and improve culture viability.

On either Day 14 or 21 of culture, 0.5-2 million T cells for each CAR were placed into a rapid expansion protocol (REP) with irradiated feeder PBMCs and TM-LCL cells. If fresh, unfrozen PBMCs were used, 25 million PBMCs and 5 million TM-LCL cells were used in each REP culture. If frozen PBMCs were used, these feeder cell numbers were doubled. PBMCs and TM-LCL cells were irradiated at 3500 and 8000 rads, respectively, using a Cesium source irradiator. In addition to the normal cytokines mentioned above, cells were also supplemented with OKT3 antibody at 30 ng/μL for Days 0-5 of REP to provide acute TCR stimulation. Irradiated feeder cells disintegrated by Day 5 of REP, and CAR T cells were maintained similarly to as described herein. For CAR T cells that did contain DHFRdm for methotrexate-mediated enrichment of CAR expression (such as those used in examples depicted in FIG. 9, FIG. 10, FIG. 12, FIG. 13, FIG. 14A, and FIG. 14B), 100 nM methotrexate was not introduced until Day 5 of REP and was maintained until Day 12 of REP to further enrich CAR-positive cells. On Day 14 of REP, all CAR T cells described herein were introduced into functional chromium release cytotoxicity assays (CD8+ T cells only) as well as functional 3-plex cytokine release assays (CD4+ and CD8+ T cells).

Example 2—Cytotoxicity and Chromium Release Assays

Target cells were incubated with $^{51}$Cr overnight. For target cells that receive the CTCT-PLEs, the CTCT-PLE was also present in the media overnight with the $^{51}$Cr. The following day the target cells were washed and seeded in a 96 well plate at a concentration 5000 cell per well. CD8+ antiFL and mock T cell effectors (usually in day 8-16 of a rapid expansion protocol) were washed, seeded with the target cells in triplicate at various E:T ratios (30:1, 10:1, 3:1, 1:1), and allowed to co-incubate for 4 hours at 37° C. Also, to evaluate control $^{51}$Cr release, each target cell line was seeded with media only and for maximum $^{51}$Cr release each target cell line was seeded and lysed with 2% SDS. Control groups were done in sextuplicate. After co-incubation, the supernatant was harvested, dispensed on LUMA plates, and allowed to dry overnight. The next day samples were run on the Top Count instrument. Percent-specific lysis was calculated by the following formula:

$$\frac{(\text{experimental }^{51}Cr\text{ release}) - (\text{control }^{51}Cr\text{ release})}{(\text{maximum }^{51}Cr\text{ release}) - (\text{control }^{51}Cr\text{ release})} \times 100$$

See e.g., Gonzalez, S., Naranjo, A., Serrano, L. M., Chang, W.-C., Wright, C. L., & Jensen, M. C. (2004). Genetic engineering of cytolytic T lymphocytes for adoptive T-cell therapy of neuroblastoma. *The Journal of Gene Medicine*, 6(6), 704-711, hereby expressly incorporated by reference in its entirety.

Example 3—Cytokine Release Assay

For target cells that received the CTCT-PLEs, the CTCT-PLE was incubated overnight in media. The next day all target cells were harvested, washed, and seeded in a 96 well plate at a concentration of 5×10$^4$ cells per well. CD8+ antiFL and mock T cell effectors (usually in day 8-16 of a rapid expansion protocol) were washed and seeded (1×10$^5$ cells/well) with the target cells allowed to co-incubate for 24 hours at 37° C. After 24 hr the supernatant was harvested and IFN-gamma, TNF-alpha, and IL-2 concentration in the supernatant were measured by using a BioPlex® 200 system (Bio-Rad).

Example 4—FACS Analysis for EGFRt and antiFL CAR Expression

Figure 6:
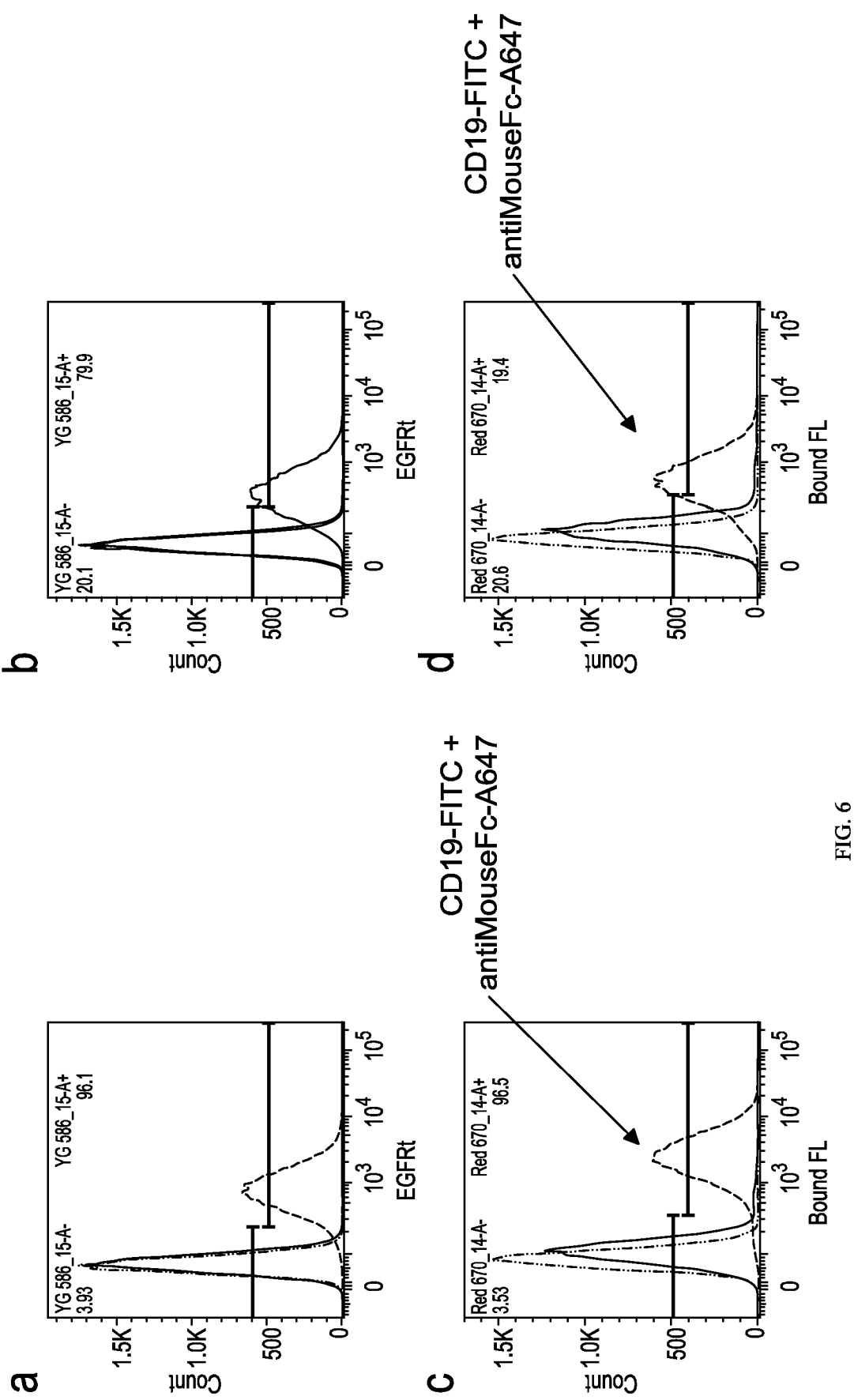
FIG. 6 depicts FACS analysis of CD8+ T cells containing antiFL CARs. Panel (a) and (b) depict T cells staining for the selection marker EGFRt containing either an antiFL(FITC-E2) CAR, which comprises SEQ ID NO: 5 [96% positive], or an antiFL(4M5.3) CAR, which comprises SEQ ID NO: 2 [80% positive], respectively. Panels (c) and (d) depict T cells incubated with a mouse CD19-FITC antibody, then stained with an anti-mouse-Fc-Alexa647 antibody for the bound FITC antibody, for T cells containing either the antiFL (FITC-E2) CAR [97% positive], or the antiFL(4M5.3) CAR [79% positive], respectively.

CD8+ T cells containing antiFL CARs were stained for EGFRt or antiFL binding. FIG. 6 depicts cell positivity of CD8+ antiFL CARs T cell via staining for the selection marker EGFRt. (a) antiFL(FITC-E2) CAR which comprised SEQ ID NO: 5 [96% positive]. (b) antiFL(4M5.3) CAR which comprised SEQ ID NO: 2 [80% positive]. To test the antiFL CARs ability to bind to FL, a mouse CD19-FITC antibody was incubated with the T cells and washed out. Anti-mouse-Fc-Alexa647 antibody was stained for the bound FITC antibody (c) antiFL(FITC-E2) CAR [97% positive] and (d) antiFL(4M5.3) CAR [79% positive]. The two different stainings gave the same positivity confirming the one to one relationship of CAR to surface marker and that the antiFL CAR can bind to FL. The binding domains of the CARs can comprise a sequence as set forth in SEQ ID NO: 1-6, and the spacer domains, which may also be part of the CARs, can comprise a sequence as set forth in SEQ ID NO: 7-9.

Example 5—CAR T Cell Recognition and Activation Through FL-PLE In Vitro

Figure 7A:
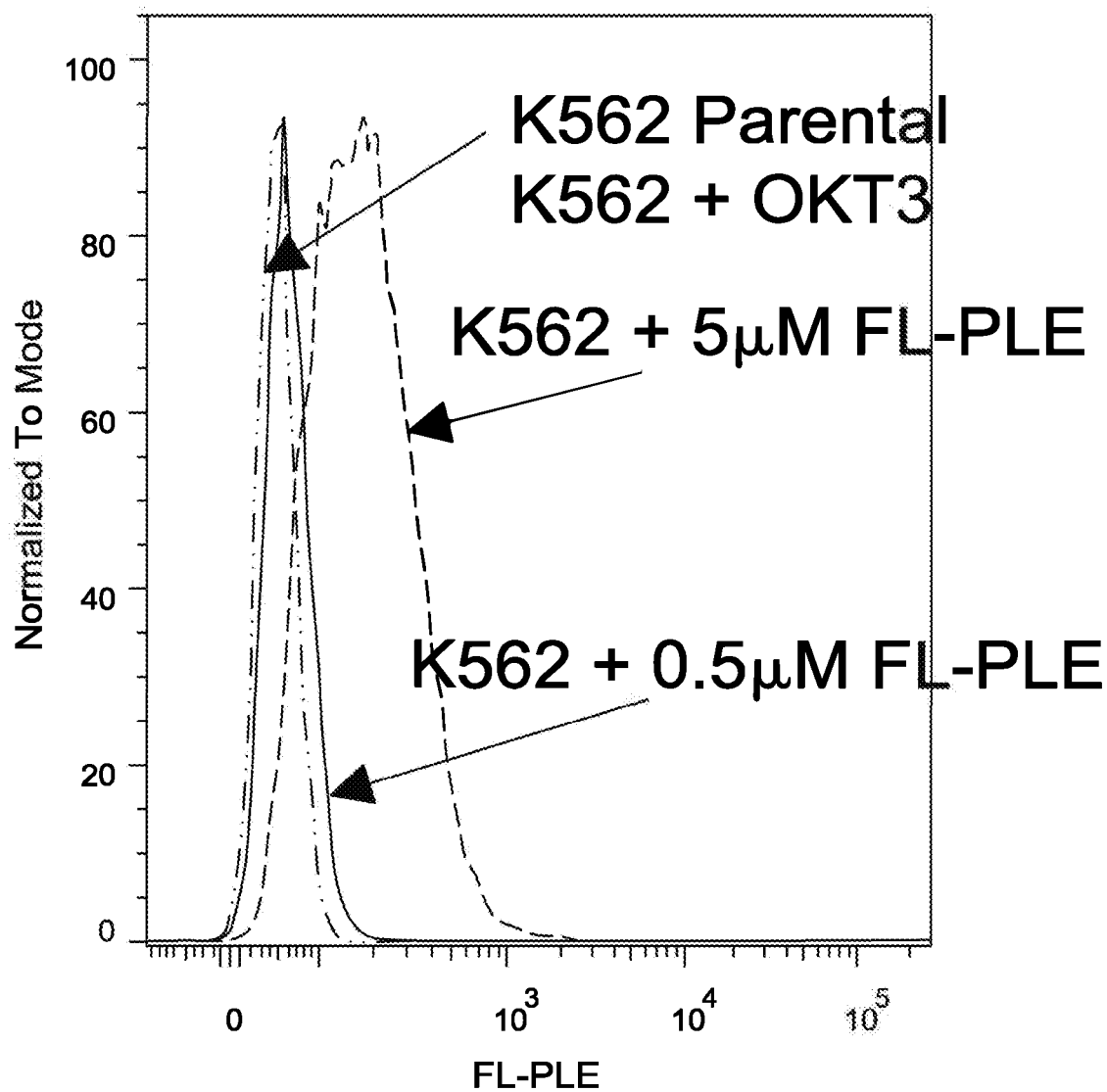
FIG. 7A depicts a FACS analysis of cells treated with FL-PLE.
Figure 7B:
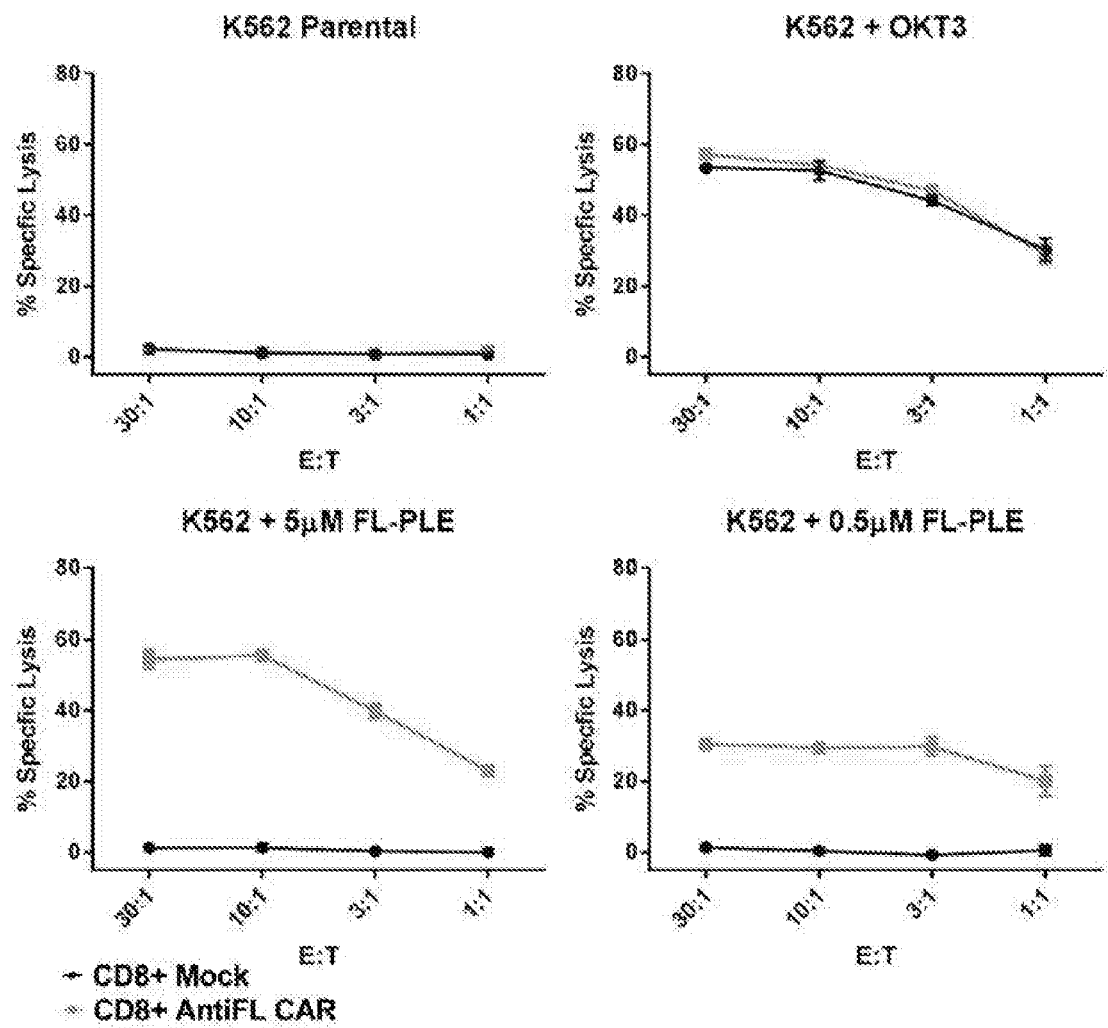
FIG. 7B depicts specific lysis of K562 cells in the presence or absence of FL-PLE, and in the presence or absence of CD8+ T cells containing an antiFL CAR.
Figure 7C:
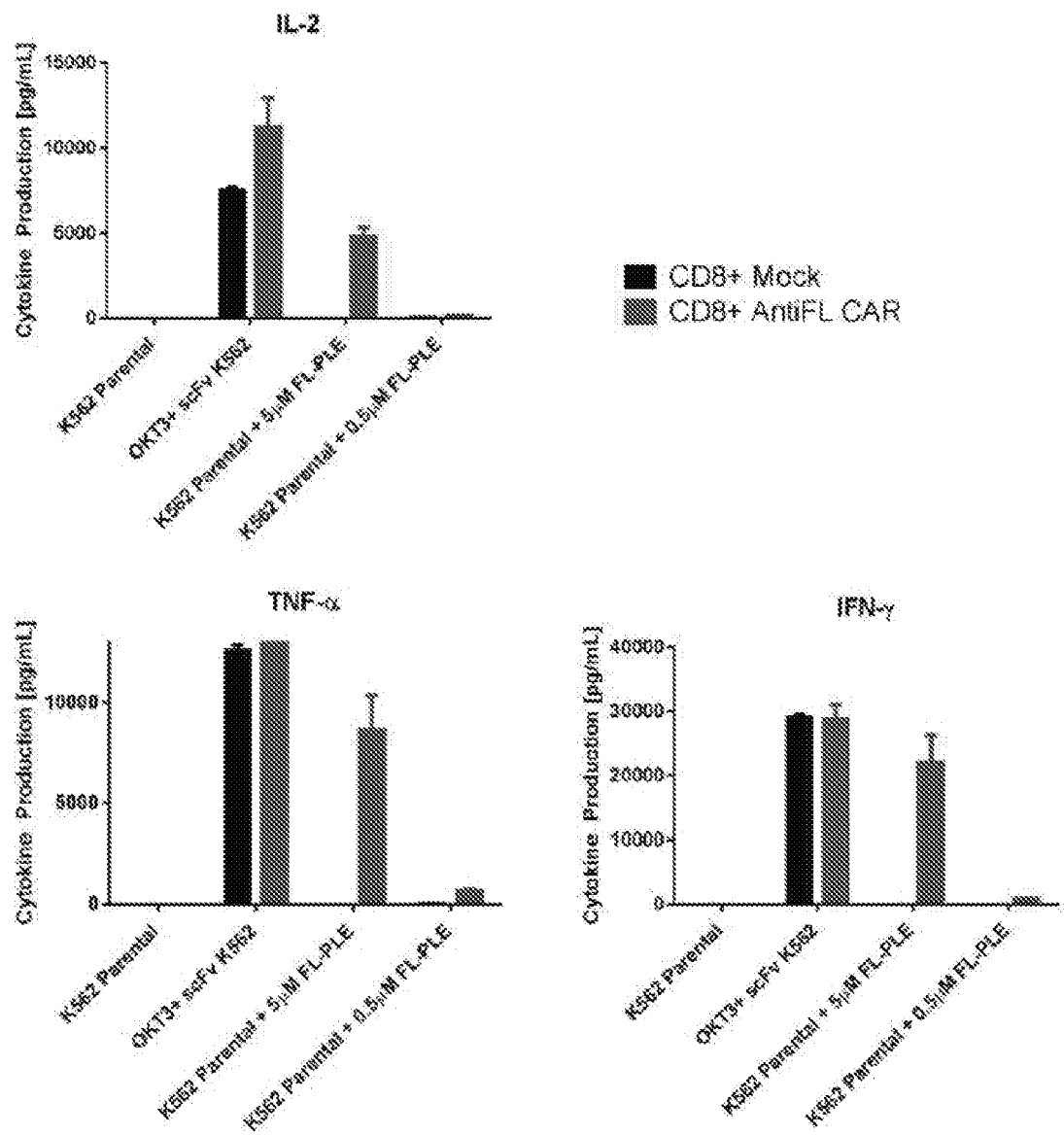
FIG. 7C depicts cytokine production from K562 cells in the presence or absence of FL-PLE, and in the presence or absence of CD8+ T cells containing an antiFL CAR.

T cells containing antiFL CARs were tested for binding to FL-PLE and activation. FIG. 7A, FIG. 7B, and FIG. 7C show CAR T cell recognition and activation through FL-PLE in vitro. K562 (leukemia) cells were incubated with FL-PLE overnight. Cell integration of FL-PLE was analyzed by flow cytometry (FIG. 7A). There was a clear shift from the control K562 parental with the K562 parental incubated with 5 µM FL-PLE, whereas there was a very slight shift with K562 parental incubated with 0.5 µM FL-PLE. This slight shift corresponded to a difference in the amount of FL exposed on the surface of the cell for CAR T cell recognition. Also, the K562 OKT3+ cells (a cell line created to test the endogenous activation of T cells through the TCR) matched the K562 parental exactly. These cells were used in a chromium release assay (FIG. 7B) and a cytokine release assay (FIG. 7C) to test the activation of CD8+ antiFL(FITC-E2) CAR T cells compared with a CD8+ mock T cells from FIG. 6. From these experiments, the antiFL (FITC-E2) CAR T cells recognized the FL moiety of the FL-PLE integrated into the plasma membrane and that the cells were activated. The amount of the activation was associated with the amount FL exposed on the surface of the cell.

Figure 8A:
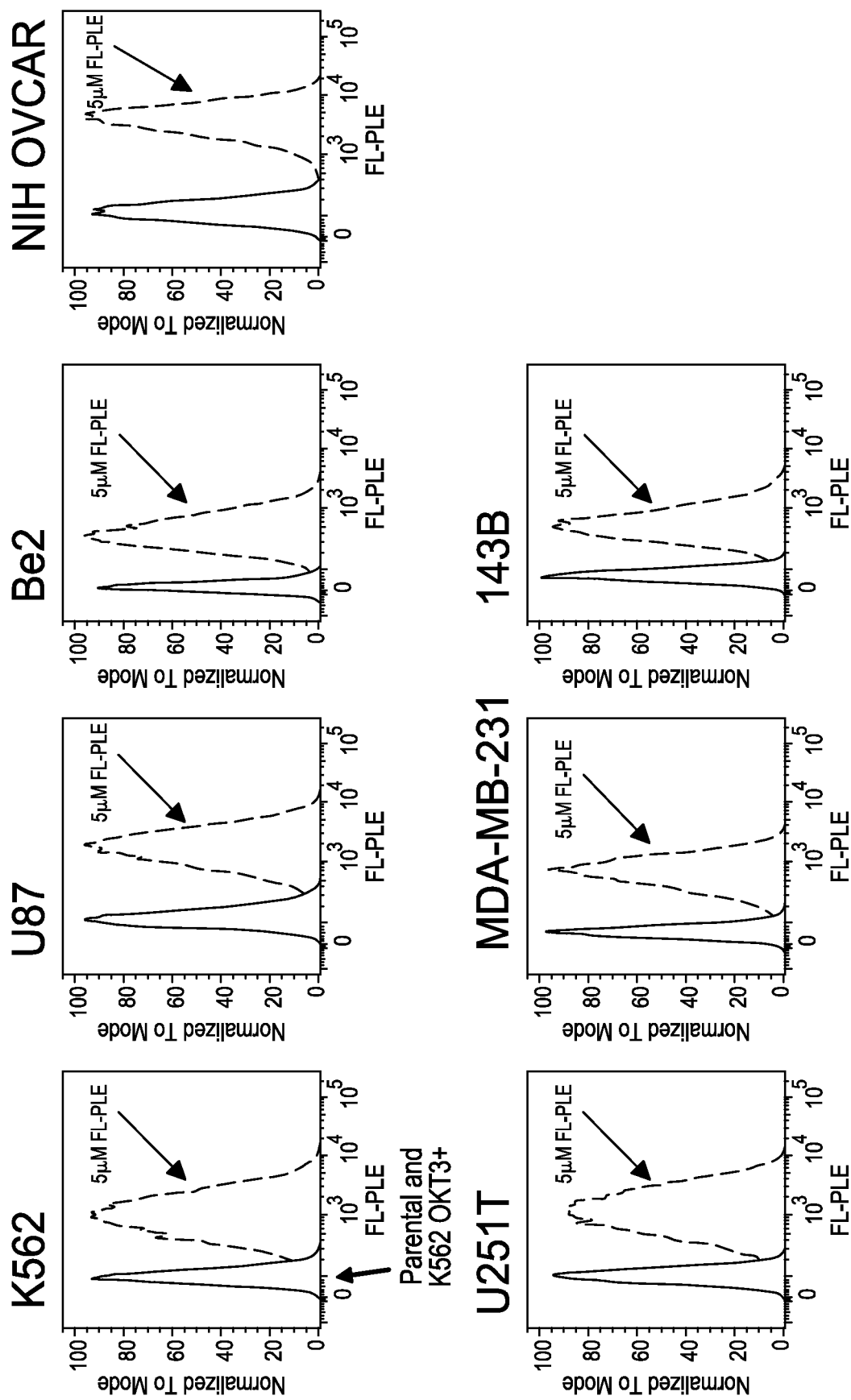
FIG. 8A depicts FACS of various cell lines treated with FL-PLE.
Figure 8B:
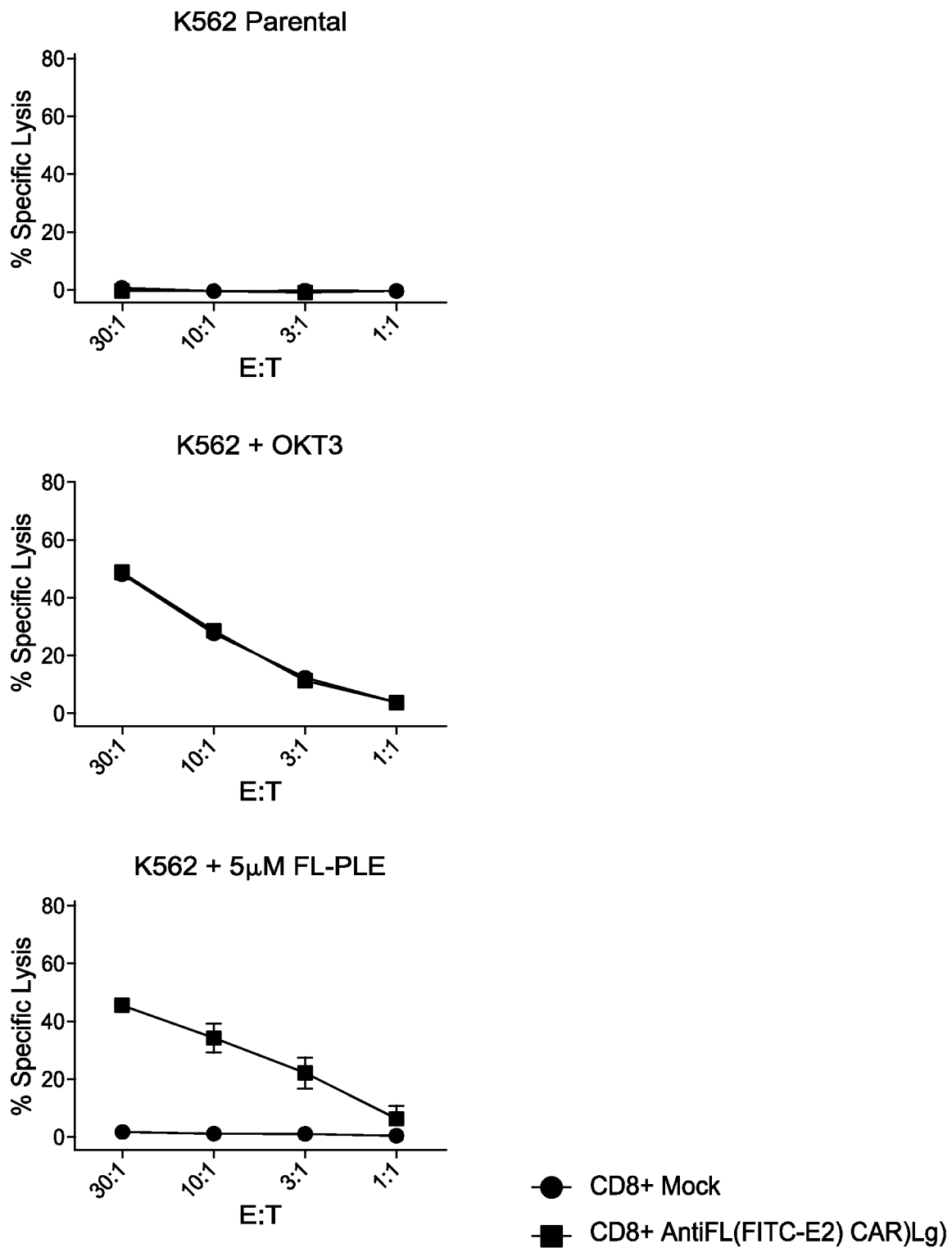
FIG. 8B depicts specific lysis of cells treated with FL-PLE and contacted with CD8+ T cells containing an antiFL (FITC-E2) CAR containing a long spacer.
Figure 8B:
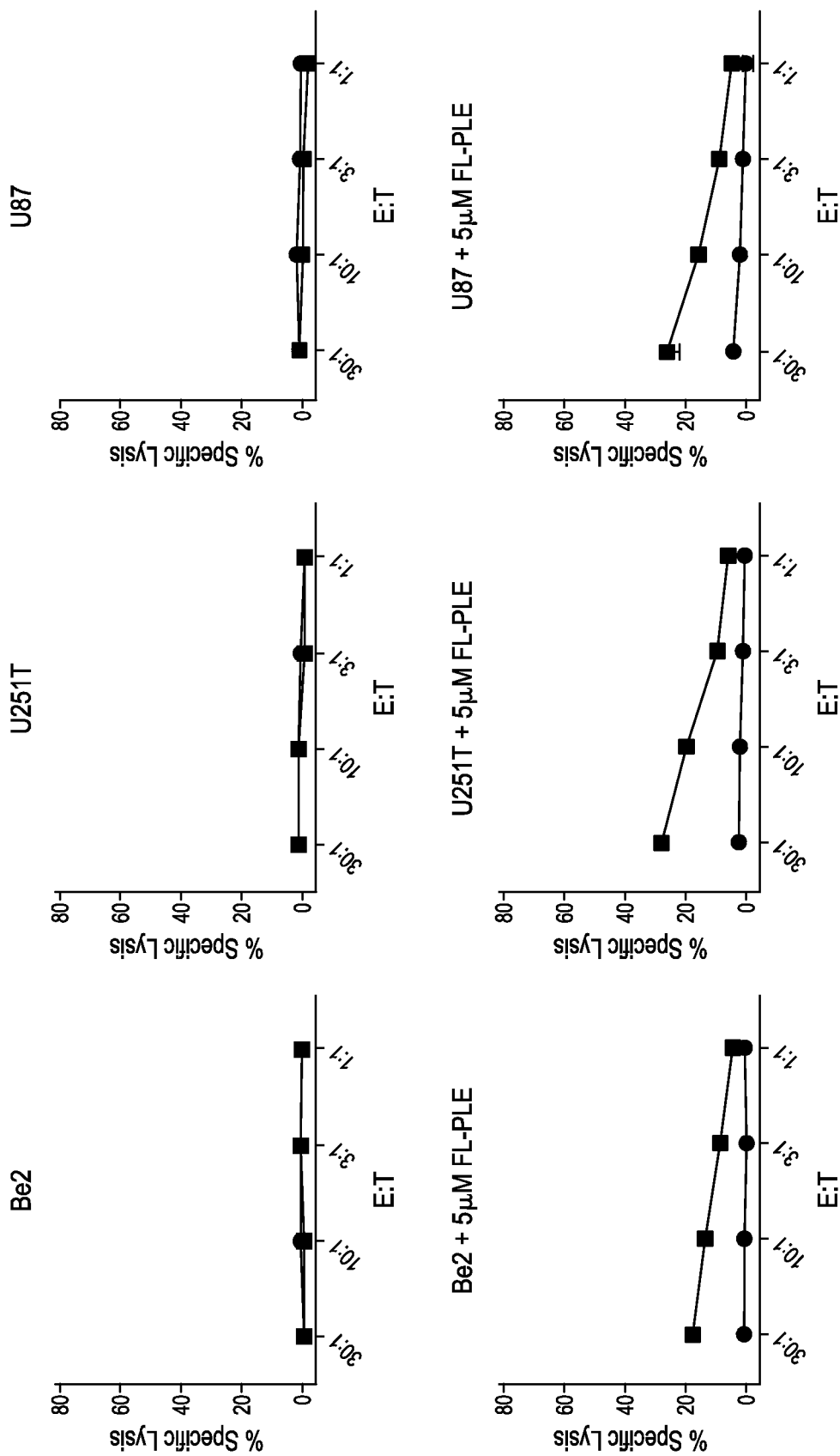
Figure 8B:
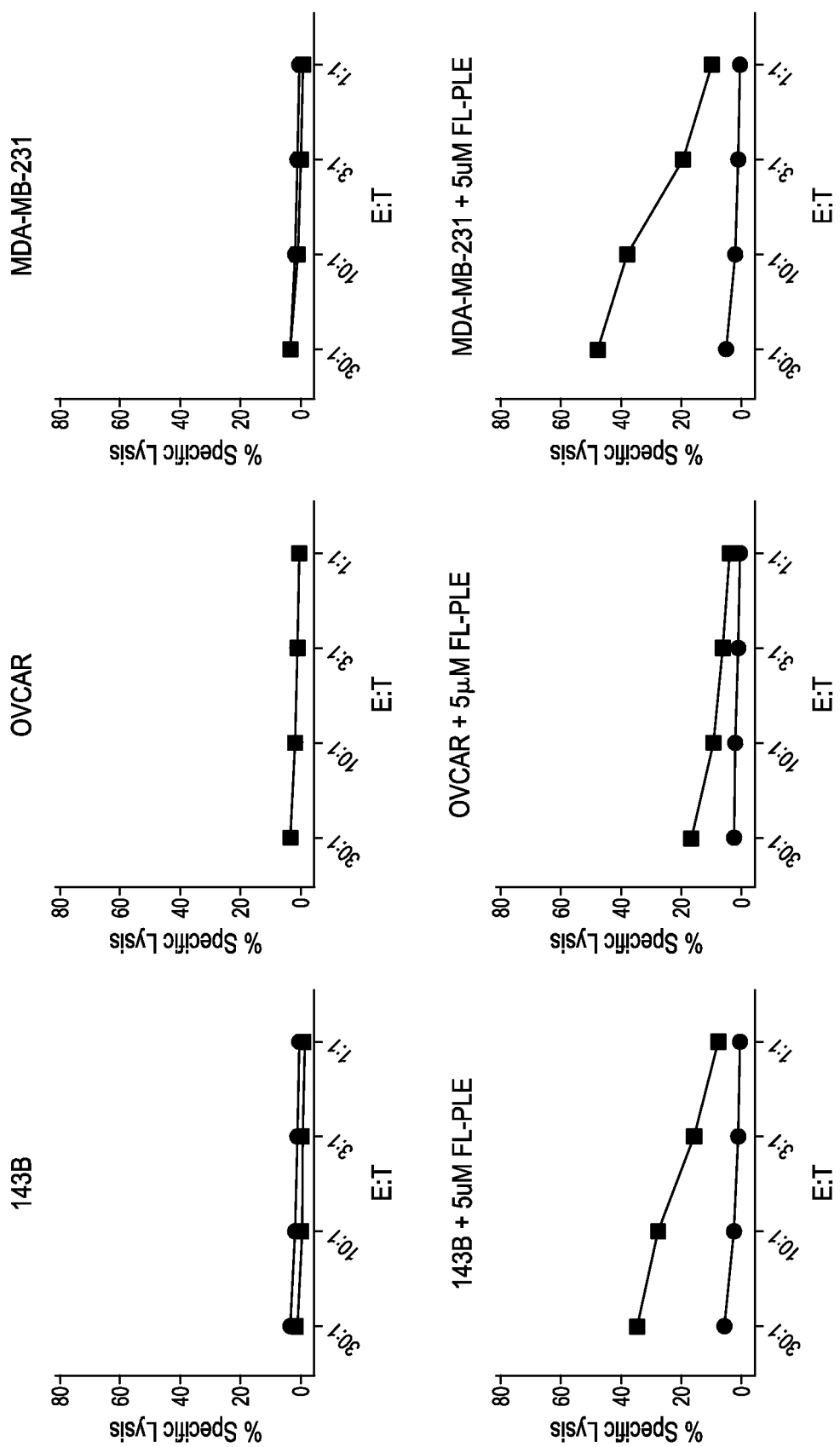

FIG. 8A and FIG. 8B depict the universality of FL-PLE loading in tumor cells and recognition of the fluorescein moiety by antiFL CAR T cells. K562 (leukemia), U87 (glioblastoma), 251T (glioma), Be2 (neuroblastoma), MDA-MB-231 (adenocarcinoma), NIH OVCAR (adenocarcinoma), and 143B (osteosarcoma) cells were incubated with FL-PLE overnight. Cell integration of FL-PLE was analyzed by flow cytometry (FIG. 8A). There was a clear shift from the control parental cell lines with the parental cell lines incubated with 5 FL-PLE corresponding to the amount of FL exposed on the surface of the cell for CAR T cell recognition. Also the K562 OKT3+ cells (a cell line created to test the endogenous activation of T cells through the TCR) matched the K562 parental exactly, as expected. These cells were used in a chromium release assay (FIG. 8B) to test the cytotoxic response of CD8+ antiFL(FITC-E2) CAR T cells compared with a CD8+ mock T cells. These experiments demonstrated that the antiFL(FITC-E2) CAR T cells recognized the FL moiety of the FL-PLE integrated into the plasma membrane of multiple different cancer types and that the CAR T cells are able to lyse the targets.

Example 6—Methotrexate Selection of CAR T Cells

Figure 9:
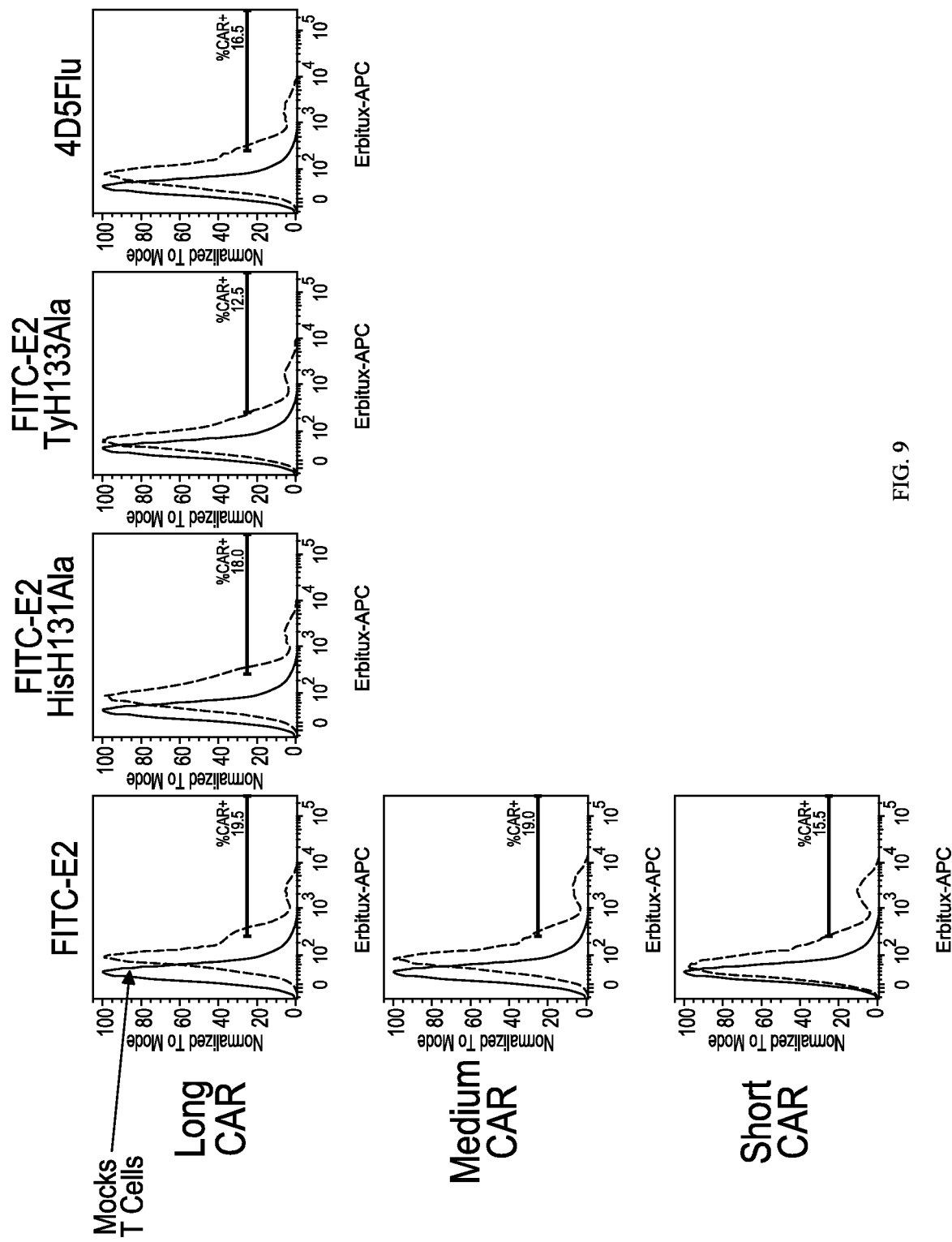
FIG. 9 depicts a FACS analysis of CD8+ T cells contain various antiFL CARs, and staining for a surface marker, EGFRt.

CAR T cells were selected for with methotrexate. FIG. 9 shows CD8+ antiFL CAR T cells selected by methotrexate, a chemotherapeutic in which antiFL CARs include CARs with FITC-E2 scFv domain and either a long, medium or short spacer, and other CARs having an antiFL scFv domain as labeled and a long spacer. CAR positivity of CD8+ antiFL CAR T cells staining for the surface marker EGFRt. These antiFL CARs also harbored a gene for a double mutant dihydrofolate reductase (DHFRdm) that confered methotrexate resistance for methotrexate-mediated enrichment of CAR-positive cells. Every cell line except minimum EGFRt+ cells were diluted with mock T cells to make equivalent stocks to use in functional assays. Target: 18.1% EGFRt+. Actual: about 13-20% EGFRt+.

Figure 10:
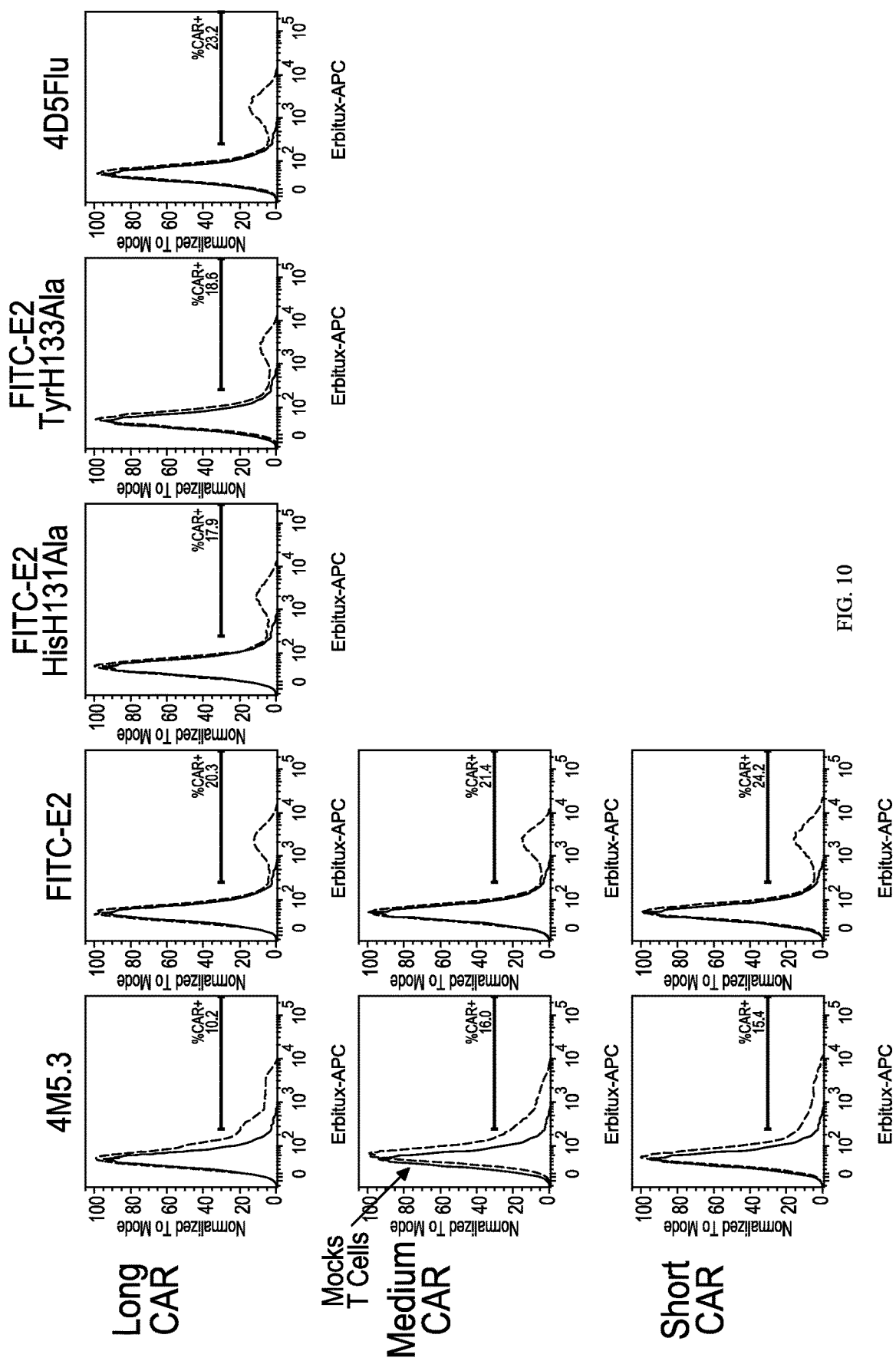
FIG. 10 depicts a FACS analysis of CD4+ T cells contain various antiFL CARs, and staining for a surface marker, EGFRt.

FIG. 10 shows another example in which CD4+ antiFL CAR T cells selected by methotrexate, a chemotherapeutic. CAR positivity of CD4+ antiFL CAR T cells via staining for the surface marker EGFRt. These antiFL CARs also harbor a gene for a double mutant dihydrofolate reductase (DHFRdm) that confers methotrexate resistance and, thus allows for methotrexate-mediated enrichment of CAR-positive cells. Every cell line except minimum EGFRt+ cells were diluted with mock T cells to make equivalent stocks to use in functional assays. Target: 18.1% EGFRt+. Actual: about 15-24% EGFRt+.

Example 7—Labelling Cells with FL-PLE

Figure 11:
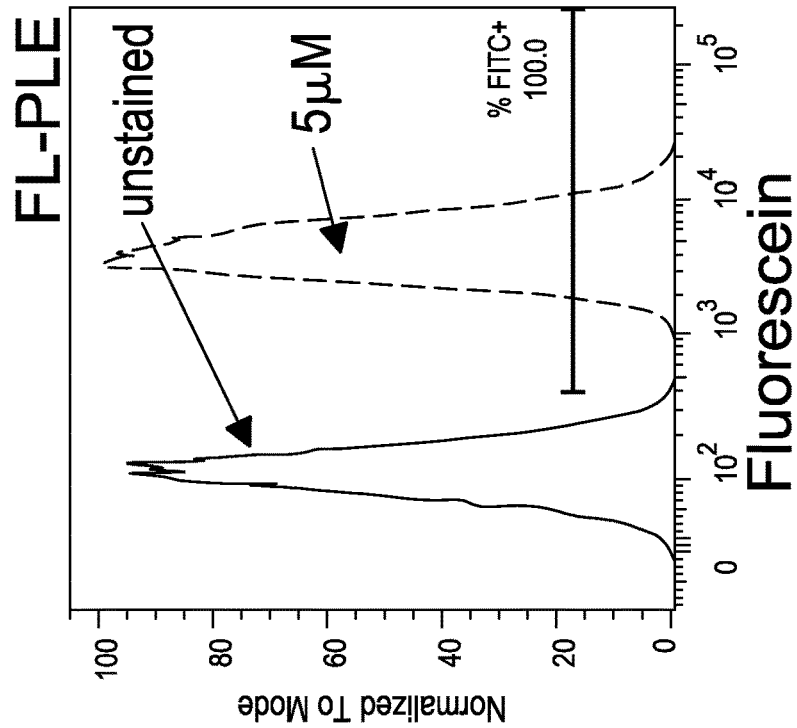
FIG. 11 depicts a FACS analysis of cells labeled with FL-PLE.
Figure 11:
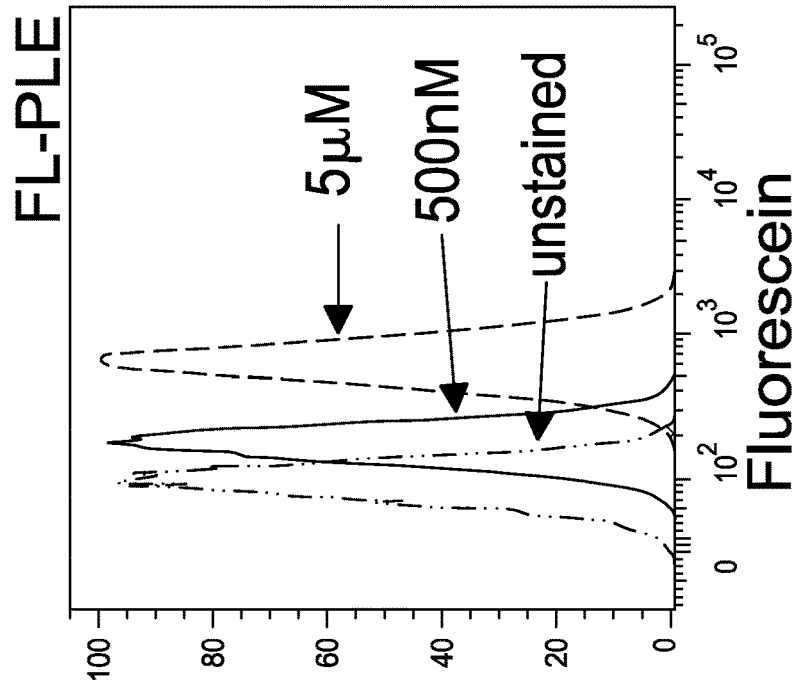

Target cells were labelled with FL-PLE. FIG. 11 shows loading of cells with FL-PLE. Target cells for functional assays were made using K562 cells and MDA-MB-231 cells. Each cell group was labeled with FL-PLE. Cell integration of FL-PLE to the plasma membrane was analyzed by flow cytometry.

Example 8—CAR T Cell Cytotoxicity Assays

Figure 12:
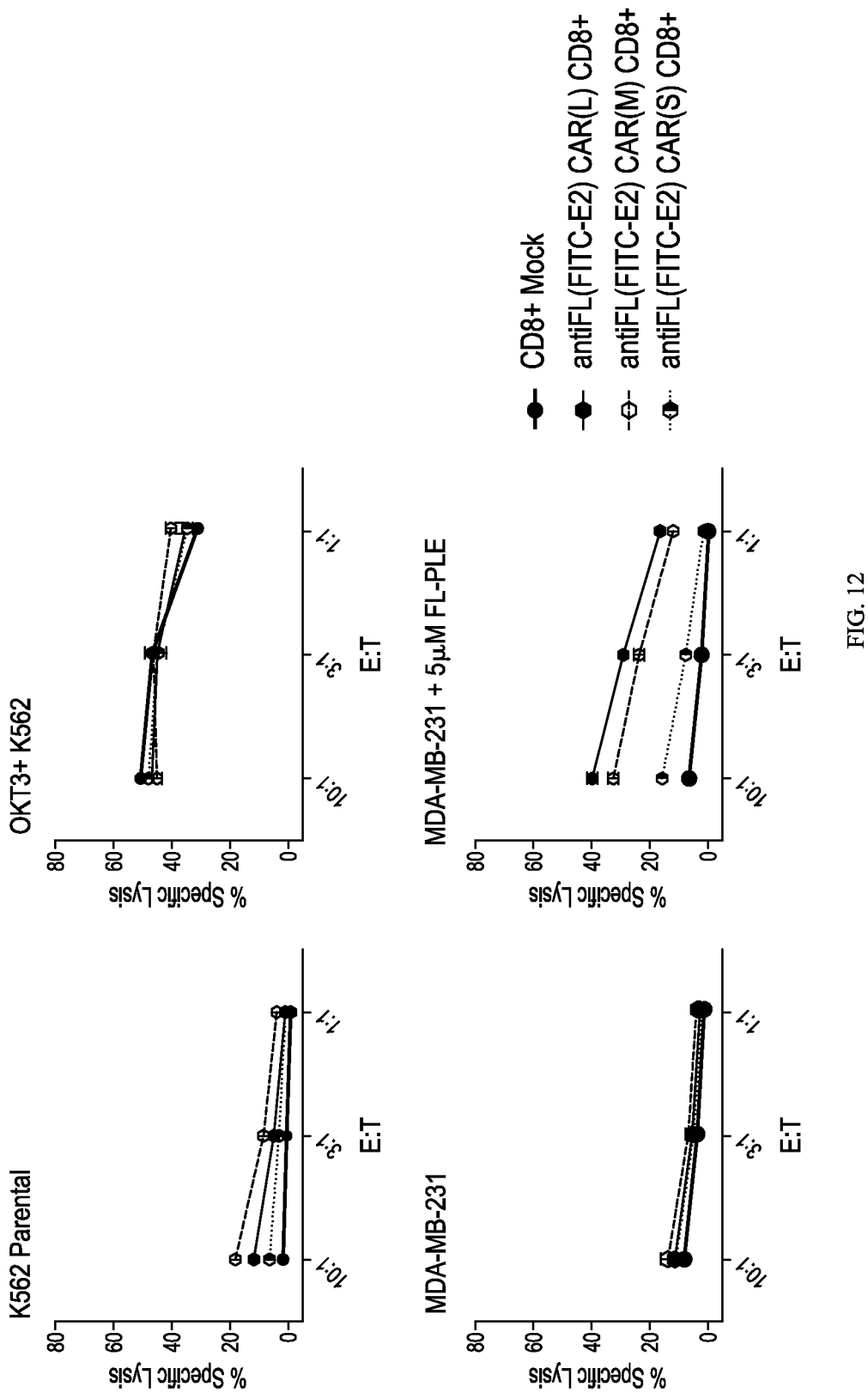
FIG. 12 depicts specific lysis of target cells incubated with FL-PLE and contacted with CD8+ T cells containing antiFL CARs.

Cytotoxicity of CAR T cells was tested. FIG. 12 shows CD8+ antiFL CAR T cell cytotoxicity assays. MDA-MB-231 cells were incubated with FL-PLE. Cell integration of FL-PLE was analyzed by flow cytometry. These cells and the CAR T cells were used in a chromium release assay. The negative controls (K562 Parental and MDA-MB-231) both showed no killing and the positive control (K562 OKT3+ cells) showed cell lysis as expected. For MDA-MB-231 cells labeled with FL-PLE, the long CAR barely outperformed the medium; whereas only slight killing was seen with the short CAR. These results demonstrated the importance of the spacer length for the CAR T cell lysis of target cells and the hapten labeling method for a cell was useful for deciding on a spacer length.

Figure 14A:
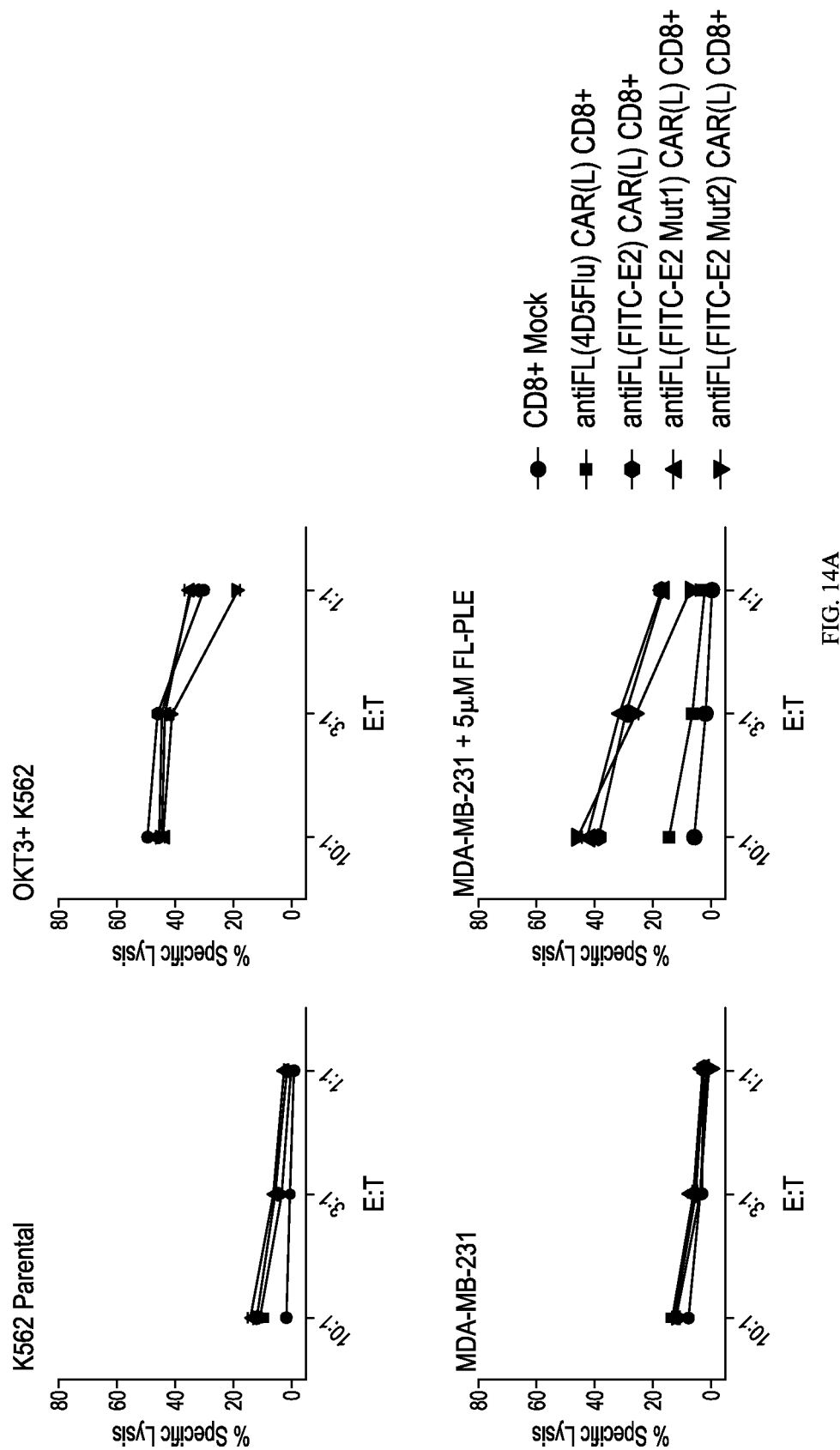
FIG. 14A depicts specific lysis of target cells incubated with FL-PLE and contacted with CD8+ T cells containing antiFL CARs.

FIG. 14A shows CD8+ antiFL CAR T cell assays with different antiFL scFv. MDA-MB-231 cells were incubated with FL-PLE. Cell integration of FL-PLE was analyzed by flow cytometry. These cells and the CAR T cells were used in a chromium release assay. The negative controls (K562 Parental and MDA-MB-231) both showed no killing and the positive control (K562 OKT3+ cells) showed cell lysis as expected (FIG. 14A). This chromium assay tested four different antiFL scFv's in the context of a long CAR. For MDA-MB-231 cells labeled with FL-PLE, three of the antiFL CARs all showed equivalent lysis; whereas antiFL (4D5Flu) which comprised SEQ ID NO: 4 exhibited almost no killing. AntiFL (4D5Flu) in other experiments has shown the ability to lysis cells labeled with FL. Accordingly, antiFL(4D5Flu) was not orientated in the correct relationship to recognize the FL moiety on the FL-PLE when integrated into a cell membrane.

Example 9—CAR T Cell Cytokine Release Assays

Figure 13:
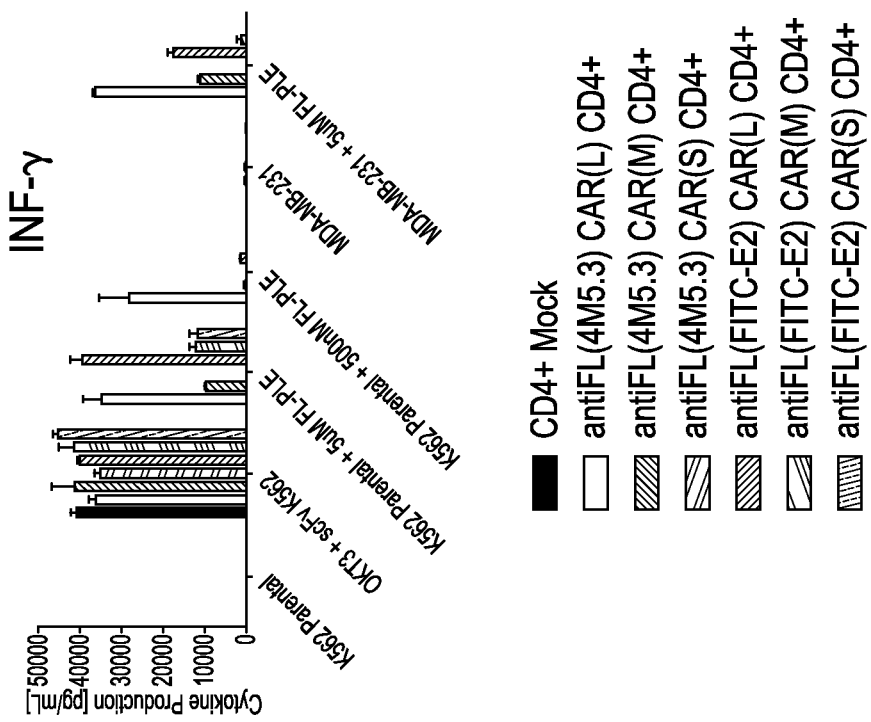
FIG. 13 depicts cytokine production of cells incubated with FL-PLE and contacted with CD4+ T cells containing antiFL CARs.
Figure 13:
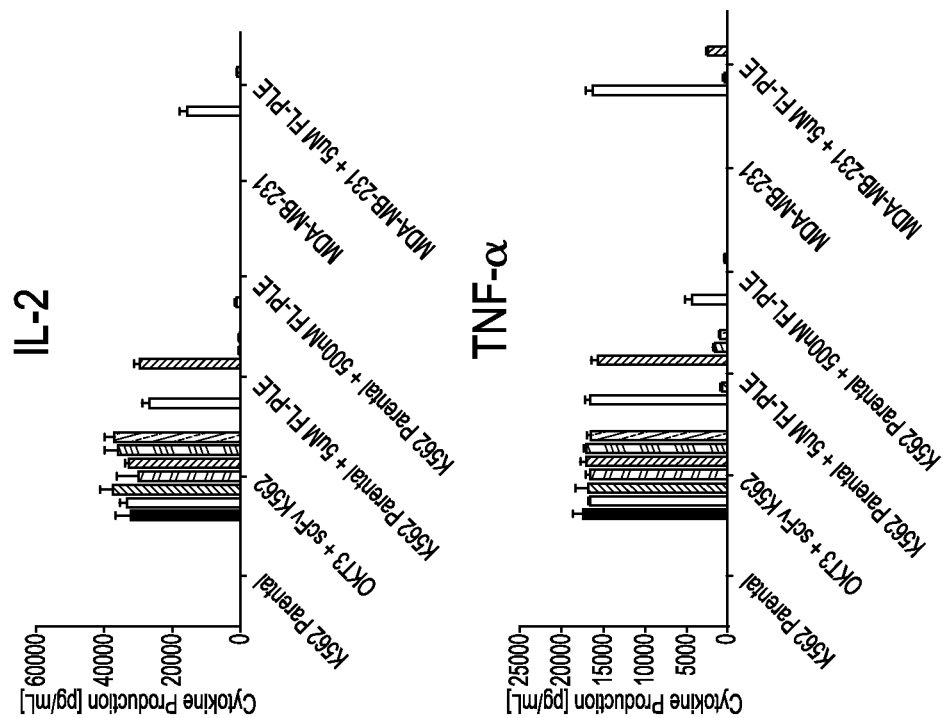

Cytokine release from CAR T cells was assayed. FIG. 13 depicts CD4+ antiFL CAR T cell cytokine release assays. K562 and MDA-MB-231 cells were incubated with FL-PLE. Cell integration of FL-PLE was analyzed by flow cytometry. These cells and the antiFL CAR T cells were used in a cytokine release assay. The negative controls (K562 Parental and MDA-MB-231) both showed no cytokine production and the positive control (K562 OKT3+ cells) showed production of all three cytokines for all cell lines. This assay was designed to study the relationship of the spacer length of CAR and FL-PLE. This data shows that only the long spacer CAR in relationship with FL-PLE was able to produce all three cytokines.

Figure 14B:
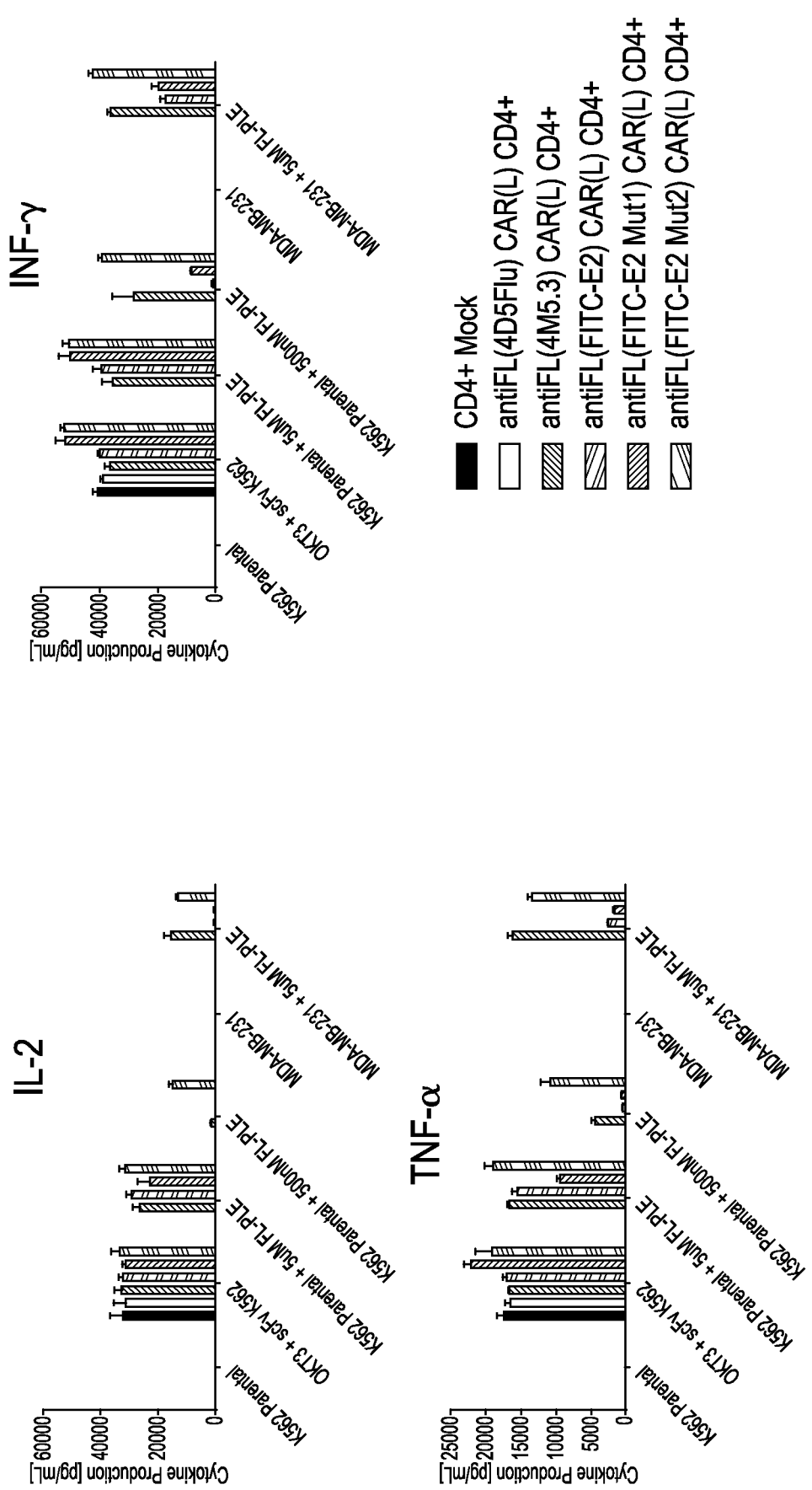
FIG. 14B depicts cytokine production of cells incubated with FL-PLE and contacted with CD4+ T cells containing antiFL CARs.

FIG. 14B depicts CD4+ antiFL CAR T cell cytokine release assays with different antiFL scFv. K562 and MDA-MB-231 cells were incubated with FL-PLE. Cell integration of FL-PLE was analyzed by flow cytometry. These cells and the CAR T cells were used in a cytokine release assay. The negative controls (K562 Parental and MDA-MB-231) both showed no cytokine production and the positive control (K562 OKT3+ cells) showed production of all three cytokines for all cell lines. This cytokine release assay tested five different antiFL scFv's in the context of a long CAR. Of the K562 cells labeled with 5 µM FL-PLE, only four of the antiFL CARs showed activation. As the amount of FL-PLE was reduced to 500 nM in the K562 cells, antiFL(4M5.3) which comprised SEQ ID NO: 2 and antiFL(FITC-E2 Mut2) which comprised SEQ ID NO: 1 produced the most cytokine with only antiFL(FITC-E2 Mut2) was able to produce IL2. Also antiFL(4M5.3) and antiFL(FITC-E2 Mut2) produced the most cytokine with MDA-MB-231 cells labeled with 5 µM FL-PLE. AntiFL(4M5.3) and antiFL(FITC-E2 Mut2) showed the best activation with FL-PLE and had vastly different disassociation constants, 270 fm and 3.1 nM respectively, showing that just lowering a CAR's disassociation constant did not necessarily make for the best CAR. The CAR that did not work in conjunction with FL-PLE was antiFL(4D5Flu), which comprised SEQ ID NO: 4. AntiFL (4D5Flu) exhibited no cytokine production in either cell line labeled with 5 µM FL-PLE. AntiFL(4D5Flu) in other experiments has shown the ability to lysis cells labeled with FL. Accordingly, antiFL(4D5Flu) was not orientated in the correct relationship to recognize the FL moiety on FL-PLE when integrated into a cell membrane.

Figure 15A:
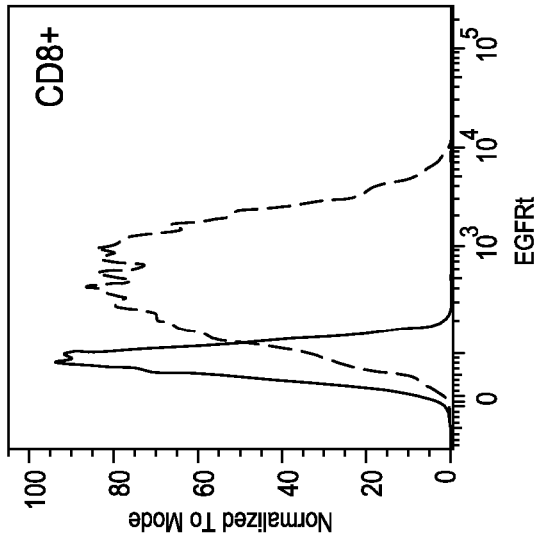
FIG. 15A depicts a FACS analysis of cells containing various antiFL CARs.
Figure 15A:
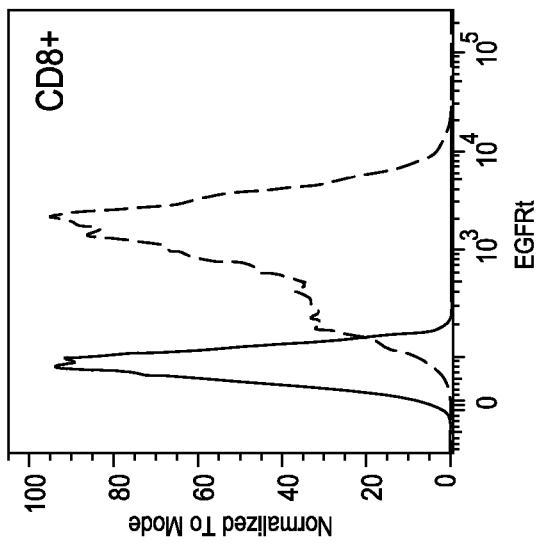
Figure 15A:
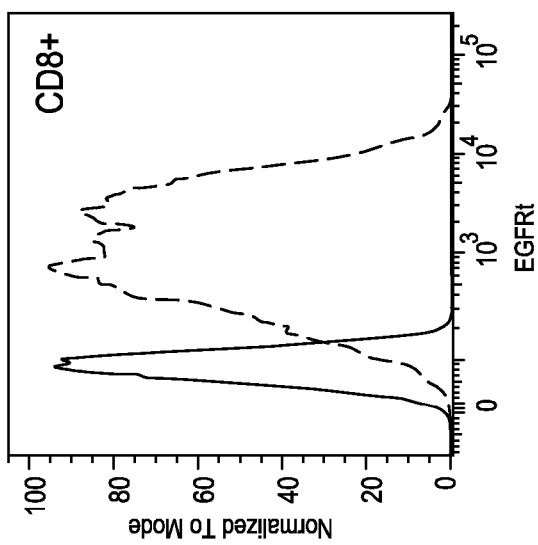
Figure 15A:
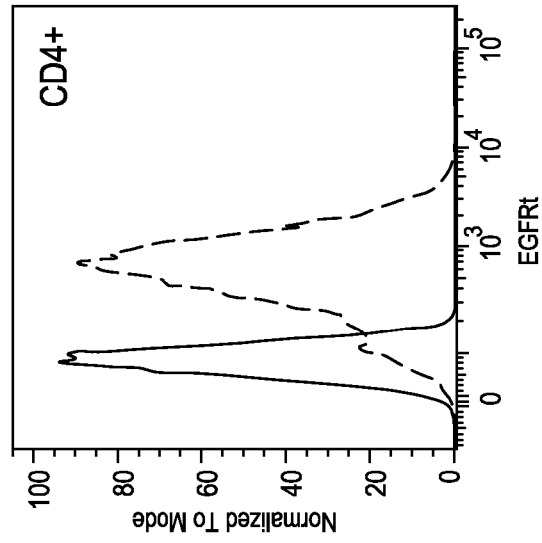
Figure 15A:
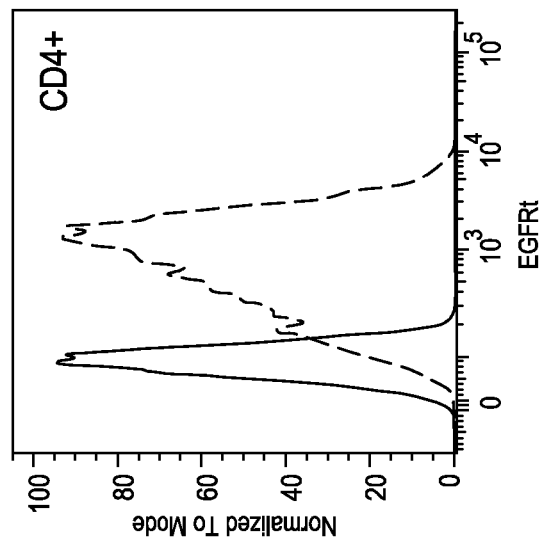
Figure 15A:
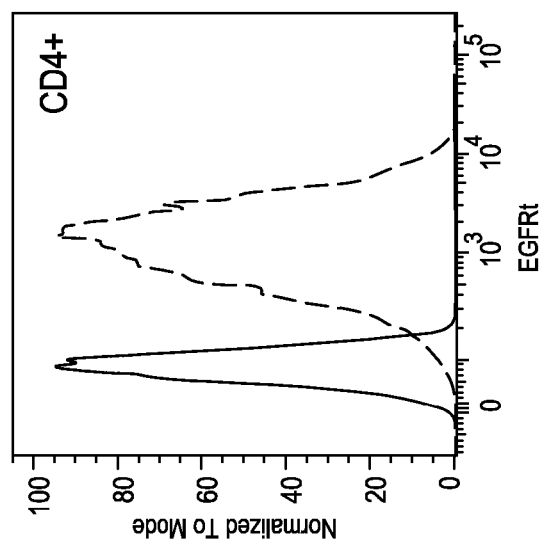
Figure 15B:
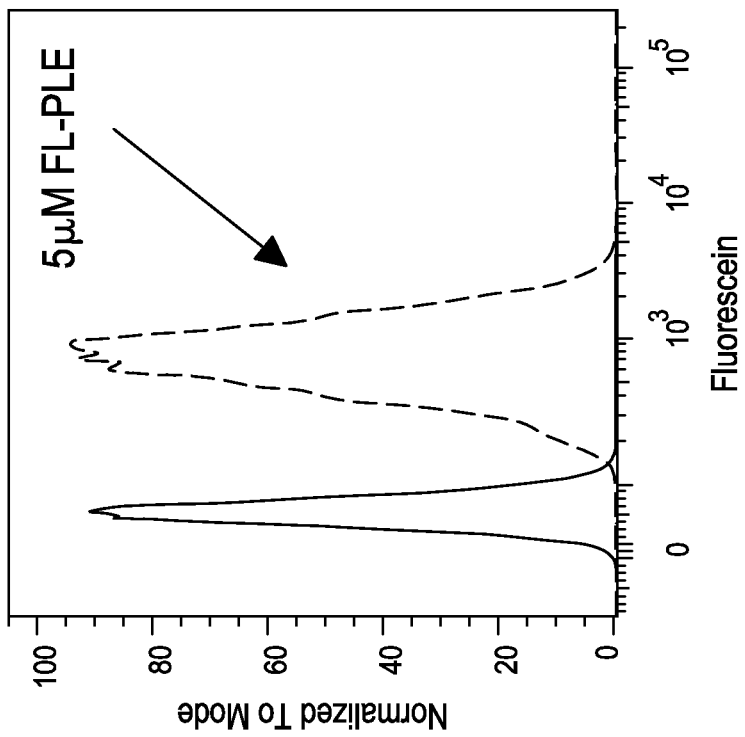
FIG. 15B depicts a FACS analysis of cells treated with FL-PLE.
Figure 15B:
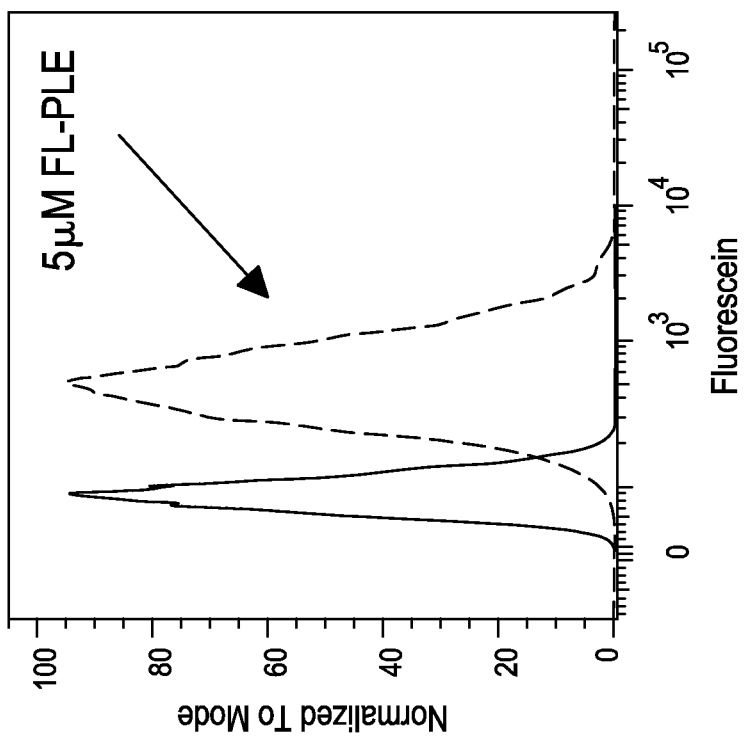
Figure 15C:
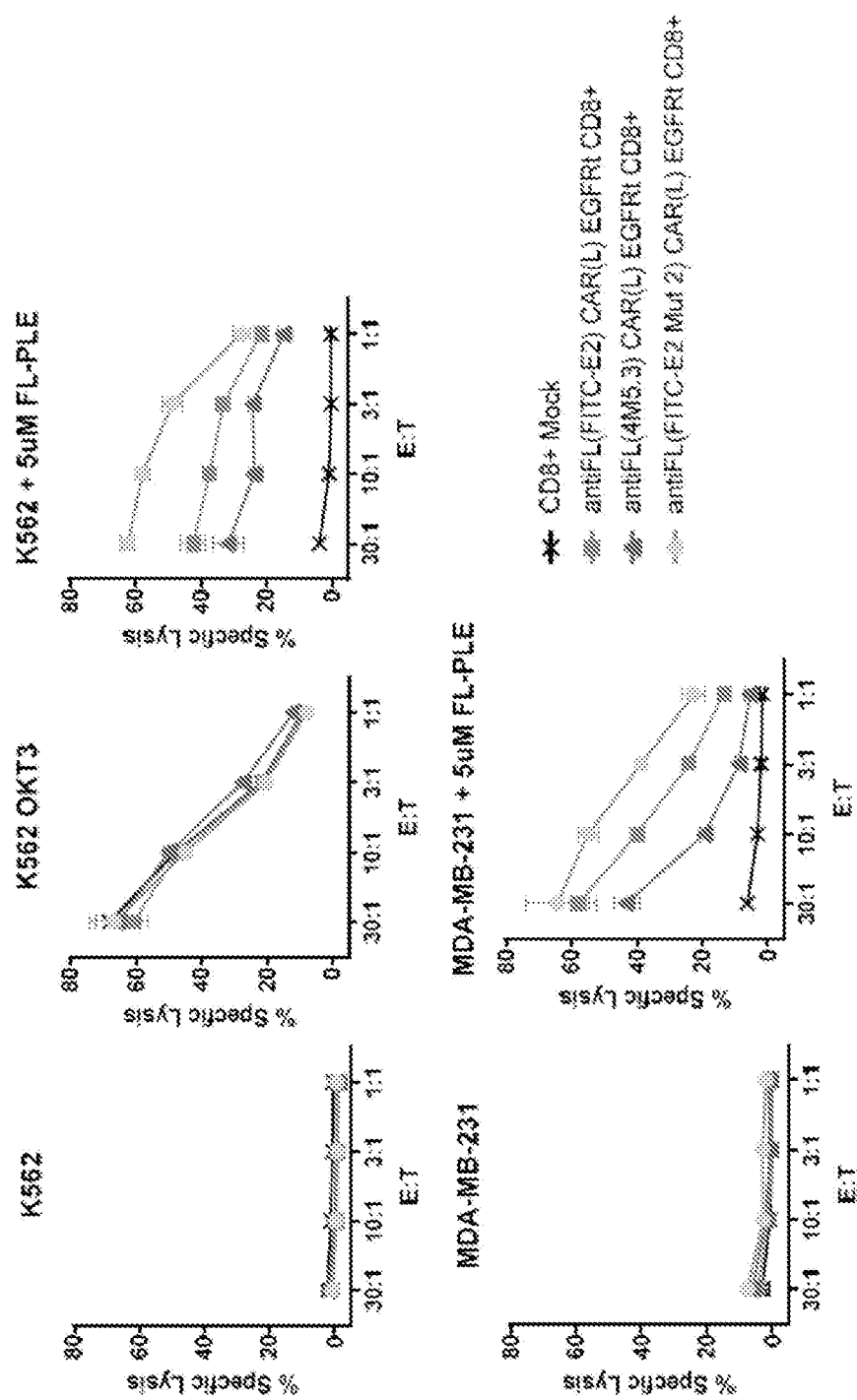
FIG. 15C depicts a series of graphs for specific lysis of various tumor cells in the presence or absence of FL-PLE, and contacted with various antiFL CARs.
Figure 15D:
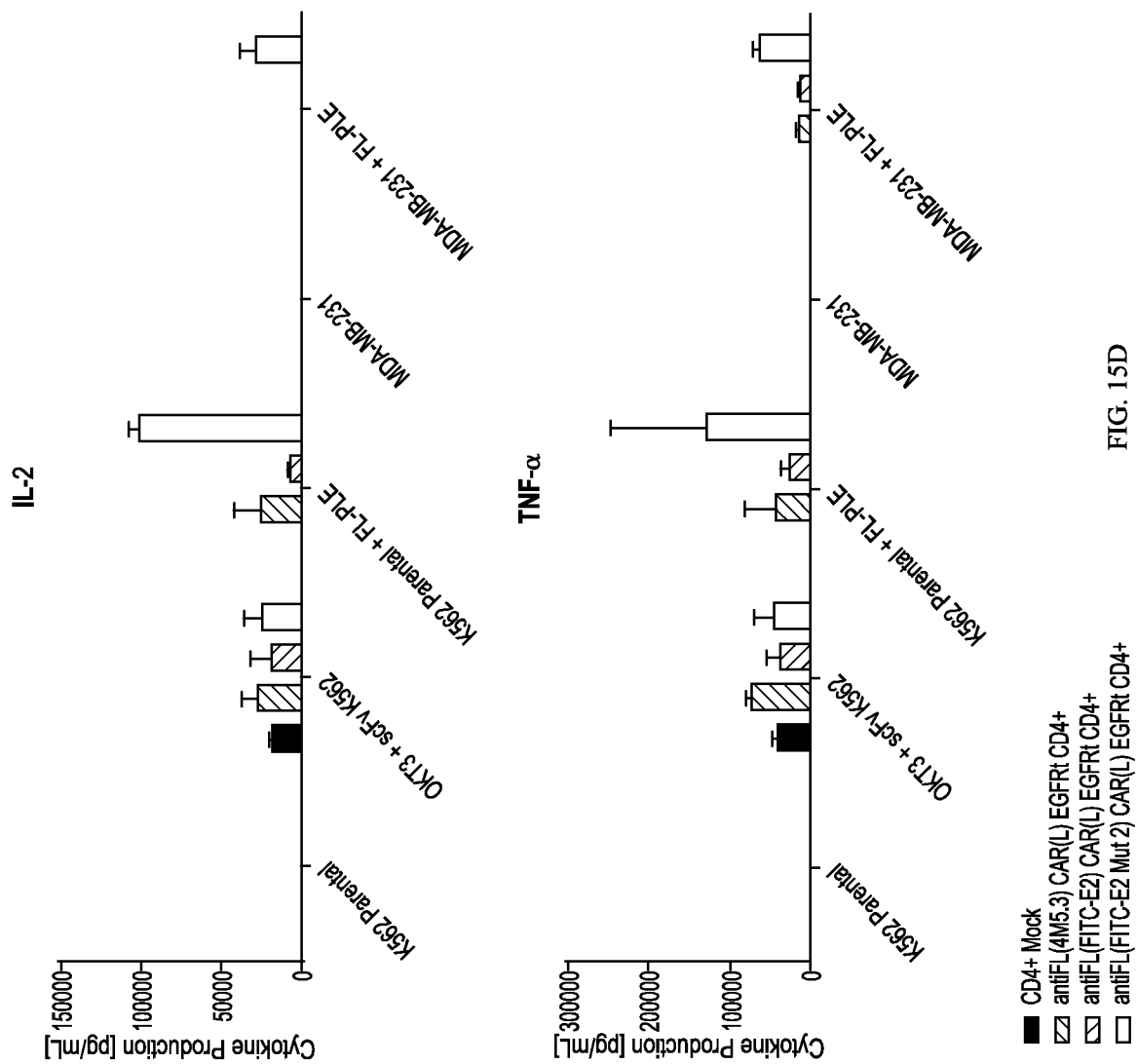
FIG. 15D depicts a series of graphs for cytokine production from T cells containing various antiFL CARs and contacted with various tumor cells in the presence or absence of FL-PLE.
Figure 15D:
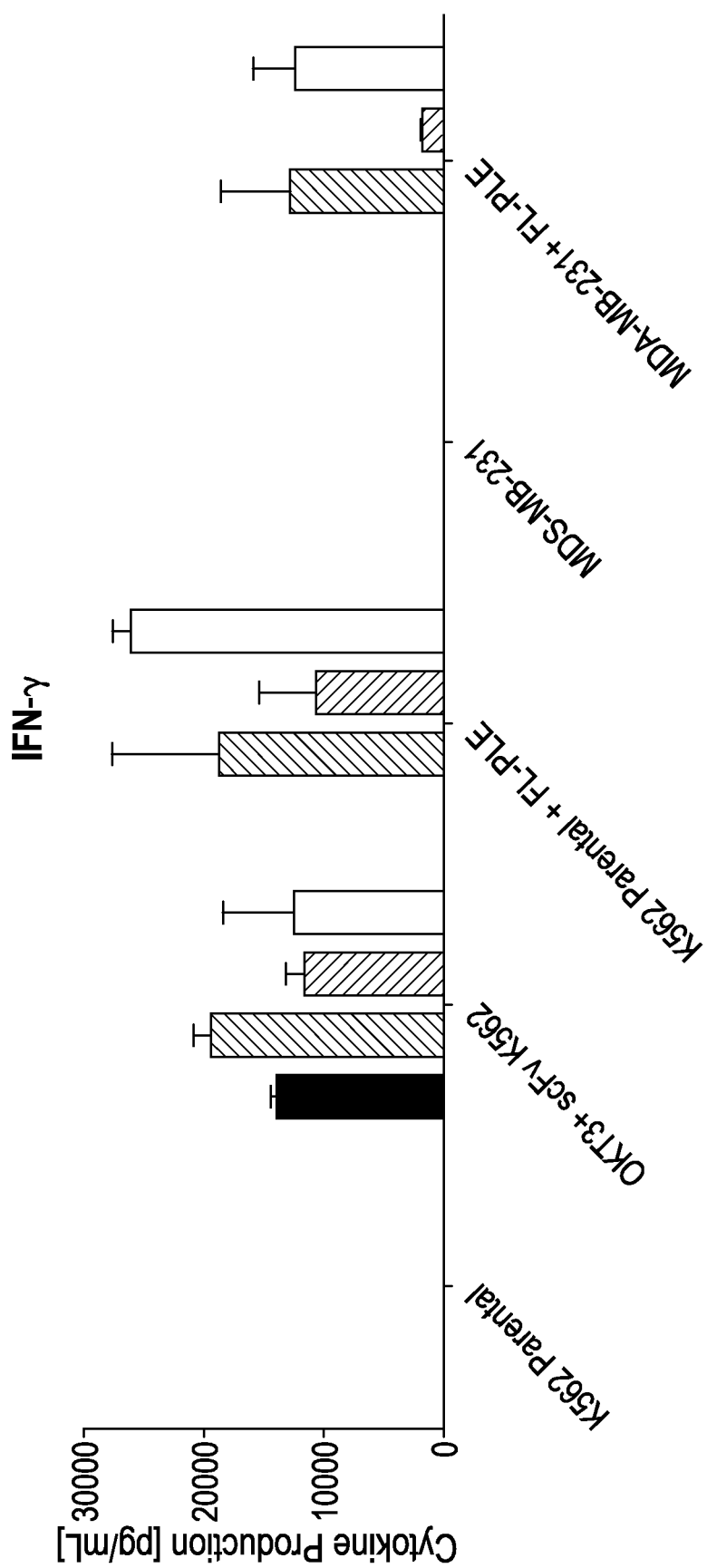
Figure 15E:
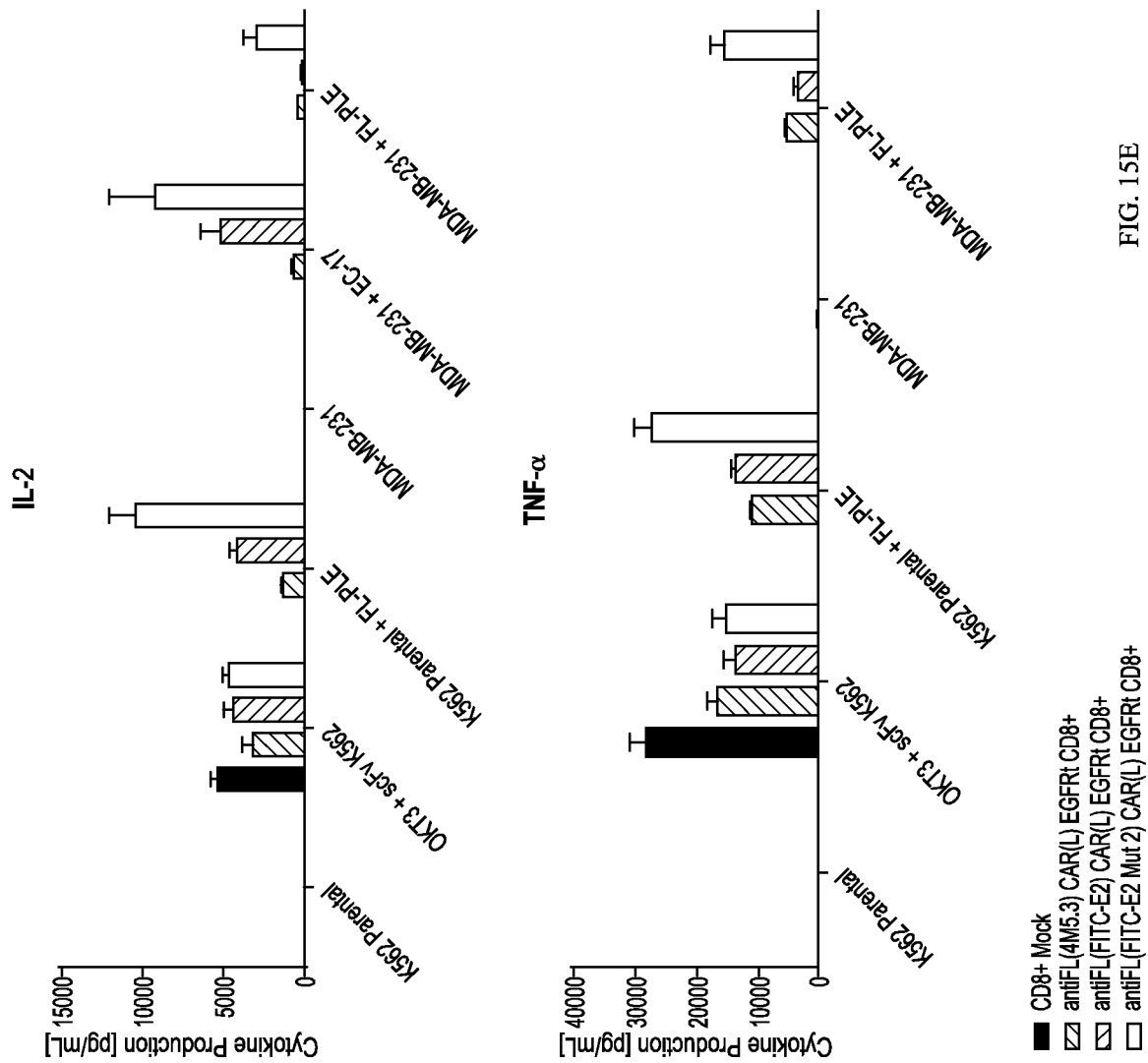
FIG. 15E depicts a series of graphs for cytokine production from T cells containing various antiFL CARs and contacted with various tumor cells in the presence or absence of FL-PLE.
Figure 15E:
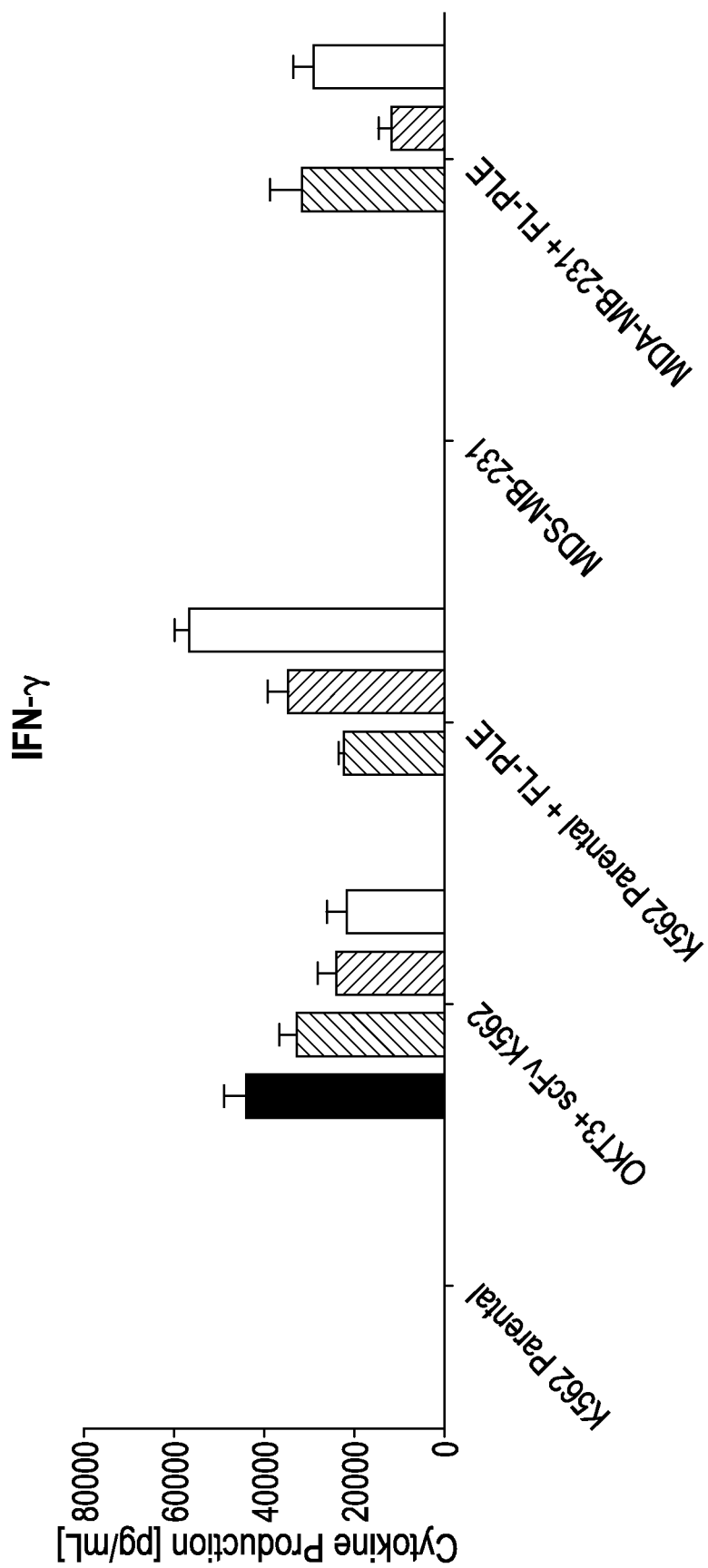

Three CARs antiFL CARs (4M5.3, FITC-E2, and FITC-E2 Mut2) with long spacer demonstrated enhanced functional output were tested further. CAR T cells were prepared with each antiFL CARs. FIG. 15A shows cell pure population of CD4+ and CD8+ antiFL CARs T cell via staining for the selection marker EGFRt. K562 (leukemia) and MDA-MB-231 (adenocarcinoma) cells were incubated with FL-PLE overnight, and cell integration of FL-PLE was analyzed by flow cytometry (FIG. 15B). There was a clear shift from the control parental cell lines with the parental cell lines incubated with 5 µM FL-PLE corresponding to the amount of FL exposed on the surface of the cell for CAR T cell recognition. The prepared CAR T cells were assayed in a chromium release assay (FIG. 15C) and in a cytokine release assay (FIG. 15D and FIG. 15E) to test the activation of the optimized antiFL CAR T cells compared to each other and mock T cells. From these experiments, in terms of recognition and activation antiFL(Mut2) CAR T cells had the greatest response followed by antiFL(FITC-E2) followed by antiFL(4M5.3) for both the leukemia and adenocarcinoma.

Example 10—In Vivo Targeting and Integration of FL-PLE

Figure 16:
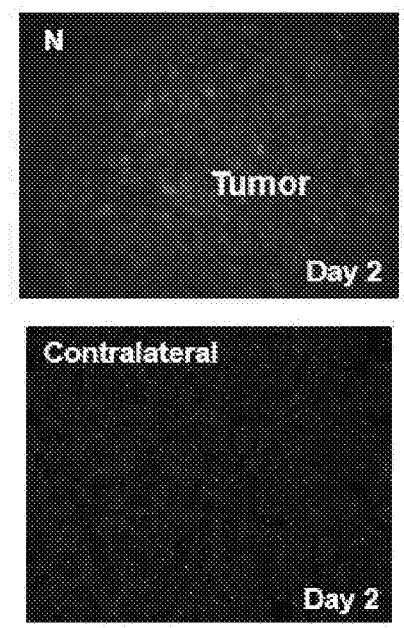
FIG. 16 (left upper panel) depicts an image of an orthotopic glioma xenograft in a subject which had been dosed intravenously with FL-PLE, and evaluated 48 hr later. Left lower panel is an image of the control contralateral hemisphere of the subject. Both the orthotopic glioma xenograft and the control contralateral hemisphere of the subject were evaluated by staining with an anti-fluorescein antibody. Levels of retained FL-PLE were also quantified in both the orthotopic glioma xenograft and the control contralateral hemisphere, over time (right panel).
Figure 16:
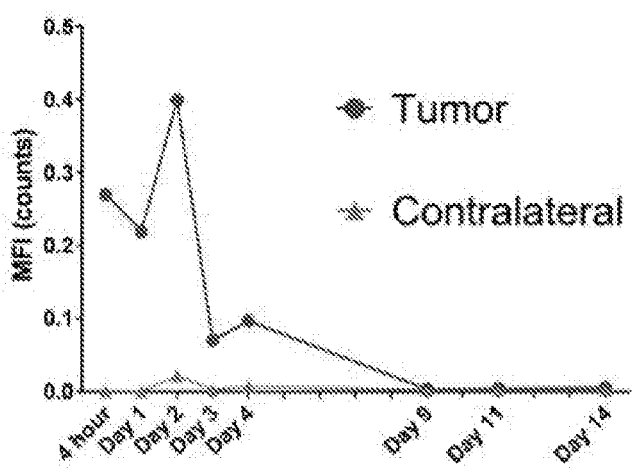

In vivo targeting and integration of FL-PLE was tested. FIG. 16 shows in vivo targeting and integration of FL-PLE with FL moiety available for binding. After a glioblastoma (U87 cells) tumor was established in a group of mice by intracranial injection, the mice received an intravenous injection of FL-PLE. Mice were sacrificed and brains were harvested at various time points post FL-PLE injection. Specifically, mice having an orthotopic glioma xenograft were dosed intravenously with FL-PLE, and the brains were evaluated over a period of 14 days. At 48 hr, the brain was prepared for histology. DAPI was also used to stain for the nucleus. An anti-Fluorescein antibody was used to stain for availability of fluorescein molecules of FL-PLE that were integrated into the membrane of cells. The glioma tumor exhibited retention of FL-PLE in excess compared to a tumor-free contra lateral hemisphere of a subject. FIG. 16 at top left shows 10× fluorescent image, tumor was very bright compared to the normal healthy tissue, labeled as N. This showed the selective integration of FL-PLE into tumor membranes with FL moiety available for binding. Bottom left: bright signals were be seen when looking at the contralateral image of the brain. Right: To quantify this the MFI of the tumor and the contralateral side were individually calculated. This analysis was then repeated at multiple time points. These values were then plotted, generating a multiday retention time plot for FL-PLE upon this dose of FL-PLE.

Figure 17:
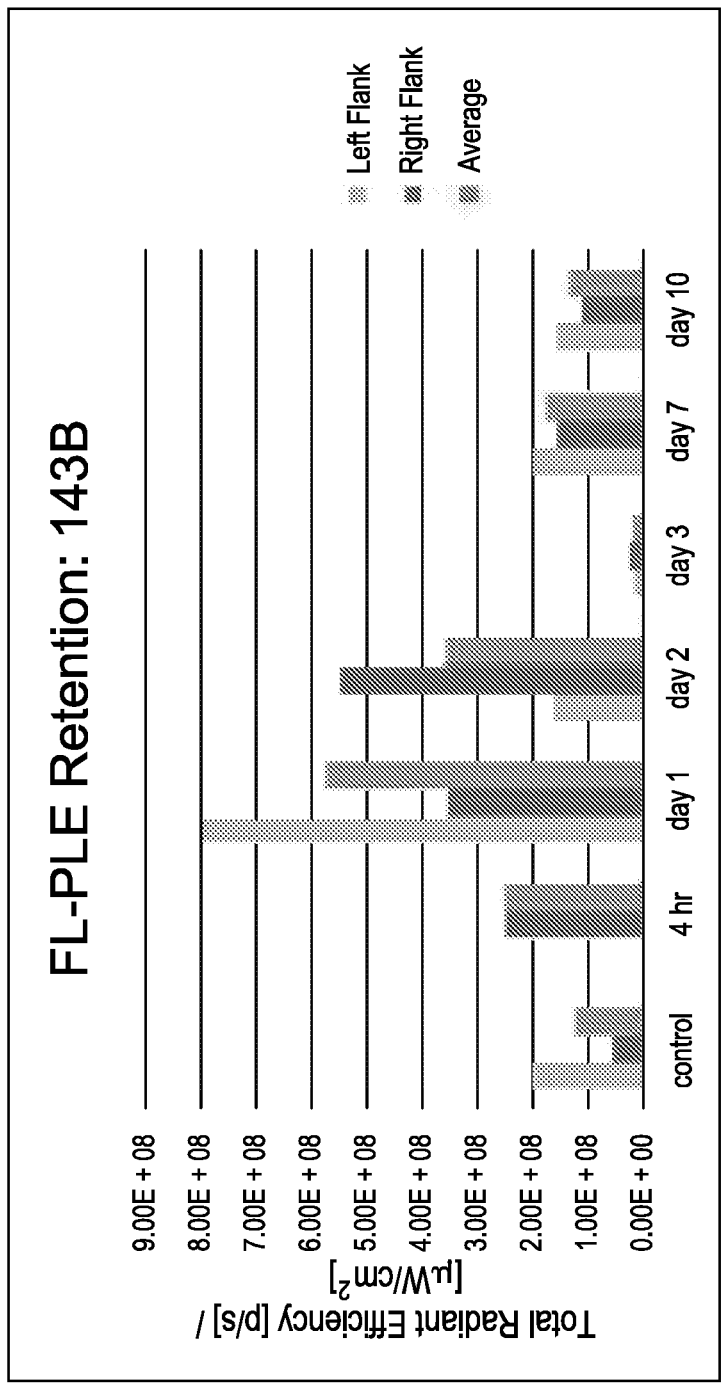
FIG. 17 depicts graphs demonstrating FL-PLE retention in different tumors in vivo.
Figure 17:
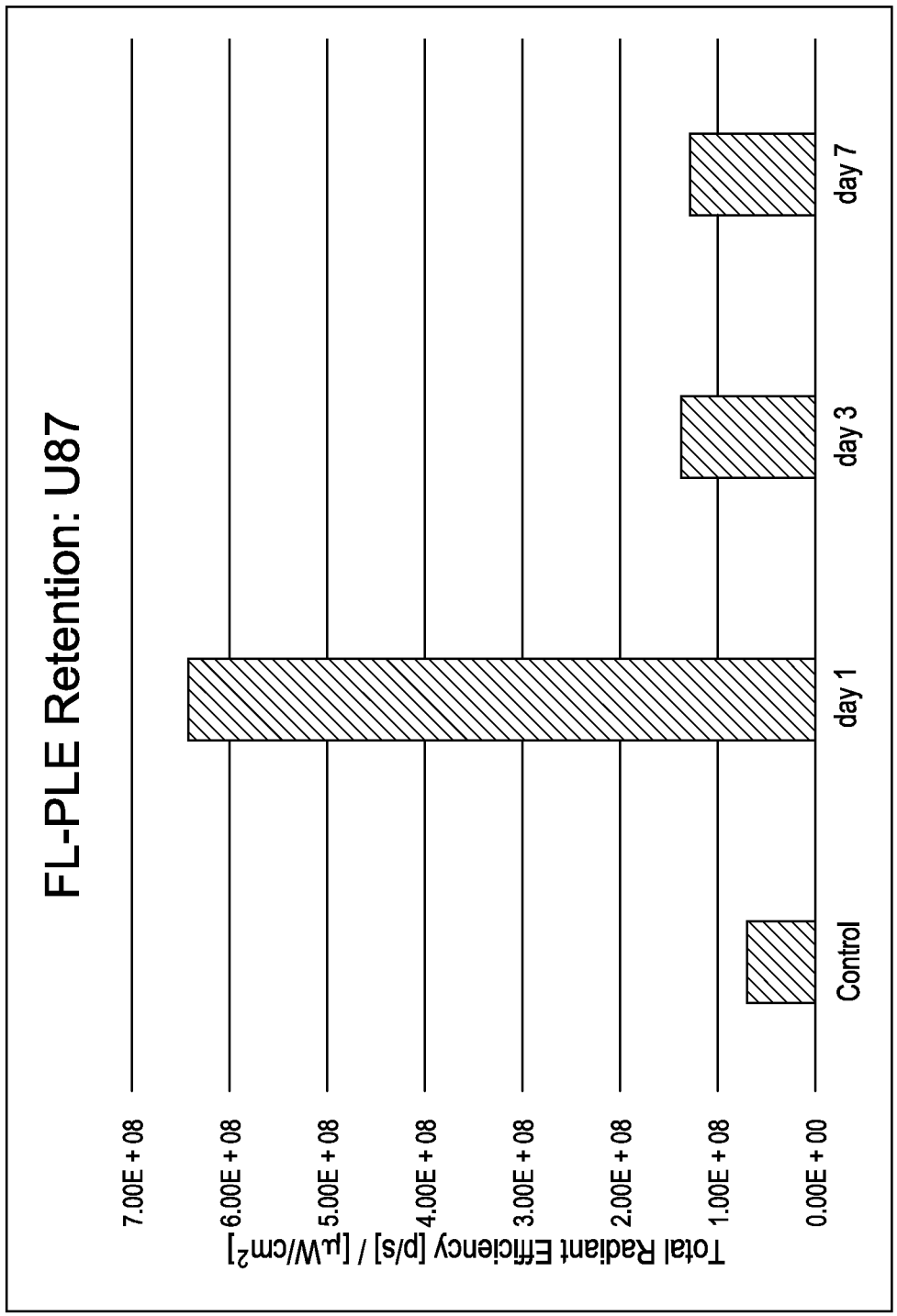
Figure 17:
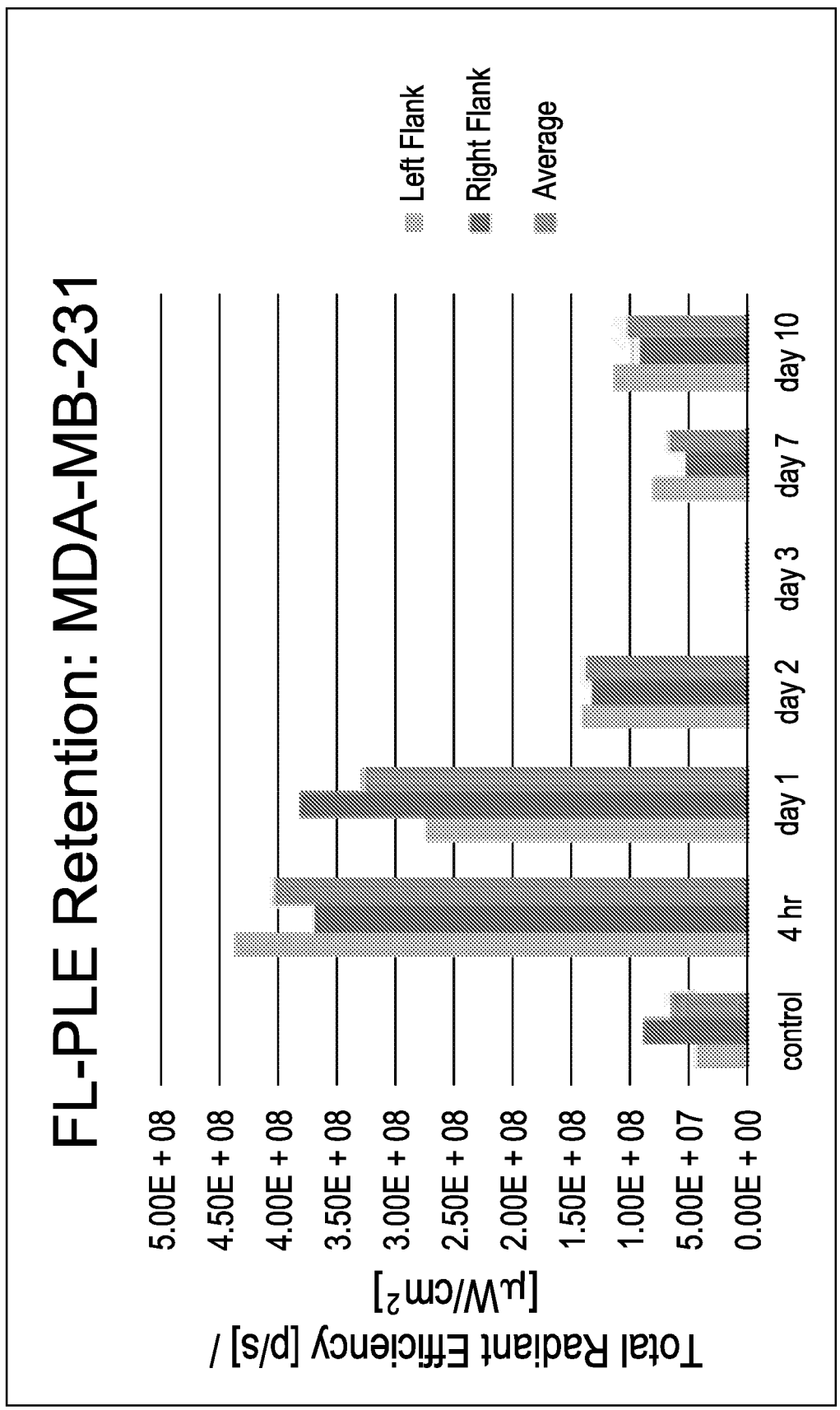
Figure 17:
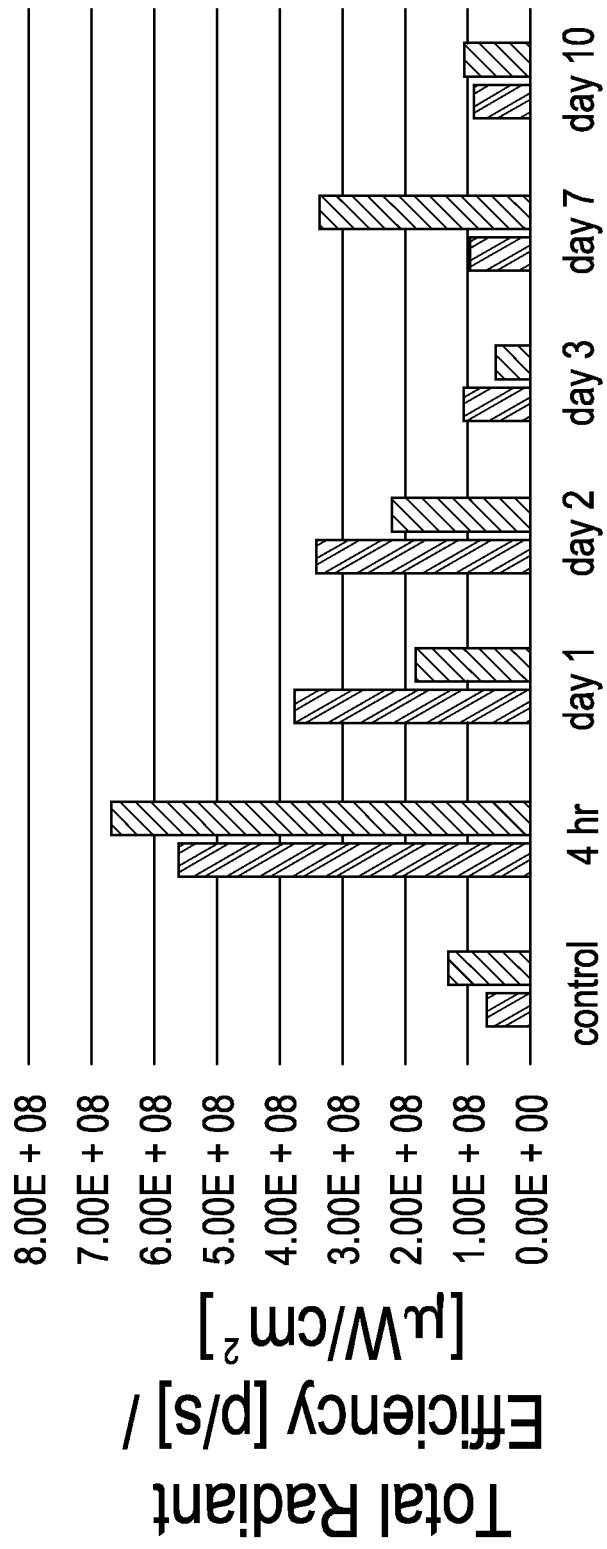

Results depicted in FIG. 17 demonstrate the universality of in vivo targeting and integration of FL-PLE. Here adenocarcinoma (MDA-MB-231), osteosarcoma (143B), and glioblastoma (U87) cell lines were used to show the universality. The adenocarcinoma and osteosarcoma each received two flank tumors in their respective groups and the glioblastoma only received one flank tumor. The fourth group had an adenocarcinoma tumor on one flank and an osteosarcoma on the opposite flank. After tumors were established in the groups of mice by subcutaneous injection, the mice received an intravenous injection of FL-PLE. Mice were sacrificed and tumors were harvested at various time points post FL-PLE injection. The tumors were removed and immediately fluorescently imaged for the presence of the fluorescein molecule on FL-PLE. The graphs of FIG. 17 for the three different types of cancer all show a multiday day retention time with FL-PLE before the tumor's fluorescence reach base line levels (tumor that has never received FL-PLE). The fourth group showed that FL-PLE simultaneously targeted two different types of cancers was retained for multiple days.

Example 11—Blocking CAR T Cell Binding with ProFL-PLE the Prodrug Version of FL-PLE (ProFL-PLE)

Figure 18A:
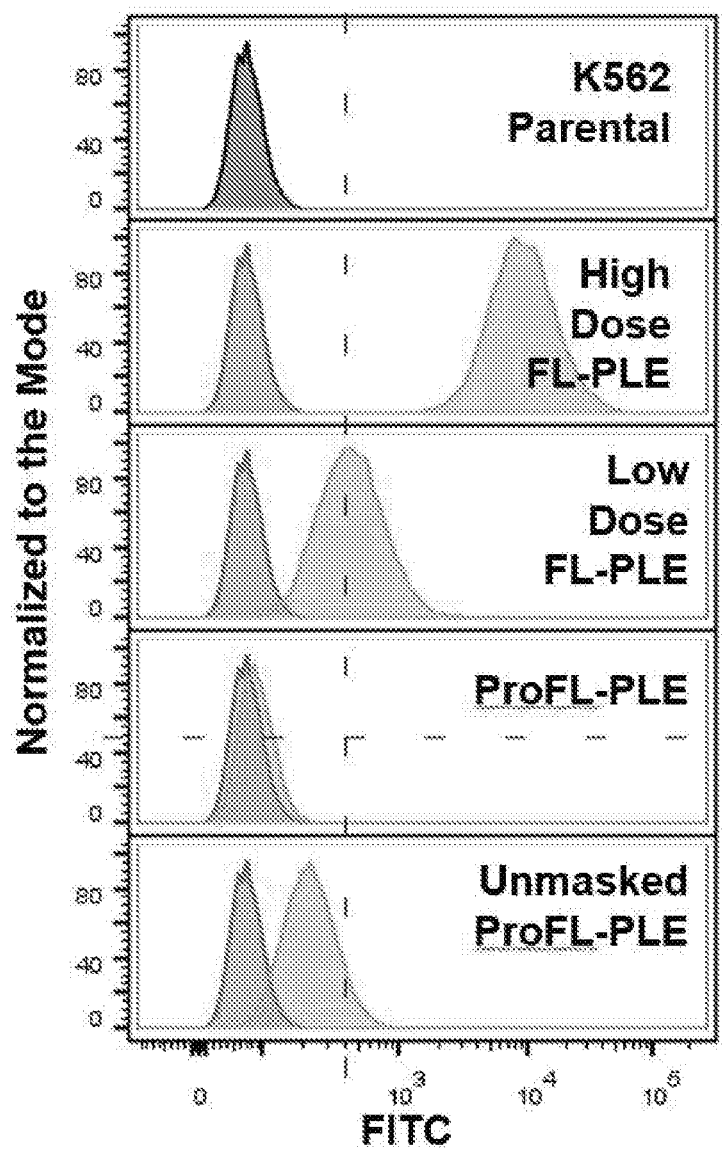
FIG. 18A depicts a FACS analysis of cells treated with FL-PLE, or ProFL-PLE.
Figure 18B:
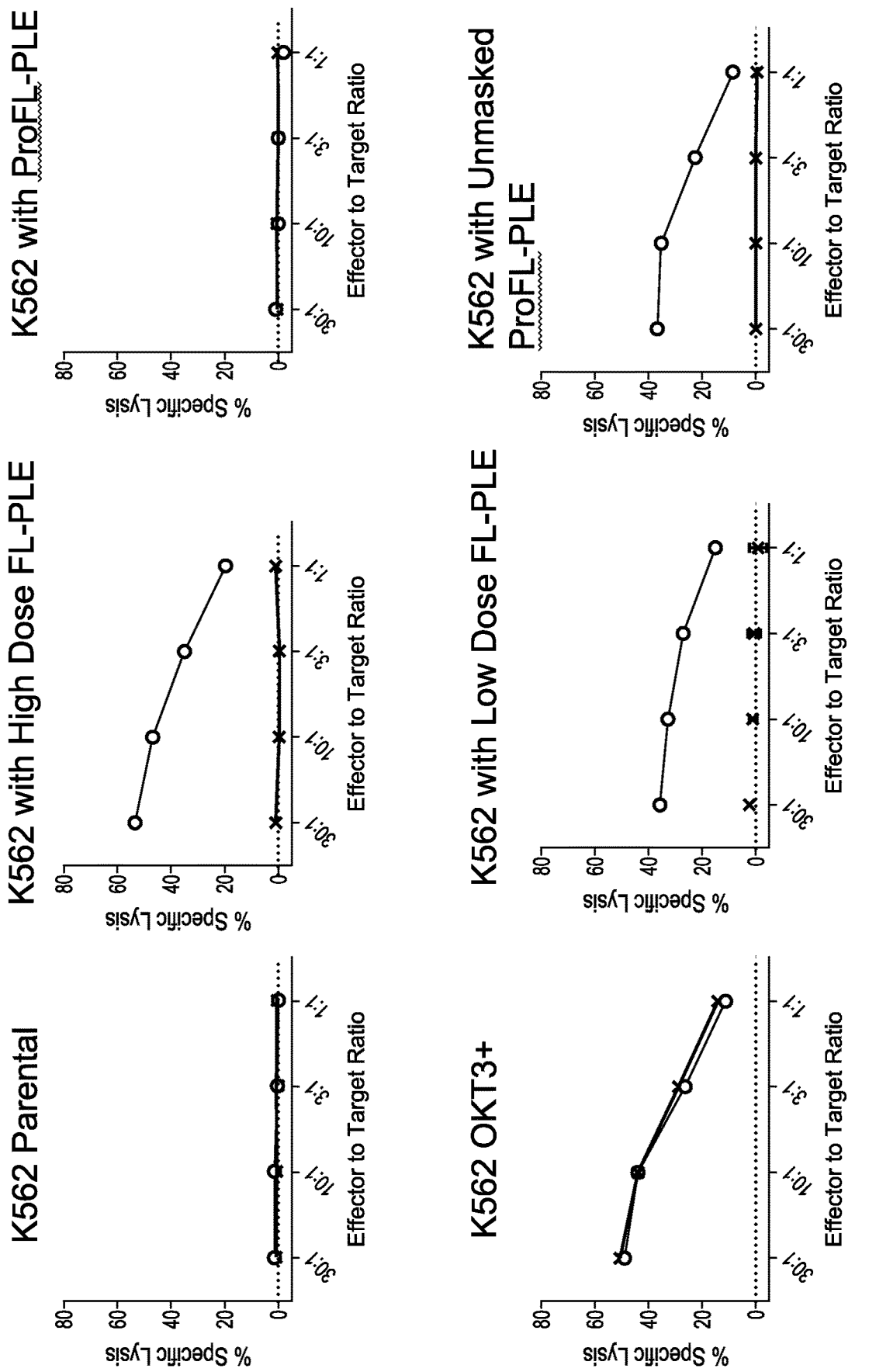
FIG. 18B depicts specific lysis of cells treated with FL-PLE or ProFL-PLE, and contacted with CD8+ T cells containing an antiFL CAR

The activity of masked FL-PLE (ProFL-PLE) to inhibit CART cell binding to cells labelled with ProFL-PLE was tested. FIG. 18A and FIG. 18B show ProFL-PLE ability to block CAR T cell recognition until unmasked. K562 (leukemia) cells were incubated with FL-PLE (high and low doses) or ProFL-PLE overnight. Cell integration of FL-PLE and ProFL-PLE was analyzed by flow cytometry (FIG. 18A). There was a clear shift from the control K562 parental with the K562 parental incubated with high dose FL-PLE whereas there was a smaller shift with K562 parental incubated with low dose FL-PLE. This slight shift corresponded to a difference in the amount of FL exposed on the surface of the cell for CAR T cell recognition. ProFL-PLE was not fluorescent due to the presence of the masking agent, a phenolic hydroxy group. Therefore, ProFL-PLE and K562 Parentals had almost the same profile as observed by flow cytometry. When ProFL-PLE was unmasked the fluorescence of the fluorescein was revealed. The unmasked ProFL-PLE had a similar amount of FL exposed on the surface as the low dose FL-PLE. FIG. 18B shows cells used in a chromium release assay to test the activation of CD8+ antiFL CART cells compared with a CD8+ mock T cells. From these experiments, antiFL CAR T cells recognized the FL moiety of the FL-PLE integrated into the plasma membrane. The ProFL-PLE completely blocked the recognition of the antiFL CARs; whereas once the Pro protection was unmasked the FL moiety was available for recognition of antiFL CARs. The lysis of the unmasked ProFL-PLE was about the same as the Low Dose FL-PLE, which correlated with the amount of FL exposed on the surface of the k562 cells.

Figure 18C:
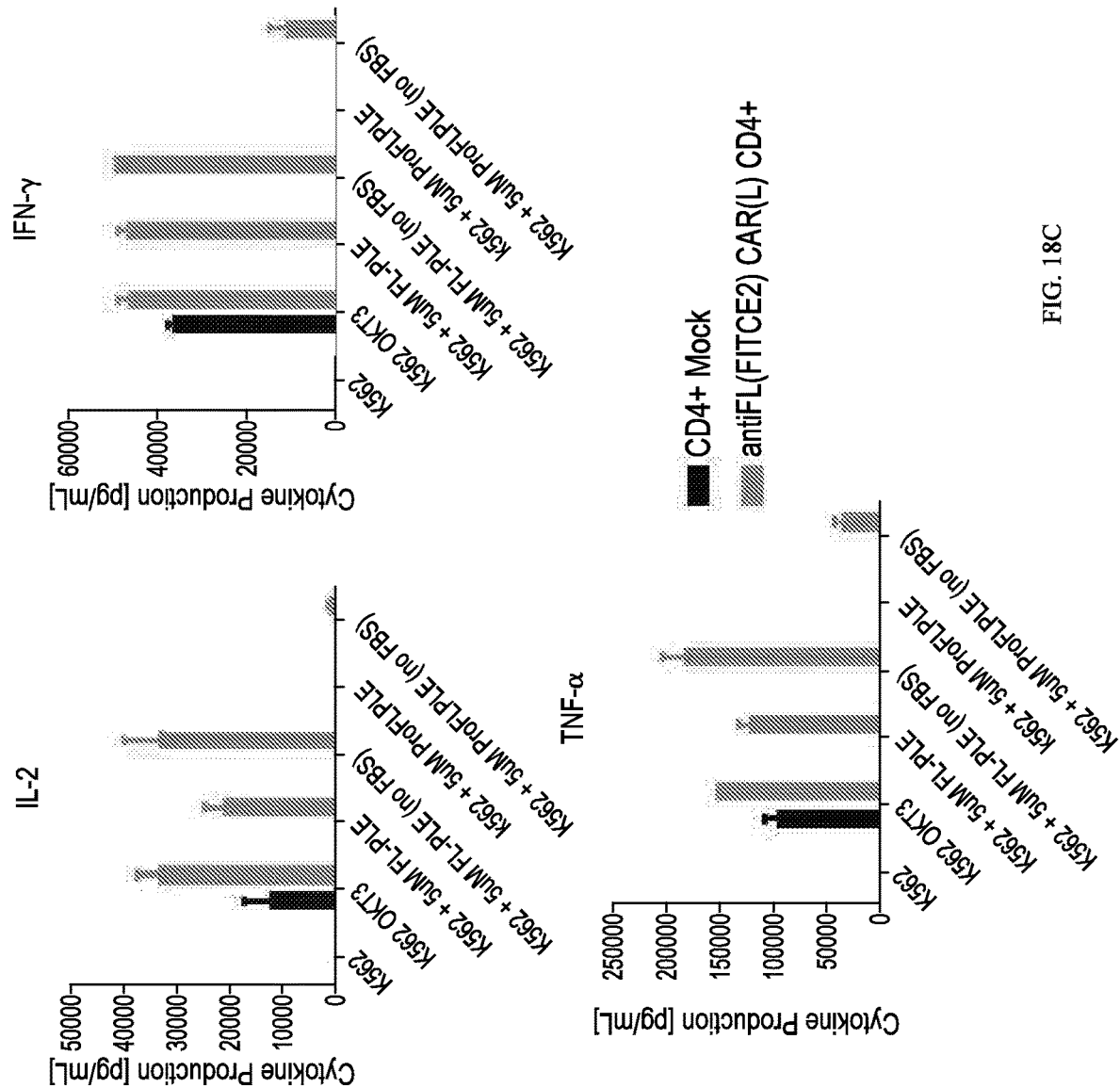
FIG. 18C depicts a series of graphs for cytokine product for cells in the presence or absence of masked or unmasked ProFL-PLE and FL-PLE, in the presence or absence of CD4+ T cells containing an antiFL(FITCE2) CAR with a long spacer.

FIGS. 18A and 18C shows cells used in a cytokine release assay to demonstrate the activation of CD4+ antiFL CAR T cells compared with a CD4+ mock T cells. Cell integration of FL-PLE and ProFL-PLE was analyzed by flow cytometry (FIG. 18A). As shown in FIG. 18C, negative controls (K562 Parental) showed no cytokine production and the positive control (K562 OKT3+ cells) showed production of all three cytokines for all cell lines. FL-PLE labeled cells were able to generate all three cytokines and was dependent on the amount of FL exposed on the surface. ProFL-PLE cells labeled with the pro moiety still intact produced no cytokine meaning the antiFL CAR T cells were not activated. After unmasking, ProFL-PLE labeled cells produced all 3 cytokines showing that upon removal of the Pro moiety the antiFL CAR T cell activated through ProFL-PLE integrated into the surface of a cancer cell. This demonstrated that labelling tumor cells with a masked hapten conjugated with a lipid, such as ProFL-PLE, unmasking the hapten to obtain a unmasked hapten conjugated to a lipid integrated into a tumor cell membrane, and contacting the unmasked hapten with an anti-hapten CAR T cell activates the T cell in at least an in vitro environment.

Figure 19A:
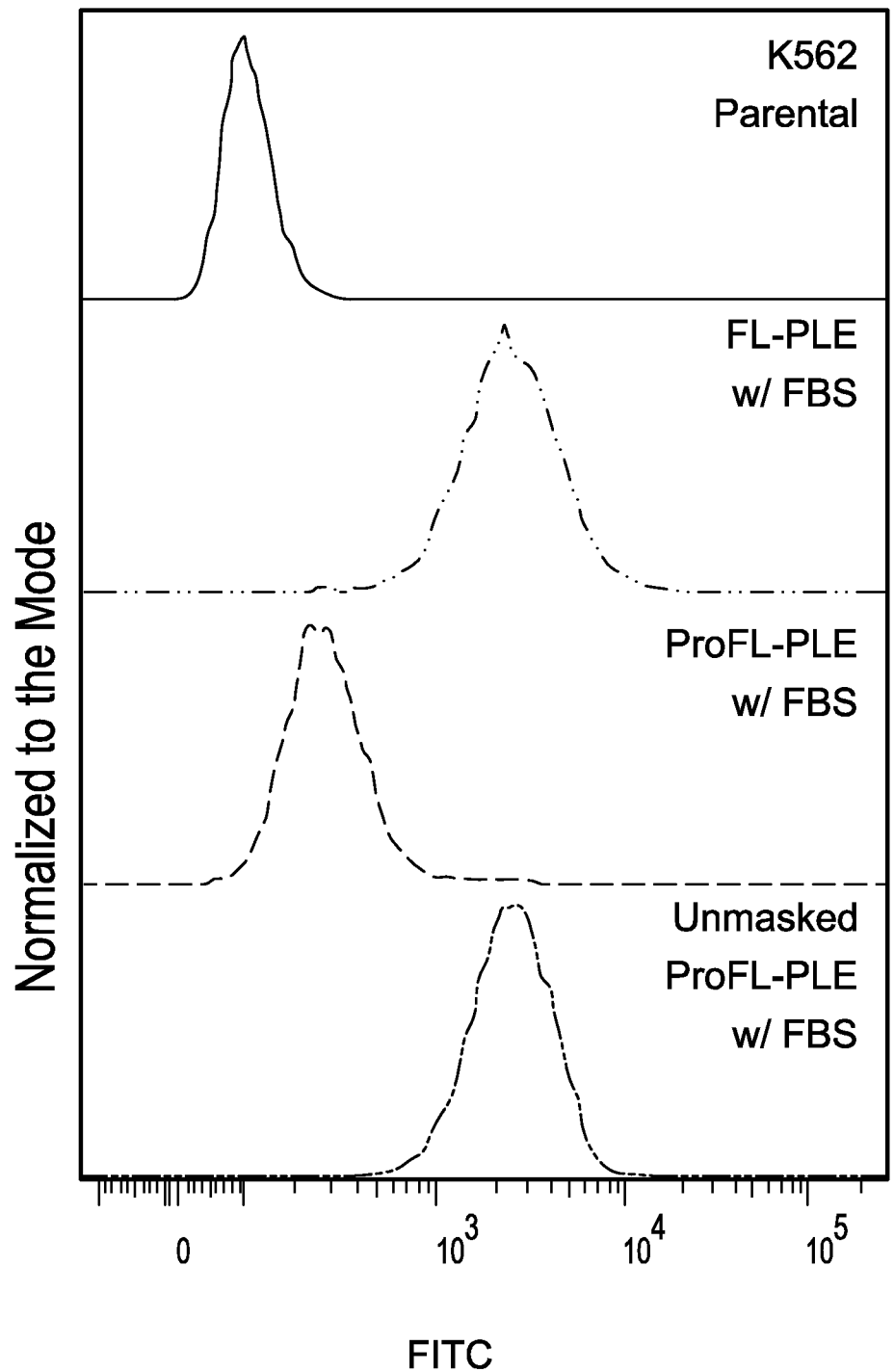
FIG. 19A depicts a FACS analysis of FL-PLE or ProFL-PLE binding to cells.
Figure 19B:
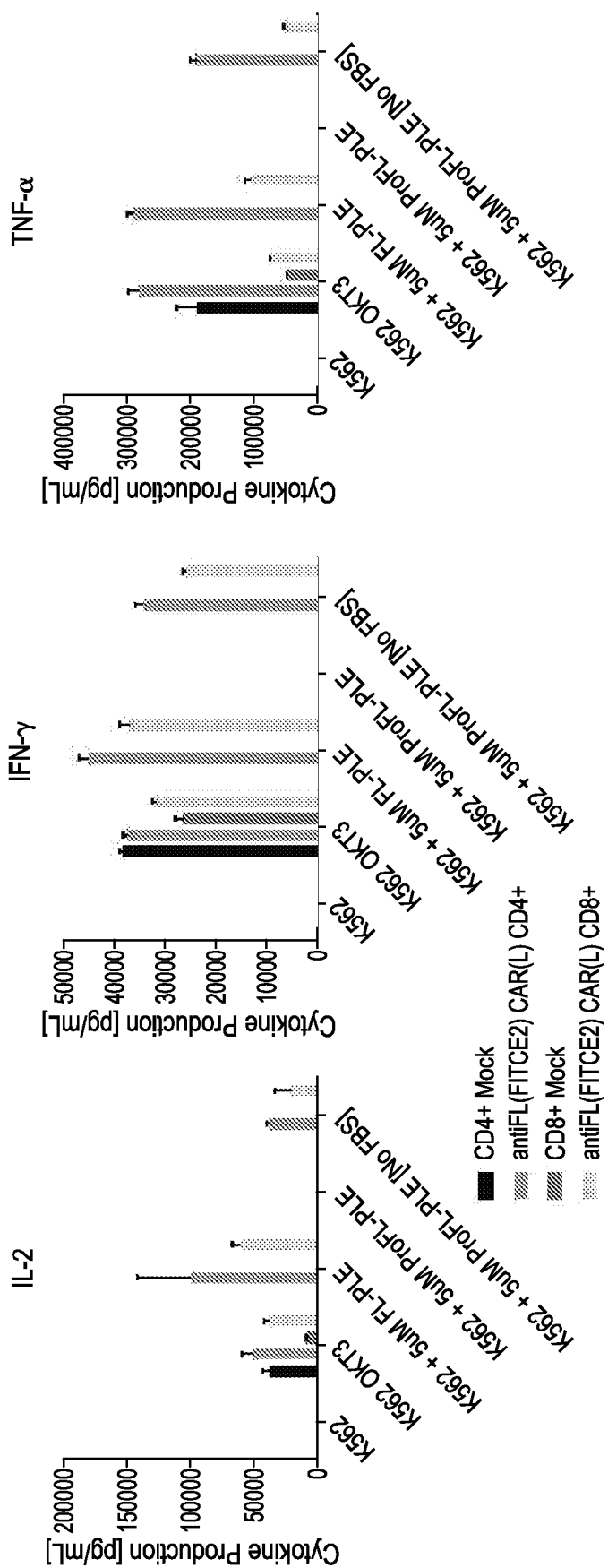
FIG. 19B depicts a series of graphs for cytokine product for cells in the presence or absence of ProFL-PLE or FL-PLE, in the presence or absence of CD4+ T cells containing an antiFL(FITCE2) CAR with a long spacer.
Figure 19C:
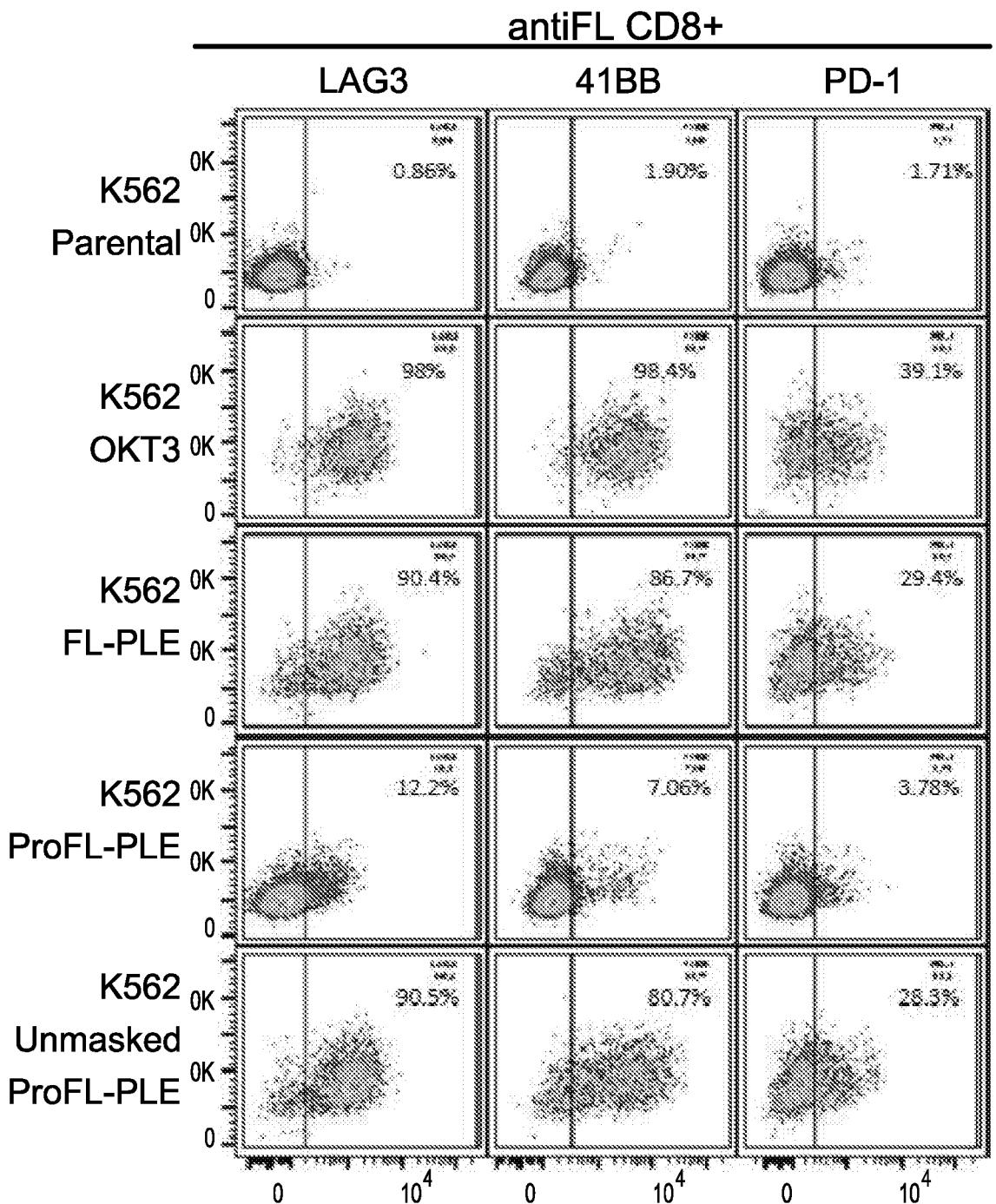
FIG. 19C depicts a FACS analysis of cells treated with FL-PLE or ProFL-PLE.

FIG. 19A, FIG. 19B, and FIG. 19C depict ProFL-PLE blocking CAR T cell recognition until unmasked, after unmasking the antiFL CAR T cell recognized the newly exposed fluorescein on the surface was then activated. K562 (leukemia) cells were incubated with FL-PLE or ProFL-PLE overnight. Cell integration of FL-PLE and ProFL-PLE was analyzed by flow cytometry (FIG. 19A). There was a clear shift from the control K562 parental with the K562 parental incubated with FL-PLE corresponding to the amount of FL exposed on the surface of the cell for CAR T cell recognition. ProFL-PLE was not fluorescent due to the presence of the masking agent, a phenolic hydroxy group. Therefore, K562 incubated with ProFL-PLE in FBS and K562 Parentals had almost the same profile as observed by flow cytometry, i.e. the Pro moiety was still intact. When ProFL-PLE was unmasked (overnight incubation in media without FBS) the fluorescence of the fluorescein was revealed. The unmasked ProFL-PLE had a similar amount of FL exposed on the surface as the K562 cells incubated with FL-PLE. FIG. 19B shows cells used in a cytokine release assay to continue to prove the activation of CD4+ and CD8+ antiFL CART cells compared with a CD4+ and CD8+ mock T cells. The negative controls (K562 Parental) showed no cytokine production and the positive control (K562 OKT3+ cells) showed production of all three cytokines for all cell lines. As expected, FL-PLE labeled cells were able to generate all three cytokines. ProFL-PLE cells labeled with the pro moiety still intact produced no cytokine meaning the antiFL CAR T cells were not activating as designed. After unmasking, ProFL-PLE labeled cells produced all 3 cytokines showing that upon removal of the Pro moiety the antiFL CAR T cell activated through the unmasked ProFL-PLE integrated into the surface of the cancer cell. This shows the design of the ProFL-PLE works in an in vitro environment. FIG. 19C depicts results of staining cells from the co-culture of the cytokine release assay to investigate the up regulation of activation markers (LAG3, 41BB, and PD-1) on the CART cells after 24 hrs. The live CD8+ antiFL(FITC-E2) long spacer CAR T cells are shown. As expected the negative control co-culture with k562 Parental showed no up regulation of activation markers and the positive control (K562 OKT3+ cells) showed up regulation of all three activation markers. The K562 cells with ProFL-PLE showed only slightly elevated amounts of the activation markers meaning the intact Pro moiety was blocking antiFL CAR T cell recognition and activation. K562 cells with FL-PLE or unmasked ProFL-PLE had similar levels of activation as the positive control showing that the antiFL CAR T cells were activating similarly through FL-PLE and unmasked ProFL-PLE.

Example 12—In Vivo Activity of antiFL CART Cells

Figure 20:
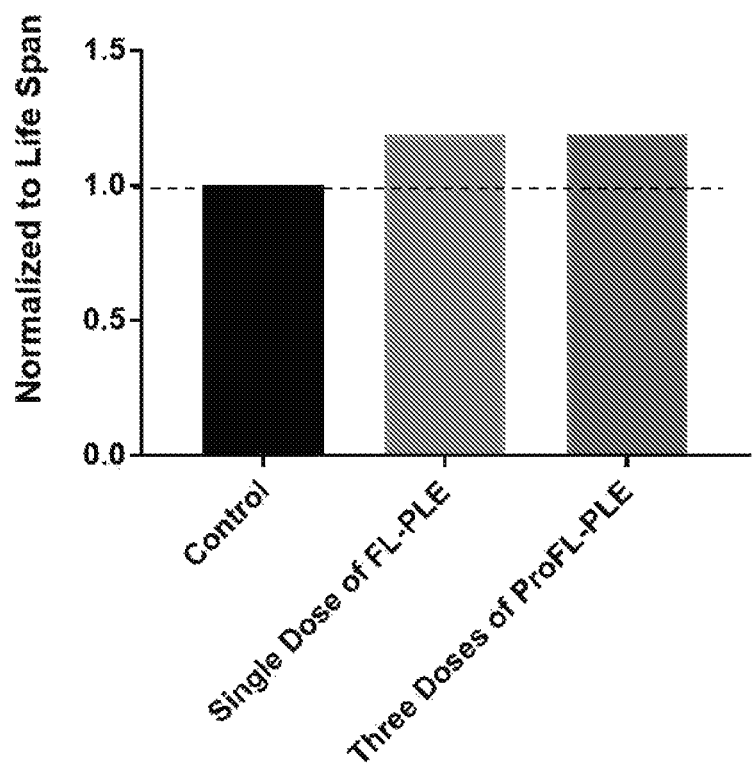
FIG. 20 depicts a graph of relative life span of mice having a neuroblastoma (Be2) tumor and treated with ProFL-PLE, FL-PLE or control, and administered either T cells containing an antiFL(FITCE2) long spacer CAR which comprised SEQ ID NO: 5, or a control.

Mice having a brain tumor were administered either masked or unmasked FL-PLE, in combination with an antiFLCAR T cell. FIG. 20 shows initial FL-PLE and ProFL-PLE in vivo therapy. After a neuroblastoma (Be2) tumor was established in 3 groups of mice by intracranial injection, the mice received an intracranial injection of T cells comprising an antiFL(FITCE2) long spacer CAR, which comprised SEQ ID NO: 5. The control group only received the antiFL(FITCE2) long spacer CAR T cells and the tumor progressed as normal (black bar). The second group receive a single intravenous injection of FL-PLE prior to T cell injection. This group lived ~20% longer than the control group. The third group received 3 scheduled doses of ProFL-PLE via intravenous injection (one before T cell injection and two post T cell injection), which led to ~20% longer life span for the mice. These results additionally confirmed that ProFL-PLE was safe for re-dosing.

Example 13—In Vivo Activity of antiFL CAR T Cells with Masked FL-PLE

Figure 21A:
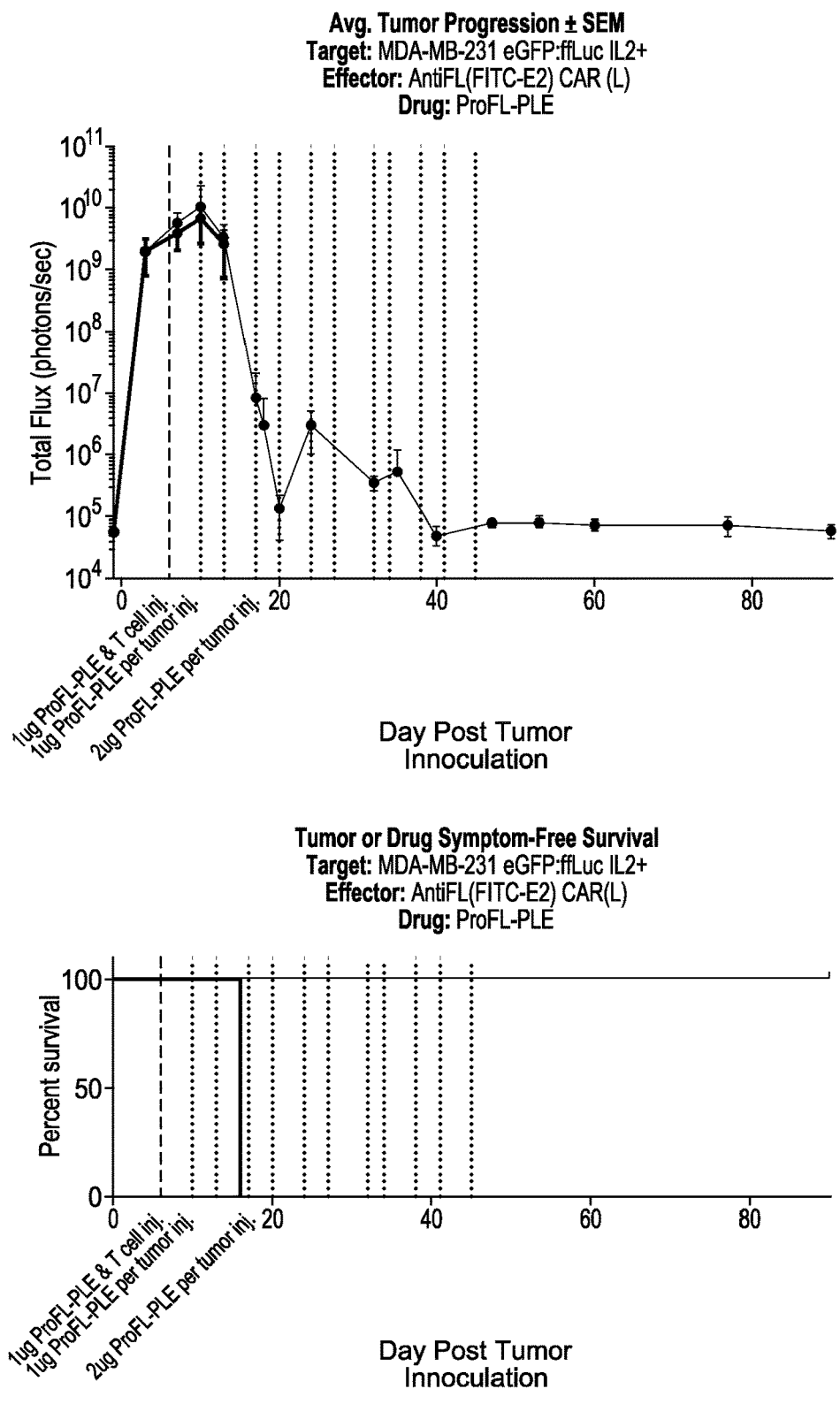
FIG. 21A depicts graphs for average tumor progression (top panel), and percent survival (bottom panel) in mice injected intra-tumorally with ProFL-PLE, and administered T cells containing an antiFL(FITCE2) CAR with a long spacer.
Figure 21B:
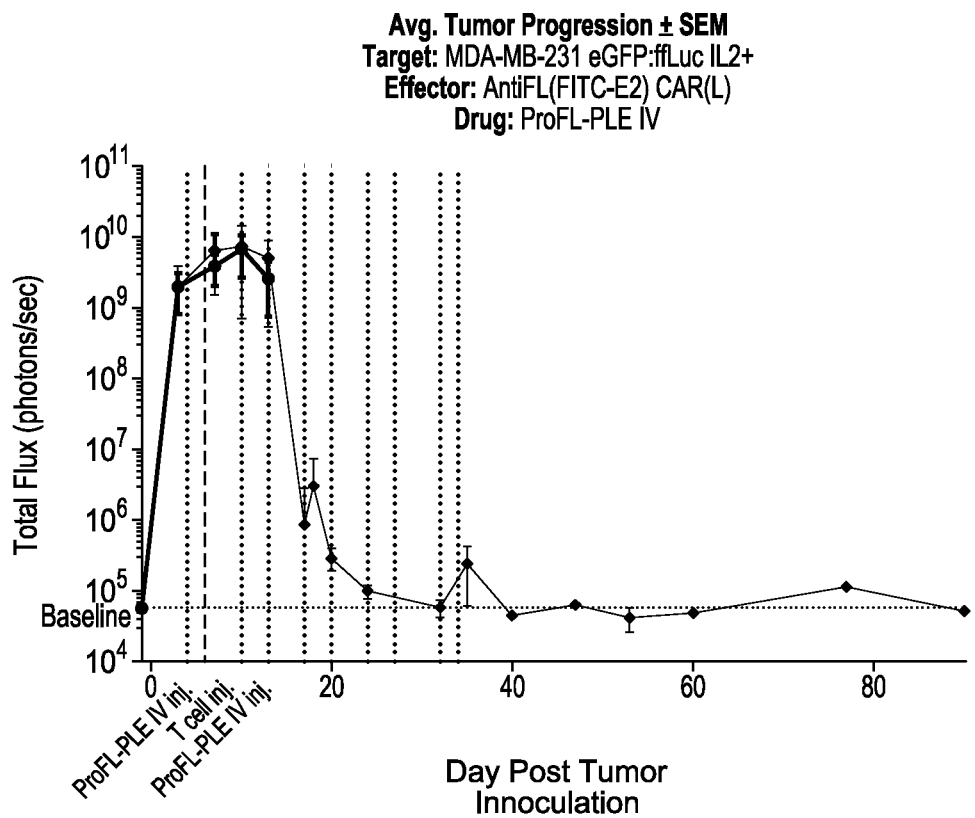
FIG. 21B depicts graphs for average tumor progression (top panel), and percent survival (bottom panel) in mice injected intravenously with ProFL-PLE, and administered T cells containing an antiFL(FITCE2) CAR with a long spacer.
Figure 21B:
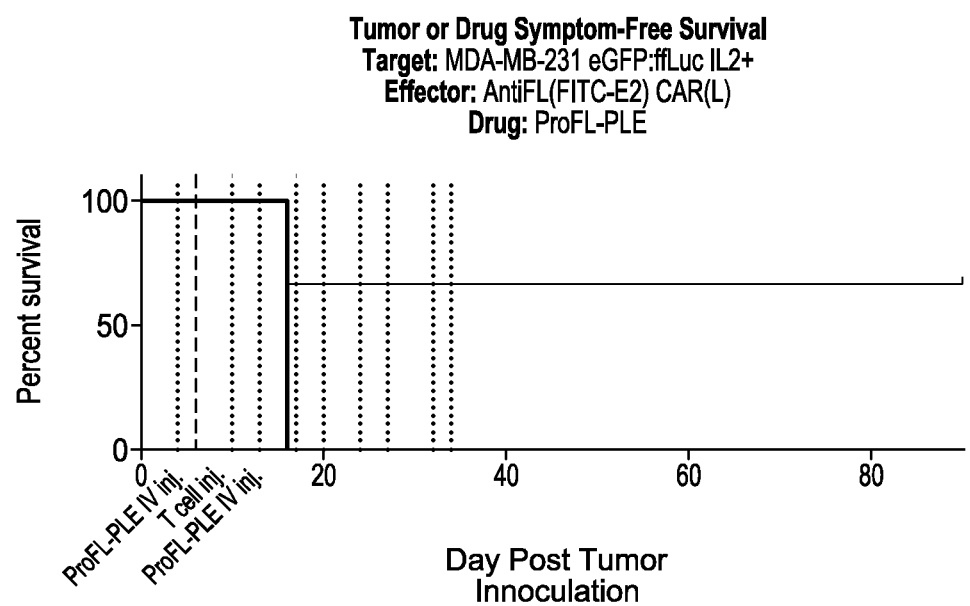

Administration of masked FL-PLE (ProFL-PLE) in combination with an antiFL CAR T cells was tested in mice with a breast cancer cell model. FIG. 21A and FIG. 21B show ProFL-PLE in vivo therapy for a flank tumor model. After adenocarcinoma (MDA-MB-231 eGFP:ffLuc IL2+) tumors (2 tumors per mouse) were established in three groups of mice by subcutaneous injection, two groups of mice received injection of ProFL-PLE either intratumorally (FIG. 21A) or intravenously (IV) (FIG. 21B) and the control group received no injection of drug. Following the first injection of drug all three groups received IV injection of cells containing the antiFL(FITC-E2) long spacer CAR. The grey vertical dotted lines on the graphs represent the days of injection. The control group died after 16 days from tumor burden. (FIG. 21A) The ProFL-PLE intratumorally injected group received 12 doses of ProFL-PLE over 45 days and the tumor regressed to baseline levels by day 40 for all 3 mice. The mice lived tumor free till the end of the study on day 90. (FIG. 21B) The ProFL-PLE IV injected group received 10 doses of ProFL-PLE over 34 days and the tumor regressed to baseline levels by day ~40 for 2 mice. These mice lived tumor free till the end of the study on day 90. One mouse from this group died on day 16 with the control mice. These results demonstrate that ProFL-PLE injected intratumorally or IV in combination with antiFL CART cells was a viable therapy.

The following references are each expressly incorporated by reference in its entirety.

REFERENCES

1. Ma, J. S. et al. (2016). Versatile strategy for controlling the specificity and activity of engineered T cells. Versatile strategy for controlling the specificity and activity of engineered T cells. Proceedings of the National Academy of Sciences of the United States of America, 113(4), E450-E458.

2. Kim, M. S. et al. (2015). Redirection of Genetically Engineered CAR-T Cells Using Bifunctional Small Molecules. Journal of the American Chemical Society, 137(8), 2832-2835.
3. Urbanska, K. et al. (2012). A universal strategy for adoptive immunotherapy of cancer through use of a novel T-cell antigen receptor. Cancer Research, 72(7), 1844-1852.
4. Wu, C. Y. et al. (2015). Remote control of therapeutic T cells through a small molecule-gated chimeric receptor. Science, 350(6258), aab4077-aab4077.
5. Kranz et al. (1981). Partial elucidation of an anti-hapten repertoire in BALB/c mice: comparative characterization of several monoclonal antiFLuorescyl antibodies. Mol Immunol, 18(10), 889-898.
6. Jung et al. (1997). Improving in vivo folding and stability of a single-chain Fv antibody fragment by loop grafting. Protein Engineering Design & Selection, 10(8), 956-966.
7. Schwesinger et al. (2000). Unbinding forces of single antibody-antigen complexes correlate with their thermal dissociation rates. PNAS, 97(18), 9972-9977.
8. Boder et al. (2000). Directed evolution of antibody fragments with monovalent femtomolar antigen-binding affinity. PNAS, 97(20), 10701-10705.
9. Honegger et al. (2005). A mutation designed to alter crystal packing permits structural analysis of a tight-binding fluorescein-scFv complex. Prot Sci, 14(10), 2537-2549.

It is understood that the examples and alternatives described herein are for illustrative purposes only and that various modifications or changes in light thereof will be suggested to persons skilled in the art and are to be included within the spirit and purview of this application and scope of any appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to alternatives containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A method of treating or inhibiting a solid tumor in a subject in need thereof, wherein the subject's bloodstream comprises engineered T cells comprising a chimeric antigen receptor (CAR), wherein the CAR specifically binds fluorescein, the method comprising:
administering to the subject a composition comprising fluorescein conjugated to a phospholipid ether (FL-PLE) in an amount effective to label tumor cells in the solid tumor,
wherein the T cells comprising the CAR that specifically bind the fluorescein and kill tumor cells in the solid tumor, thereby treating or inhibiting the solid tumor.

2. The method of claim 1, wherein the solid tumor is a breast cancer.

3. The method of claim 1, wherein the FL-PLE comprises a masking moiety.

4. The method of claim 3, wherein the masking moiety is cleaved by reactive oxygen species (ROS) present in a tumor microenvironment of the solid tumor.

5. The method of claim 4, wherein the masking moiety comprises a phenolic hydroxyl group bound to a hydroxyl on a xanthene moiety of the FL-PLE.

6. The method of claim 1, wherein the CAR comprises a ligand binding domain comprising an amino acid sequence having at least 95% sequence identity with any one of SEQ ID NOs: 1-6.

7. The method of claim 1, wherein the CAR comprises a spacer domain consisting of an IgG4 hinge connected to a CH2 domain and a CH3 domain.

8. The method of claim 1, wherein the CAR comprises a spacer domain consisting of an IgG4 hinge connected to a CH3 domain.

9. The method of claim 1, wherein the CAR comprises a spacer domain having a length of 51-100 amino acids.

10. The method of claim 1, wherein the CAR comprises a spacer domain having a length of 100-150 amino acids.

11. The method of claim 1, wherein the CAR comprises a spacer domain having a length of 150-250 amino acids.

12. The method of claim 6, wherein the ligand binding domain comprises the amino acid sequence having at least 95% sequence identity with SEQ ID NO: 1.

13. The method of claim 6, wherein the ligand binding domain comprises the amino acid sequence having at least 95% sequence identity with SEQ ID NO: 2.

14. The method of claim 6, wherein the ligand binding domain comprises the amino acid sequence having at least 95% sequence identity with SEQ ID NO: 5.

15. The method of claim 1, wherein the method increases survival of the subject compared to a subject not administered the FL-PLE.

16. The method of claim 1, wherein the FL-PLE comprises a masking moiety; and the CAR comprises a spacer domain comprising an IgG4 hinge, a CH2 domain and a CH3 domain.

17. The method of claim 16, wherein the spacer domain comprises an amino acid sequence having at least 95% sequence identity with SEQ ID NO: 07.

18. A method of treating or inhibiting a solid tumor in a subject in need thereof, comprising:
administering to the subject (i) a composition comprising fluorescein conjugated to a phospholipid ether (FL-PLE) in an amount effective to label tumor cells in the solid tumor, and (ii) a T cell comprising a chimeric antigen receptor (CAR), wherein the CAR specifically binds the fluorescein.

* * * * *